US012799195B2

(12) United States Patent
Zhou et al.

(10) Patent No.: US 12,799,195 B2
(45) Date of Patent: Nov. 17, 2026

(54) ANTI-Claudin18.2 ANTIBODY AND USE THEREOF

(71) Applicant: FORTVITA BIOLOGICS (SINGAPORE) PTE. LTD., Singapore (SG)

(72) Inventors: Shuaixiang Zhou, Suzhou (CN); Li Li, Suzhou (CN); Zhe Guan, Suzhou (CN); Jie Wang, Suzhou (CN)

(73) Assignee: FORTVITA BIOLOGICS (SINGAPORE) PTE. LTD., Singapore (SG)

(*) Notice: Subject to any disclaimer, the term of this patent is extended or adjusted under 35 U.S.C. 154(b) by 910 days.

(21) Appl. No.: 18/010,944

(22) PCT Filed: Jun. 18, 2021

(86) PCT No.: PCT/CN2021/100870
§ 371 (c)(1),
(2) Date: Dec. 16, 2022

(87) PCT Pub. No.: WO2021/254481
PCT Pub. Date: Dec. 23, 2021

(65) Prior Publication Data

US 2023/0235047 A1 Jul. 27, 2023

(30) Foreign Application Priority Data

Jun. 19, 2020 (CN) ........................ 202010570517.X

(51) Int. Cl.
*C07K 16/28* (2006.01)
*A61K 39/395* (2006.01)
(Continued)

(52) U.S. Cl.
CPC .......... *C07K 16/28* (2013.01); *A61K 39/3955* (2013.01); *A61P 35/00* (2018.01); (Continued)

(58) Field of Classification Search
None
See application file for complete search history.

(56) References Cited

U.S. PATENT DOCUMENTS 10,017,564 B2 7/2018 Sahin et al.
10,421,817 B1 9/2019 Hu et al.
(Continued)

FOREIGN PATENT DOCUMENTS

CN 104968367 A 10/2015
CN 105073776 A 11/2015
(Continued)

OTHER PUBLICATIONS

Tsuji et al., Somatic Hypermutation and Framework Mutations of Variable Region Contribute to Anti-Zika Virus-Specific Monoclonal Antibody Binding and Function, J. Virol. 96(11), doi.org/10.1128/jvi.00071-22, 18 page, Jun. 2022.*
(Continued)

*Primary Examiner* — Claire Kaufman
(74) *Attorney, Agent, or Firm* — LEASON ELLIS LLP

(57) ABSTRACT

The present invention relates to a novel antibody and an antibody fragment that specifically bind to Claudin18.2 and a composition comprising the antibody or the antibody fragment. In addition, the present invention relates to a nucleic acid encoding the antibody or the antibody fragment thereof, a host cell comprising the nucleic acid, and related uses. Furthermore, the present invention relates to therapeutic and diagnostic uses of the antibody and the antibody fragment.

26 Claims, 9 Drawing Sheets

Specification includes a Sequence Listing.

(51) Int. Cl.
*A61P 35/00* (2006.01)
*G01N 33/57525* (2026.01)
*A61K 39/00* (2006.01)

(52) U.S. Cl.
CPC .. *G01N 33/57525* (2026.01); *A61K 2039/505* (2013.01); *C07K 2317/24* (2013.01); *C07K 2317/732* (2013.01); *C07K 2317/734* (2013.01); *C07K 2317/92* (2013.01)

(56) References Cited

U.S. PATENT DOCUMENTS

| | | | | |
|---|---|---|---|---|
| 11,111,295 | B2 * | 9/2021 | Wang | C07K 16/28 |
| 11,555,070 | B2 * | 1/2023 | Wang | A61P 35/00 |
| 2018/0117174 | A1 | 5/2018 | Sahin et al. | |
| 2020/0055932 | A1 | 2/2020 | Dahlhoff et al. | |
| 2020/0093860 | A1 | 3/2020 | Stubenrauch et al. | |
| 2020/0316128 | A1 | 10/2020 | Klein et al. | |
| 2023/0357389 | A1 | 11/2023 | Zhou et al. | |

FOREIGN PATENT DOCUMENTS

| | | | |
|---|---|---|---|
| CN | 105315375 | A | 2/2016 |
| CN | 106589127 | A | 4/2017 |
| CN | 109762067 | A | 5/2019 |
| CN | 110023336 | A | 7/2019 |
| CN | 110606891 | A | 12/2019 |
| CN | 110662560 | A | 1/2020 |
| CN | 110862454 | A | 3/2020 |
| CN | 111110862 | A | 5/2020 |
| CN | 111164208 | A | 5/2020 |
| CN | 111247429 | A | 6/2020 |
| CN | 111655290 | A | 9/2020 |
| CN | 112111013 | A | 12/2020 |
| CN | 112237634 | A | 1/2021 |
| CN | 112707965 | A | 4/2021 |
| CN | 113354739 | A | 9/2021 |
| CN | 114040777 | A | 2/2022 |
| CN | 109790222 | B | 3/2022 |
| CN | 114146174 | A | 3/2022 |
| CN | 115969997 | A | 4/2023 |
| CN | 119139489 | A | 12/2024 |
| EP | 3483182 | A1 | 5/2019 |
| EP | 2920209 | B1 | 8/2020 |
| EP | 3808376 | A1 | 4/2021 |
| EP | 2958945 | B1 | 10/2022 |
| EP | 4177273 | A1 | 5/2023 |
| EP | 4269436 | A1 | 11/2023 |
| JP | 2014240412 | A | 12/2014 |
| JP | 2016500059 | A | 1/2016 |
| JP | 2017197512 | A | 11/2017 |
| JP | 2020018298 | A | 2/2020 |
| JP | 2020505929 | A | 2/2020 |
| JP | 2020508054 | A | 3/2020 |
| TW | 202003562 | A | 1/2020 |
| TW | 202220702 | A | 6/2022 |
| WO | 2014065661 | A1 | 5/2014 |
| WO | 2014075697 | A1 | 5/2014 |
| WO | 2014146672 | A1 | 9/2014 |
| WO | 2014164503 | A1 | 10/2014 |
| WO | 2016165762 | A1 | 10/2016 |
| WO | 2016170186 | A1 | 10/2016 |
| WO | 2017137459 | A1 | 8/2017 |
| WO | 2018054484 | A1 | 3/2018 |
| WO | 2018219901 | A1 | 12/2018 |
| WO | 2019065964 | A1 | 4/2019 |
| WO | 2019075405 | A1 | 4/2019 |
| WO | 2019173420 | A1 | 9/2019 |
| WO | 2019174617 | A1 | 9/2019 |
| WO | 2019213331 | A1 | 11/2019 |
| WO | 2019219089 | A1 | 11/2019 |
| WO | 2019242505 | A1 | 12/2019 |
| WO | 2020025792 | A1 | 2/2020 |
| WO | 2020023679 | A1 | 6/2020 |
| WO | 2020114480 | A1 | 6/2020 |
| WO | 2022136642 | A1 | 6/2020 |
| WO | 2020135201 | A1 | 7/2020 |
| WO | 2020139956 | A1 | 7/2020 |
| WO | 2020196474 | A1 | 10/2020 |
| WO | 2020239005 | A1 | 12/2020 |
| WO | 2021008463 | A1 | 1/2021 |
| WO | 2021143767 | A1 | 7/2021 |
| WO | 2020059772 | A | 8/2021 |
| WO | 2021228141 | A1 | 11/2021 |
| WO | 2021254481 | A1 | 12/2021 |
| WO | 2022017468 | A1 | 1/2022 |
| WO | 2022029051 | A1 | 2/2022 |
| WO | 2022058395 | A1 | 3/2022 |
| WO | 2022068810 | A1 | 4/2022 |
| WO | 2022237666 | A1 | 11/2022 |
| WO | 2023109953 | A1 | 6/2023 |
| WO | 2023185732 | A1 | 10/2023 |
| WO | 2023231942 | A1 | 12/2023 |
| WO | 2024255879 | A1 | 12/2024 |
| WO | 2024255880 | A1 | 12/2024 |
| WO | 2025077815 | A | 4/2025 |

OTHER PUBLICATIONS

Yan et al. Construction of a synthetic phage-displayed Nanobody library with CDR3 regions randomized by trinucleotide cassettes for diagnostic applications, J. Translational Med. 12:343, 12 pages, 2014.*

Sela-Culang et al., The structural basis of antibody-antigen recognition, Front. Immunol. 4:302, 13 pages, Oct. 2013.*

Koenig et al., Mutational landscape of antibody variable domains reveals a switch modulating the interdomain conformational dynamics and antigen binding, Proc. Natl. Acad. Sci. USA, 114(4):E486-495, 2017.*

Luo et al., Protein scaffolds: antibody alternatives for cancer diagnosis and therapy, Royal Soc. Chem. Chem. Biol. 8:830-847, 2022.*

Vazquez-Lombardi et al., CHallenges and opportunities for non-antibody scaffold drugs, Drug Disc. Today, 20(10):1271-1283, Oct. 2015.*

Bruner et al., “Size exclusion HPLC method for the determination of acidic fibroblast growth factor in viscous formulations”, Journal of Pharmaceutical and Biomedical Analysis, 15 (1997) 1929-1935 [7 pages].

Goyon et al.: “Protocols for the analytical characterization of therapeutic monoclonal antibodies. I—Non-denaturing chromatographic techniques”: Journal of Chromatography B, 1058 (2017) 73-84 [15 pages].

Holland: “Development of a Highly Potent Bispecific Antibody Format Targeting the Novel Tumor-Specific Antigen CLDN18.2”, Doctorate Dissertation, submitted Nov. 11, 2014 [128 pages].

International Search Report and Written Opinion of PCT/CN2021/100870, dated Sep. 17, 2021, including translations. [21 pages].

International Search Report and Written Opinion of PCT/CN2021/121286, dated Jan. 6, 2022, including translations. [26 pages].

International Search Report and Written Opinion of PCT/CN2022/139637, dated Mar. 7, 2023, including translations. [26 pages].

International Search Report and Written Opinion of PCT/CN2023/084070 dated Jun. 25, 2023, including translations. [19 pages].

Jones : “Analysis of polypeptides and proteins”: Advanced Drug Delivery Reviews, 10 (1993) 29-90 [62 pages].

Kelley et al: “Weak Partitioning Chromatography for Anion Exchange Purification of Monoclonal Antibodies”: Biotechnology and Bioengineering, vol. 101, No. 3, 2008; pp. 553-566 [14 pages].

Minow et al: “Implementing a Fully Disposable MAb Manufacturing Facility, Solutions and Challenges”: BioProcess International 10(6), 2012: pp. 48-57 [7 pages].

Root et al. “Development of PF-06671008, a Highly Potent Anti-P-cadherin/Anti-CD3 Bispecific DART Molecule with Extended Half-Life for the Treatment of Cancer”. Antibodies (Basel). 2016; 5(1):6. [30 pages].

Rustandi et al: “Applications of CE SDS gel in development of biopharmaceutical antibody-based products”: Electrophoresis 2008, 29, 3612-3620 [9 pages].

(56) References Cited

OTHER PUBLICATIONS

Sahin et al: "Claudin-18 splice variant 2 is a pan-cancer target suitable for therapeutic antibody development", Clinical Cancer Research, vol. 14, No. 23, 2008, pp. 7624-7634.
Shahrokh et al.: "Approaches to Analysis of Aggregates and Demonstrating Mass Balance in Pharmaceutical Protein (Basic Fibroblast Growth Factor) Formulations", Journal of Pharmaceutical Sciences vol. 83, No. 12, 1994; pp. 1645-1650 [6 pages].
Singh et al: "Anti-claudin 18.2 antibody as new targeted therapy for advanced gastric cancer". J Hematol Oncol 10, 105 (2017). [5 pages].
Sluzky et al.: "Chromatographic Methods for Quantitative Analysis of Native, Denatured, and Aggregated Basic Fibroblast Growth Factor in Solution Formulations", Pharmaceutical Research, vol. 11, No. 4, 1994, 485-490 [6 pages].
Tugcu et al.: "Maximizing Productivity of Chromatography Steps for Purification of Monoclonal Antibodies": Biotechnology and Bioengineering, vol. 99, No. 3, 2008; pp. 599-613.
Türeci et al. "Claudin-18 gene structure, regulation, and expression is evolutionary conserved in mammals." Gene 481 (2011): 83-92. [10 pages].
U.S. Appl. No. 18/719,023, filed Jun. 12, 2024.
U.S. Appl. No. 18/850,651, filed Sep. 25, 2024.
Usami et al., "The effect of pH, hydrogen peroxide and temperature on the stability of human monoclonal antibody", Journal of Pharmaceutical and Biomedical Analysis 14 (1996): 1133-1140 [8 pages].
Yang et al.: "High resolution separation of recombinant monoclonal antibodies by size exclusion ultra-high performance liquid chromatography (SE-UHPLC)", Journal of Pharmaceutical and Biomedical Analysis 109 (2015) 52-61 [10 pages].
Zhu et al. Targeting CLDN18.2 by CD3 Bispecific and ADC Modalities for the Treatments of Gastric and Pancreatic Cancer. Sci Rep. 2019; 9(1):8420. [11 pages].
Darowski et al.,. "P329G-CAR-J: a novel Jurkat-NFAT-based CAR-T reporter system recognizing the P329G Fc mutation", Protein Engineering, Design and Selection, 2019, 12 pages.
Floris van Delft et al., Novel Linker-Payload (SYNtecan ET) based on Topoisomerase 1 Inhibitor Exatecan enables Potent ADCs with Promising In Vivo Efficacy, on Par with Deruxtecan Technology. Synaffix poster, World ADC meeting, Sep. 2020. [retrieved online from https://synaffix.com/wp-content/uploads/2021/01/WADC_virtual2020_poster_exatecan.pdf], 1 page.
Jiang et al., Claudin18.2-specific chimeric antigen receptor engineered T cells for the treatment of gastric cancer, J Natl Cancer Inst (2019) 111(4):djy134, 10 pages.
Xu et al., Advances of CLDN18.2 protein in the therapy of malignant tumors. Chinese Journal of Clinical Oncology, 2019, 46(6): pp. 311-315, English Abstract Only.
Yu et al., Antibody-Drug Conjugates Targeting the Human Epidermal Growth Factor Receptor Family in Cancers. Frontiers in molecular biosciences, 2022, vol. 9, Article 847835, 11 pages.
U.S. Appl. No. 19/376,098, filed Oct. 31, 2025. [100 pages].

* cited by examiner

| | Zmab | hz69H9 | HB37A6 | IgG1 isotype |
|---|---|---|---|---|
| EC50 | 2.668 | 2.897 | 2.855 | ~ 110483742 |

SEQUENCE LISTING

<160> NUMBER OF SEQ ID NOS: 94

<210> SEQ ID NO 1
<211> LENGTH: 10
<212> TYPE: PRT
<213> ORGANISM: Artificial
<220> FEATURE:
<223> OTHER INFORMATION: Synthetic peptide

<400> SEQUENCE: 1

```
Gly Phe Thr Phe Ser Ser Tyr Val Met Ser
1               5                   10
```

<210> SEQ ID NO 2
<211> LENGTH: 17
<212> TYPE: PRT
<213> ORGANISM: Artificial
<220> FEATURE:
<223> OTHER INFORMATION: Synthetic peptide

<400> SEQUENCE: 2

```
Thr Ile Ser His Ser Gly Gly Ser Thr Tyr Tyr Ala Asp Ser Val Lys
1               5                   10                  15

Gly
```

<210> SEQ ID NO 3
<211> LENGTH: 13
<212> TYPE: PRT
<213> ORGANISM: Artificial
<220> FEATURE:
<223> OTHER INFORMATION: Synthetic peptide

<400> SEQUENCE: 3

```
Asp Ala Pro Tyr Tyr Asp Ile Leu Thr Gly Tyr Arg Tyr
1               5                   10
```

<210> SEQ ID NO 4
<211> LENGTH: 122
<212> TYPE: PRT
<213> ORGANISM: Artificial
<220> FEATURE:
<223> OTHER INFORMATION: Synthetic peptide

<400> SEQUENCE: 4

```
Glu Val Gln Leu Leu Asp Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Met Ser Trp Val Arg Gln Ala Pro Gly Lys Gly Leu Asn Trp Val
        35                  40                  45

Ser Thr Ile Ser His Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Asp Ala Pro Tyr Tyr Asp Ile Leu Thr Gly Tyr Arg Tyr Trp
            100                 105                 110

Gly Gln Gly Thr Leu Val Thr Val Ser Ser
        115                 120
```

<210> SEQ ID NO 5

<211> LENGTH: 330
<212> TYPE: PRT
<213> ORGANISM: Artificial
<220> FEATURE:
<223> OTHER INFORMATION: Synthetic peptide

<400> SEQUENCE: 5

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Ala Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 6
<211> LENGTH: 11
<212> TYPE: PRT
<213> ORGANISM: Artificial
<220> FEATURE:
<223> OTHER INFORMATION: Synthetic peptide

<400> SEQUENCE: 6

Arg Ala Ser Gln Ser Ile Ser Ser Trp Leu Ala
1 5 10

<210> SEQ ID NO 7
<211> LENGTH: 7
<212> TYPE: PRT
<213> ORGANISM: Artificial
<220> FEATURE:
<223> OTHER INFORMATION: Synthetic peptide

<400> SEQUENCE: 7

Lys Ala Ser Ser Leu Glu Ser
1 5

<210> SEQ ID NO 8
<211> LENGTH: 9
<212> TYPE: PRT
<213> ORGANISM: Artificial
<220> FEATURE:
<223> OTHER INFORMATION: Synthetic peptide

<400> SEQUENCE: 8

Gln Gln Tyr Asn Ser Tyr Ser Tyr Thr
1 5

<210> SEQ ID NO 9
<211> LENGTH: 107
<212> TYPE: PRT
<213> ORGANISM: Artificial
<220> FEATURE:
<223> OTHER INFORMATION: Synthetic peptide

<400> SEQUENCE: 9

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Ser Trp
20 25 30

Leu Ala Trp Tyr Gln Gln Lys Pro Gly Lys Ala Pro Lys Leu Leu Ile
35 40 45

Tyr Lys Ala Ser Ser Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Tyr Asn Ser Tyr Ser Tyr
85 90 95

Thr Phe Gly Gln Gly Thr Lys Leu Glu Ile Lys
100 105

<210> SEQ ID NO 10
<211> LENGTH: 107
<212> TYPE: PRT
<213> ORGANISM: Artificial
<220> FEATURE:
<223> OTHER INFORMATION: Synthetic peptide

<400> SEQUENCE: 10

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln

```
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 11
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 11

Lys Ser Ser Gln Ser Leu Leu Xaa Gly Gly Asn Gln Lys Asn Tyr Leu
1               5                   10                  15

Thr


<210> SEQ ID NO 12
<211> LENGTH: 10
<212> TYPE: PRT
<213> ORGANISM: Artificial
<220> FEATURE:
<223> OTHER INFORMATION: Synthetic peptide

<400> SEQUENCE: 12

Gly Tyr Ser Phe Ser Ser Tyr Asn Ile His
1               5                   10


<210> SEQ ID NO 13
<211> LENGTH: 17
<212> TYPE: PRT
<213> ORGANISM: Artificial
<220> FEATURE:
<223> OTHER INFORMATION: Synthetic peptide

<400> SEQUENCE: 13

Tyr Ile Ala Pro Phe Asn Gly Asp Ser Arg Tyr Asn Gln Lys Phe Lys
1               5                   10                  15

Gly


<210> SEQ ID NO 14
<211> LENGTH: 9
<212> TYPE: PRT
<213> ORGANISM: Artificial
<220> FEATURE:
<223> OTHER INFORMATION: Synthetic peptide

<400> SEQUENCE: 14

Leu Asn Arg Gly Asn Ser Leu Asp Tyr
1               5


<210> SEQ ID NO 15
<211> LENGTH: 118
<212> TYPE: PRT
<213> ORGANISM: Artificial
```

<220> FEATURE:
<223> OTHER INFORMATION: Synthetic peptide

<400> SEQUENCE: 15

Glu Val Gln Leu Gln Gln Ser Gly Pro Glu Leu Met Lys Pro Gly Ala
1               5                   10                  15

Ser Val Lys Ile Ser Cys Lys Ala Thr Gly Tyr Ser Phe Ser Ser Tyr
            20                  25                  30

Asn Ile His Trp Val Lys Gln Ser His Gly Lys Ser Leu Glu Trp Ile
        35                  40                  45

Gly Tyr Ile Ala Pro Phe Asn Gly Asp Ser Arg Tyr Asn Gln Lys Phe
    50                  55                  60

Lys Gly Lys Ala Thr Val Thr Val Asp Lys Ser Ser Ser Thr Ala Tyr
65                  70                  75                  80

Met His Leu Ser Ser Leu Thr Ser Glu Asp Ser Ala Val Tyr Tyr Cys
                85                  90                  95

Gly Arg Leu Asn Arg Gly Asn Ser Leu Asp Tyr Trp Gly Gln Gly Thr
            100                 105                 110

Ser Leu Thr Val Ser Ser
        115

<210> SEQ ID NO 16
<211> LENGTH: 17
<212> TYPE: PRT
<213> ORGANISM: Artificial
<220> FEATURE:
<223> OTHER INFORMATION: Synthetic peptide

<400> SEQUENCE: 16

Lys Ser Ser Gln Ser Leu Phe Asn Ser Gly Asn Gln Arg Asn Tyr Leu
1               5                   10                  15

Thr

<210> SEQ ID NO 17
<211> LENGTH: 7
<212> TYPE: PRT
<213> ORGANISM: Artificial
<220> FEATURE:
<223> OTHER INFORMATION: Synthetic peptide

<400> SEQUENCE: 17

Trp Ala Ser Thr Arg Glu Ser
1               5

<210> SEQ ID NO 18
<211> LENGTH: 9
<212> TYPE: PRT
<213> ORGANISM: Artificial
<220> FEATURE:
<223> OTHER INFORMATION: Synthetic peptide

<400> SEQUENCE: 18

Gln Asn Asn Tyr Ile Tyr Pro Leu Thr
1               5

<210> SEQ ID NO 19
<211> LENGTH: 113
<212> TYPE: PRT
<213> ORGANISM: Artificial
<220> FEATURE:
<223> OTHER INFORMATION: Synthetic peptide

<400> SEQUENCE: 19

Asp Ile Val Met Thr Gln Ser Pro Ser Ser Leu Thr Val Thr Ala Gly
1 5 10 15

Glu Lys Val Thr Met Ser Cys Lys Ser Ser Gln Ser Leu Phe Asn Ser
20 25 30

Gly Asn Gln Arg Asn Tyr Leu Thr Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Thr Gly Ser Gly Ser Gly Thr Asp Phe Thr Leu Thr
65 70 75 80

Ile Ser Ser Val Gln Ala Glu Asp Leu Ala Phe Tyr Tyr Cys Gln Asn
85 90 95

Asn Tyr Ile Tyr Pro Leu Thr Phe Gly Ala Gly Thr Lys Leu Glu Leu
100 105 110

Lys

<210> SEQ ID NO 20
<211> LENGTH: 17
<212> TYPE: PRT
<213> ORGANISM: Artificial
<220> FEATURE:
<223> OTHER INFORMATION: Synthetic peptide

<400> SEQUENCE: 20

Tyr Ile Ala Pro Phe Gln Gly Asp Ser Arg Tyr Asn Gln Lys Phe Lys
1 5 10 15

Gly

<210> SEQ ID NO 21
<211> LENGTH: 118
<212> TYPE: PRT
<213> ORGANISM: Artificial
<220> FEATURE:
<223> OTHER INFORMATION: Synthetic peptide

<400> SEQUENCE: 21

Gln Val Gln Leu Val Gln Ser Gly Ala Glu Val Lys Lys Pro Gly Ser
1 5 10 15

Ser Val Lys Val Ser Cys Lys Ala Ser Gly Tyr Ser Phe Ser Ser Tyr
20 25 30

Asn Ile His Trp Val Arg Gln Ala Pro Gly Gln Gly Leu Glu Trp Met
35 40 45

Gly Tyr Ile Ala Pro Phe Gln Gly Asp Ser Arg Tyr Asn Gln Lys Phe
50 55 60

Lys Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Leu Asn Arg Gly Asn Ser Leu Asp Tyr Trp Gly Gln Gly Thr
100 105 110

Leu Val Thr Val Ser Ser
115

<210> SEQ ID NO 22
<211> LENGTH: 113
<212> TYPE: PRT
<213> ORGANISM: Artificial
<220> FEATURE:

<223> OTHER INFORMATION: Synthetic peptide

<400> SEQUENCE: 22

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Leu Phe Asn Ser
20 25 30

Gly Asn Gln Arg Asn Tyr Leu Thr Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Asn
85 90 95

Asn Tyr Ile Tyr Pro Leu Thr Phe Gly Gly Gly Thr Lys Val Glu Ile
100 105 110

Lys

<210> SEQ ID NO 23
<211> LENGTH: 10
<212> TYPE: PRT
<213> ORGANISM: Artificial
<220> FEATURE:
<223> OTHER INFORMATION: Synthetic peptide

<400> SEQUENCE: 23

Gly Phe Ser Phe Ser Asp Tyr Gly Met His
1 5 10

<210> SEQ ID NO 24
<211> LENGTH: 17
<212> TYPE: PRT
<213> ORGANISM: Artificial
<220> FEATURE:
<223> OTHER INFORMATION: Synthetic peptide

<400> SEQUENCE: 24

Tyr Ile Asn Ser Gly Ser Arg Thr Leu Tyr Tyr Ala Asp Thr Val Lys
1 5 10 15

Gly

<210> SEQ ID NO 25
<211> LENGTH: 10
<212> TYPE: PRT
<213> ORGANISM: Artificial
<220> FEATURE:
<223> OTHER INFORMATION: Synthetic peptide

<400> SEQUENCE: 25

Asn Ala Tyr Tyr Gly Asn Ala Met Asp Tyr
1 5 10

<210> SEQ ID NO 26
<211> LENGTH: 119
<212> TYPE: PRT
<213> ORGANISM: Artificial
<220> FEATURE:
<223> OTHER INFORMATION: Synthetic peptide

<400> SEQUENCE: 26

Glu Val Gln Leu Val Glu Ser Gly Gly Gly Leu Val Lys Pro Gly Gly

```
1               5                   10                  15

Ser Leu Lys Leu Ser Cys Ala Ala Ser Gly Phe Ser Phe Ser Asp Tyr
            20                  25                  30

Gly Met His Trp Val Arg Gln Ala Pro Glu Lys Gly Leu Glu Trp Ile
        35                  40                  45

Ala Tyr Ile Asn Ser Gly Ser Arg Thr Leu Tyr Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Glu Thr Ala Met Tyr Tyr Cys
                85                  90                  95

Thr Arg Asn Ala Tyr Tyr Gly Asn Ala Met Asp Tyr Trp Gly Gln Gly
            100                 105                 110

Thr Ser Val Thr Val Ser Ser
        115


<210> SEQ ID NO 27
<211> LENGTH: 119
<212> TYPE: PRT
<213> ORGANISM: Artificial
<220> FEATURE:
<223> OTHER INFORMATION: Synthetic peptide

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Tyr
            20                  25                  30

Gly Met His Trp Val Arg Gln Ala Pro Gly Lys Gly Leu Glu Trp Val
        35                  40                  45

Ser Tyr Ile Asn Ser Gly Ser Arg Thr Leu Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Asn Ala Tyr Tyr Gly Asn Ala Met Asp Tyr Trp Gly Gln Gly
            100                 105                 110

Thr Leu Val Thr Val Ser Ser
        115


<210> SEQ ID NO 28
<211> LENGTH: 17
<212> TYPE: PRT
<213> ORGANISM: Artificial
<220> FEATURE:
<223> OTHER INFORMATION: Synthetic peptide

<400> SEQUENCE: 28

Lys Ser Ser Gln Ser Leu Leu Asn Ser Gly Asn Gln Arg Asn Tyr Leu
1               5                   10                  15

Thr


<210> SEQ ID NO 29
<211> LENGTH: 7
<212> TYPE: PRT
<213> ORGANISM: Artificial
<220> FEATURE:
<223> OTHER INFORMATION: Synthetic peptide
```

<400> SEQUENCE: 29

Trp Ser Ser Thr Arg Gly Ser
1 5

<210> SEQ ID NO 30
<211> LENGTH: 9
<212> TYPE: PRT
<213> ORGANISM: Artificial
<220> FEATURE:
<223> OTHER INFORMATION: Synthetic peptide

<400> SEQUENCE: 30

Gln Asn Val Tyr Tyr Tyr Pro Phe Thr
1 5

<210> SEQ ID NO 31
<211> LENGTH: 113
<212> TYPE: PRT
<213> ORGANISM: Artificial
<220> FEATURE:
<223> OTHER INFORMATION: Synthetic peptide

<400> SEQUENCE: 31

Asp Ile Gln Met Thr Gln Ser Pro Ser Ser Leu Thr Val Thr Ala Gly
1 5 10 15

Glu Lys Val Thr Met Ser Cys Lys Ser Ser Gln Ser Leu Leu Asn Ser
20 25 30

Gly Asn Gln Arg Asn Tyr Leu Thr Trp Tyr Gln Gln Ile Pro Gly Gln
35 40 45

Pro Pro Lys Leu Leu Ile Tyr Trp Ser Ser Thr Arg Gly Ser Gly Val
50 55 60

Pro Asp Arg Phe Thr Gly Ser Gly Ser Gly Thr Asp Phe Thr Leu Thr
65 70 75 80

Ile Ser Ser Val Gln Ala Glu Asp Leu Ala Val Tyr Phe Cys Gln Asn
85 90 95

Val Tyr Tyr Tyr Pro Phe Thr Phe Gly Ser Gly Thr Arg Leu Glu Val
100 105 110

Lys

<210> SEQ ID NO 32
<211> LENGTH: 113
<212> TYPE: PRT
<213> ORGANISM: Artificial
<220> FEATURE:
<223> OTHER INFORMATION: Synthetic peptide

<400> SEQUENCE: 32

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Leu Leu Asn Ser
20 25 30

Gly Asn Gln Arg Asn Tyr Leu Thr Trp Tyr Gln Gln Lys Pro Gly Gln
35 40 45

Pro Pro Lys Leu Leu Ile Tyr Trp Ser Ser Thr Arg Gly Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Asn
85 90 95

Val Tyr Tyr Tyr Pro Phe Thr Phe Gly Gln Gly Thr Arg Leu Glu Ile
100 105 110

Lys

<210> SEQ ID NO 33
<211> LENGTH: 11
<212> TYPE: PRT
<213> ORGANISM: Artificial
<220> FEATURE:
<223> OTHER INFORMATION: Synthetic peptide

<400> SEQUENCE: 33

Gly Tyr Ser Ile Thr Ser Gly Tyr Gly Trp Asn
1 5 10

<210> SEQ ID NO 34
<211> LENGTH: 16
<212> TYPE: PRT
<213> ORGANISM: Artificial
<220> FEATURE:
<223> OTHER INFORMATION: Synthetic peptide

<400> SEQUENCE: 34

Tyr Ile His Phe Ser Gly Ser Thr Asn Tyr Asn Pro Ser Leu Lys Ser
1 5 10 15

<210> SEQ ID NO 35
<211> LENGTH: 9
<212> TYPE: PRT
<213> ORGANISM: Artificial
<220> FEATURE:
<223> OTHER INFORMATION: Synthetic peptide

<400> SEQUENCE: 35

Ser Gly Lys Gly Asn Ala Met Asp Tyr
1 5

<210> SEQ ID NO 36
<211> LENGTH: 118
<212> TYPE: PRT
<213> ORGANISM: Artificial
<220> FEATURE:
<223> OTHER INFORMATION: Synthetic peptide

<400> SEQUENCE: 36

Gln Val Gln Leu Lys Glu Ser Gly Pro Asp Leu Val Lys Pro Ser Gln
1 5 10 15

Ser Leu Ser Leu Thr Cys Thr Val Thr Gly Tyr Ser Ile Thr Ser Gly
20 25 30

Tyr Gly Trp Asn Trp Ile Arg Gln Phe Pro Gly Asn Lys Leu Glu Trp
35 40 45

Met Gly Tyr Ile His Phe Ser Gly Ser Thr Asn Tyr Asn Pro Ser Leu
50 55 60

Lys Ser Arg Ile Ser Ile Thr Arg Asp Thr Ser Lys Asn Gln Phe Phe
65 70 75 80

Leu Gln Leu Asn Ser Val Thr Thr Glu Asp Thr Ala Thr Tyr Tyr Cys
85 90 95

Ala Arg Ser Gly Lys Gly Asn Ala Met Asp Tyr Trp Gly Gln Gly Thr
100 105 110

Ser Val Thr Val Ser Ser
115

<210> SEQ ID NO 37
<211> LENGTH: 118
<212> TYPE: PRT
<213> ORGANISM: Artificial
<220> FEATURE:
<223> OTHER INFORMATION: Synthetic peptide

<400> SEQUENCE: 37

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Gly
            20                  25                  30

Tyr Gly Trp Asn Trp Ile Arg Gln Pro Pro Gly Lys Gly Leu Glu Trp
        35                  40                  45

Ile Gly Tyr Ile His Phe Ser Gly Ser Thr Asn Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Gly Lys Gly Asn Ala Met Asp Tyr Trp Gly Gln Gly Thr
            100                 105                 110

Leu Val Thr Val Ser Ser
        115
```

<210> SEQ ID NO 38
<211> LENGTH: 17
<212> TYPE: PRT
<213> ORGANISM: Artificial
<220> FEATURE:
<223> OTHER INFORMATION: Synthetic peptide

<400> SEQUENCE: 38

```
Lys Ser Ser Gln Ser Leu Leu Asn Ser Gly Asn Gln Lys Asn Tyr Leu
1               5                   10                  15

Thr
```

<210> SEQ ID NO 39
<211> LENGTH: 9
<212> TYPE: PRT
<213> ORGANISM: Artificial
<220> FEATURE:
<223> OTHER INFORMATION: Synthetic peptide

<400> SEQUENCE: 39

```
Gln Asn Asp Tyr Tyr Phe Pro Phe Thr
1               5
```

<210> SEQ ID NO 40
<211> LENGTH: 113
<212> TYPE: PRT
<213> ORGANISM: Artificial
<220> FEATURE:
<223> OTHER INFORMATION: Synthetic peptide

<400> SEQUENCE: 40

```
Asp Ile Gln Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
```

```
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Val Ile Asn Met Gln Ala Glu Asp Leu Ala Leu Tyr Tyr Cys Gln Asn
                85                  90                  95

Asp Tyr Tyr Phe Pro Phe Thr Phe Gly Ser Gly Thr Lys Leu Glu Ile
            100                 105                 110

Lys


<210> SEQ ID NO 41
<211> LENGTH: 113
<212> TYPE: PRT
<213> ORGANISM: Artificial
<220> FEATURE:
<223> OTHER INFORMATION: Synthetic peptide

<400> SEQUENCE: 41

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Tyr Phe Pro Phe Thr Phe Gly Gly Gly Thr Lys Val Glu Ile
            100                 105                 110

Lys


<210> SEQ ID NO 42
<211> LENGTH: 10
<212> TYPE: PRT
<213> ORGANISM: Artificial
<220> FEATURE:
<223> OTHER INFORMATION: Synthetic peptide

<400> SEQUENCE: 42

Gly Tyr Thr Phe Thr Lys Tyr Ile Ile Gln
1               5                   10


<210> SEQ ID NO 43
<211> LENGTH: 17
<212> TYPE: PRT
<213> ORGANISM: Artificial
<220> FEATURE:
<223> OTHER INFORMATION: Synthetic peptide

<400> SEQUENCE: 43

Tyr Ile Asn Pro Tyr Asn Asp Asp Thr Lys Tyr Asn Glu Lys Phe Lys
1               5                   10                  15

Gly


<210> SEQ ID NO 44
```

<211> LENGTH: 9
<212> TYPE: PRT
<213> ORGANISM: Artificial
<220> FEATURE:
<223> OTHER INFORMATION: Synthetic peptide

<400> SEQUENCE: 44

Thr Tyr Tyr Gly Asn Ser Phe Pro Asn
1 5

<210> SEQ ID NO 45
<211> LENGTH: 118
<212> TYPE: PRT
<213> ORGANISM: Artificial
<220> FEATURE:
<223> OTHER INFORMATION: Synthetic peptide

<400> SEQUENCE: 45

Glu Val Gln Leu Gln Gln Ser Val Pro Glu Leu Val Lys Pro Gly Ala
1 5 10 15

Ser Val Arg Met Ser Cys Lys Ala Ser Gly Tyr Thr Phe Thr Lys Tyr
20 25 30

Ile Ile Gln Trp Val Lys Gln Lys Pro Gly Gln Gly Leu Glu Trp Ile
35 40 45

Ala Tyr Ile Asn Pro Tyr Asn Asp Asp Thr Lys Tyr Asn Glu Lys Phe
50 55 60

Lys Gly Lys Ala Thr Leu Thr Ser Asp Lys Ser Ala Ser Thr Ala Tyr
65 70 75 80

Met Glu Leu Ser Ser Leu Thr Ser Glu Asp Ser Ala Val Tyr Tyr Cys
85 90 95

Ala Thr Thr Tyr Tyr Gly Asn Ser Phe Pro Asn Trp Gly Gln Gly Thr
100 105 110

Leu Val Thr Val Ser Ala
115

<210> SEQ ID NO 46
<211> LENGTH: 9
<212> TYPE: PRT
<213> ORGANISM: Artificial
<220> FEATURE:
<223> OTHER INFORMATION: Synthetic peptide

<400> SEQUENCE: 46

Gln Asn Asp Tyr Ser Phe Pro Phe Thr
1 5

<210> SEQ ID NO 47
<211> LENGTH: 113
<212> TYPE: PRT
<213> ORGANISM: Artificial
<220> FEATURE:
<223> OTHER INFORMATION: Synthetic peptide

<400> SEQUENCE: 47

Asp Ile Val Met Thr Gln Ser Pro Ser Ser Leu Thr Val Thr Ala Gly
1 5 10 15

Glu Arg Val Thr Met Thr Cys Lys Ser Ser Gln Ser Leu Leu Asn Ser
20 25 30

Gly Asn Gln Lys Asn Tyr Leu Thr Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Thr Gly Ser Gly Ser Gly Thr Asp Phe Thr Leu Thr
65 70 75 80

Ile Ser Ser Leu Gln Ser Glu Asp Leu Ala Val Tyr Phe Cys Gln Asn
85 90 95

Asp Tyr Ser Phe Pro Phe Thr Phe Gly Ser Gly Thr Lys Leu Glu Ile
100 105 110

Lys

<210> SEQ ID NO 48
<211> LENGTH: 118
<212> TYPE: PRT
<213> ORGANISM: Artificial
<220> FEATURE:
<223> OTHER INFORMATION: Synthetic peptide

<400> SEQUENCE: 48

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Lys Tyr
20 25 30

Ile Ile Gln Trp Val Arg Gln Ala Pro Gly Gln Arg Leu Glu Trp Met
35 40 45

Gly Tyr Ile Asn Pro Tyr Asn Asp Asp Thr Lys Tyr Asn Glu Lys Phe
50 55 60

Lys Gly Arg Val Thr Ile Thr Arg Asp Thr Ser Ala Ser Thr Ala Tyr
65 70 75 80

Met Glu Leu Ser Ser Leu Arg Ser Glu Asp Met Ala Val Tyr Tyr Cys
85 90 95

Ala Arg Thr Tyr Tyr Gly Asn Ser Phe Pro Asn Trp Gly Gln Gly Thr
100 105 110

Leu Val Thr Val Ser Ser
115

<210> SEQ ID NO 49
<211> LENGTH: 113
<212> TYPE: PRT
<213> ORGANISM: Artificial
<220> FEATURE:
<223> OTHER INFORMATION: Synthetic peptide

<400> SEQUENCE: 49

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Leu Leu Asn Ser
20 25 30

Gly Asn Gln Lys Asn Tyr Leu Thr Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Asn
85 90 95

Asp Tyr Ser Phe Pro Phe Thr Phe Gly Gly Gly Thr Lys Val Glu Ile
100 105 110

Lys

<210> SEQ ID NO 50
<211> LENGTH: 10
<212> TYPE: PRT
<213> ORGANISM: Artificial
<220> FEATURE:
<223> OTHER INFORMATION: Synthetic peptide

<400> SEQUENCE: 50

Gly Phe Ser Leu Thr Asp Tyr Gly Val Ser
1               5                   10

<210> SEQ ID NO 51
<211> LENGTH: 16
<212> TYPE: PRT
<213> ORGANISM: Artificial
<220> FEATURE:
<223> OTHER INFORMATION: Synthetic peptide

<400> SEQUENCE: 51

Val Met Trp Gly Gly Gly Asn Thr Tyr Tyr Asn Ser Ala Leu Lys Ser
1               5                   10                  15

<210> SEQ ID NO 52
<211> LENGTH: 10
<212> TYPE: PRT
<213> ORGANISM: Artificial
<220> FEATURE:
<223> OTHER INFORMATION: Synthetic peptide

<400> SEQUENCE: 52

Gln Arg Tyr Gly Gly Asn Ala Met Asp Tyr
1               5                   10

<210> SEQ ID NO 53
<211> LENGTH: 118
<212> TYPE: PRT
<213> ORGANISM: Artificial
<220> FEATURE:
<223> OTHER INFORMATION: Synthetic peptide

<400> SEQUENCE: 53

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asp Tyr
            20                  25                  30

Gly Val Ser Trp Ile Arg Gln Pro Pro Gly Lys Gly Leu Glu Trp Leu
        35                  40                  45

Gly Val Met Trp Gly Gly Gly Asn Thr Tyr Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Ser Asp Asp Thr Ala Met Tyr Tyr Cys Ala
                85                  90                  95

Lys Gln Arg Tyr Gly Gly Asn Ala Met Asp Tyr Trp Gly Gln Gly Thr
            100                 105                 110

Ser Val Thr Val Ser Ser
        115

<210> SEQ ID NO 54
<211> LENGTH: 9
<212> TYPE: PRT
<213> ORGANISM: Artificial
<220> FEATURE:

<223> OTHER INFORMATION: Synthetic peptide

<400> SEQUENCE: 54

Gln Asn Ser Tyr Phe Tyr Pro Phe Thr
1 5

<210> SEQ ID NO 55
<211> LENGTH: 113
<212> TYPE: PRT
<213> ORGANISM: Artificial
<220> FEATURE:
<223> OTHER INFORMATION: Synthetic peptide

<400> SEQUENCE: 55

Asp Ile Gln Met Thr Gln Ser Pro Ser Ser Leu Thr Val Thr Ala Gly
1 5 10 15

Glu Lys Val Thr Met Ser Cys Lys Ser Ser Gln Ser Leu Leu Asn Ser
20 25 30

Gly Asn Gln Arg Asn Tyr Leu Thr Trp Tyr Gln Gln Ile Pro Gly Gln
35 40 45

Pro Pro Lys Leu Leu Ile Tyr Trp Ala Ser Thr Arg Glu Ser Gly Val
50 55 60

Pro Asn Arg Phe Thr Gly Ser Gly Ser Gly Ala Glu Phe Thr Leu Thr
65 70 75 80

Ile Ser Ser Val Gln Thr Glu Asp Leu Ala Val Tyr Tyr Cys Gln Asn
85 90 95

Ser Tyr Phe Tyr Pro Phe Thr Phe Gly Ala Gly Thr Lys Leu Glu Leu
100 105 110

Lys

<210> SEQ ID NO 56
<211> LENGTH: 118
<212> TYPE: PRT
<213> ORGANISM: Artificial
<220> FEATURE:
<223> OTHER INFORMATION: Synthetic peptide

<400> SEQUENCE: 56

Gln Val Gln Leu Gln Glu Ser Gly Pro Gly Leu Val Lys Pro Ser Glu
1 5 10 15

Thr Leu Ser Leu Thr Cys Thr Val Ser Gly Phe Ser Leu Thr Asp Tyr
20 25 30

Gly Val Ser Trp Ile Arg Gln Pro Pro Gly Lys Gly Leu Glu Trp Ile
35 40 45

Gly Val Met Trp Gly Gly Gly Asn Thr Tyr Tyr Asn Ser Ala Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Gln Arg Tyr Gly Gly Asn Ala Met Asp Tyr Trp Gly Gln Gly Thr
100 105 110

Leu Val Thr Val Ser Ser
115

<210> SEQ ID NO 57
<211> LENGTH: 113
<212> TYPE: PRT
<213> ORGANISM: Artificial

<220> FEATURE:
<223> OTHER INFORMATION: Synthetic peptide

<400> SEQUENCE: 57

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Arg Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Ser Tyr Phe Tyr Pro Phe Thr Phe Gly Gly Gly Thr Lys Val Glu Ile
            100                 105                 110

Lys
```

<210> SEQ ID NO 58
<211> LENGTH: 10
<212> TYPE: PRT
<213> ORGANISM: Artificial
<220> FEATURE:
<223> OTHER INFORMATION: Synthetic peptide

<400> SEQUENCE: 58

```
Gly Phe Thr Phe Ser Asp Tyr Gly Met Ala
1               5                   10
```

<210> SEQ ID NO 59
<211> LENGTH: 17
<212> TYPE: PRT
<213> ORGANISM: Artificial
<220> FEATURE:
<223> OTHER INFORMATION: Synthetic peptide

<400> SEQUENCE: 59

```
Phe Ile Asn Asn Leu Ala Tyr Ser Ile Tyr Tyr Val Asp Thr Val Thr
1               5                   10                  15

Gly
```

<210> SEQ ID NO 60
<211> LENGTH: 9
<212> TYPE: PRT
<213> ORGANISM: Artificial
<220> FEATURE:
<223> OTHER INFORMATION: Synthetic peptide

<400> SEQUENCE: 60

```
Phe Thr Thr Gly Asn Val Met Asp Tyr
1               5
```

<210> SEQ ID NO 61
<211> LENGTH: 118
<212> TYPE: PRT
<213> ORGANISM: Artificial
<220> FEATURE:
<223> OTHER INFORMATION: Synthetic peptide

<400> SEQUENCE: 61

```
Glu Val Met Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Asp Tyr
            20                  25                  30

Gly Met Ala Trp Val Arg Gln Ala Pro Gly Lys Gly Pro Glu Trp Val
        35                  40                  45

Ala Phe Ile Asn Asn Leu Ala Tyr Ser Ile Tyr Tyr Val Asp Thr Val
    50                  55                  60

Thr Gly Arg Phe Thr Ile Ser Arg Glu Asn Ala Lys Asp Thr Leu Tyr
65                  70                  75                  80

Leu Glu Met Ser Ser Leu Arg Ser Glu Asp Thr Ala Leu Tyr Tyr Cys
                85                  90                  95

Ala Arg Phe Thr Thr Gly Asn Val Met Asp Tyr Trp Gly Gln Gly Thr
            100                 105                 110

Ser Val Thr Val Ser Ser
        115


<210> SEQ ID NO 62
<211> LENGTH: 17
<212> TYPE: PRT
<213> ORGANISM: Artificial
<220> FEATURE:
<223> OTHER INFORMATION: Synthetic peptide

<400> SEQUENCE: 62

Lys Ser Ser Gln Ser Leu Leu Asn Gly Gly Asn Gln Lys Asn Tyr Leu
1               5                   10                  15

Thr


<210> SEQ ID NO 63
<211> LENGTH: 7
<212> TYPE: PRT
<213> ORGANISM: Artificial
<220> FEATURE:
<223> OTHER INFORMATION: Synthetic peptide

<400> SEQUENCE: 63

Trp Ser Ser Thr Arg Glu Ser
1               5


<210> SEQ ID NO 64
<211> LENGTH: 9
<212> TYPE: PRT
<213> ORGANISM: Artificial
<220> FEATURE:
<223> OTHER INFORMATION: Synthetic peptide

<400> SEQUENCE: 64

Gln Asn Ser Tyr Ser Tyr Pro Leu Thr
1               5


<210> SEQ ID NO 65
<211> LENGTH: 113
<212> TYPE: PRT
<213> ORGANISM: Artificial
<220> FEATURE:
<223> OTHER INFORMATION: Synthetic peptide

<400> SEQUENCE: 65

Asp Ile Val Met Thr Gln Ser Pro Ser Ser Leu Thr Val Thr Ala Gly
1               5                   10                  15

Glu Lys Val Thr Met Thr Cys Lys Ser Ser Gln Ser Leu Leu Asn Gly
```

```
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ser Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Thr Ser Val Gln Ala Glu Asp Leu Ala Val Tyr Tyr Cys Gln Asn
                85                  90                  95

Ser Tyr Ser Tyr Pro Leu Thr Phe Gly Ser Gly Thr Lys Leu Glu Leu
            100                 105                 110

Lys


<210> SEQ ID NO 66
<211> LENGTH: 118
<212> TYPE: PRT
<213> ORGANISM: Artificial
<220> FEATURE:
<223> OTHER INFORMATION: Synthetic peptide

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met Ala Trp Val Arg Gln Ala Pro Gly Lys Gly Leu Glu Trp Val
        35                  40                  45

Ala Phe Ile Asn Asn Leu Ala Tyr Ser Ile Tyr Tyr Val Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Phe Thr Thr Gly Asn Val Met Asp Tyr Trp Gly Gln Gly Thr
            100                 105                 110

Leu Val Thr Val Ser Ser
        115


<210> SEQ ID NO 67
<211> LENGTH: 17
<212> TYPE: PRT
<213> ORGANISM: Artificial
<220> FEATURE:
<223> OTHER INFORMATION: Synthetic peptide

<400> SEQUENCE: 67

Lys Ser Ser Gln Ser Leu Leu Gln Gly Gly Asn Gln Lys Asn Tyr Leu
1               5                   10                  15

Thr


<210> SEQ ID NO 68
<211> LENGTH: 113
<212> TYPE: PRT
<213> ORGANISM: Artificial
<220> FEATURE:
<223> OTHER INFORMATION: Synthetic peptide

<400> SEQUENCE: 68

Asp Ile Val Met Thr Gln Ser Pro Asp Ser Leu Ala Val Ser Leu Gly
```

1 5 10 15

Glu Arg Ala Thr Ile Asn Cys Lys Ser Ser Gln Ser Leu Leu Gln Gly
20 25 30

Gly Asn Gln Lys Asn Tyr Leu Thr Trp Tyr Gln Gln Lys Pro Gly Gln
35 40 45

Pro Pro Lys Leu Leu Ile Tyr Trp Ser Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Asn
85 90 95

Ser Tyr Ser Tyr Pro Leu Thr Phe Gly Gly Gly Thr Lys Val Glu Ile
100 105 110

Lys

<210> SEQ ID NO 69
<211> LENGTH: 10
<212> TYPE: PRT
<213> ORGANISM: Artificial
<220> FEATURE:
<223> OTHER INFORMATION: Synthetic peptide

<400> SEQUENCE: 69

Gly Tyr Ser Phe Thr Thr Tyr Trp Met His
1 5 10

<210> SEQ ID NO 70
<211> LENGTH: 17
<212> TYPE: PRT
<213> ORGANISM: Artificial
<220> FEATURE:
<223> OTHER INFORMATION: Synthetic peptide

<400> SEQUENCE: 70

Leu Ile Asp Pro Ser Asp Ser Glu Thr Arg Leu Asn Gln Lys Phe Lys
1 5 10 15

Asp

<210> SEQ ID NO 71
<211> LENGTH: 6
<212> TYPE: PRT
<213> ORGANISM: Artificial
<220> FEATURE:
<223> OTHER INFORMATION: Synthetic peptide

<400> SEQUENCE: 71

Asn Arg Trp Leu Leu Gly
1 5

<210> SEQ ID NO 72
<211> LENGTH: 115
<212> TYPE: PRT
<213> ORGANISM: Artificial
<220> FEATURE:
<223> OTHER INFORMATION: Synthetic peptide

<400> SEQUENCE: 72

Gln Val Gln Leu Gln Gln Ser Gly Pro Gln Leu Val Arg Pro Gly Ala
1 5 10 15

Ser Val Lys Ile Ser Cys Lys Ala Ser Gly Tyr Ser Phe Thr Thr Tyr
20 25 30

```
Trp Met His Trp Val Lys Gln Arg Pro Gly Gln Gly Leu Glu Trp Ile
        35                  40                  45

Gly Leu Ile Asp Pro Ser Asp Ser Glu Thr Arg Leu Asn Gln Lys Phe
    50                  55                  60

Lys Asp Lys Ala Thr Leu Thr Val Asp Lys Ser Ser Ser Thr Ala Tyr
65                  70                  75                  80

Met Arg Leu Ser Ser Pro Thr Ser Glu Asp Ser Ala Val Tyr Tyr Cys
                85                  90                  95

Ala Ser Asn Arg Trp Leu Leu Gly Trp Gly Gln Gly Thr Leu Val Thr
            100                 105                 110

Val Ser Ser
        115


<210> SEQ ID NO 73
<211> LENGTH: 115
<212> TYPE: PRT
<213> ORGANISM: Artificial
<220> FEATURE:
<223> OTHER INFORMATION: Synthetic peptide

<400> SEQUENCE: 73

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Thr Tyr
            20                  25                  30

Trp Met His Trp Val Arg Gln Ala Pro Gly Gln Gly Leu Glu Trp Met
        35                  40                  45

Gly Leu Ile Asp Pro Ser Asp Ser Glu Thr Arg Leu Asn Gln Lys Phe
    50                  55                  60

Lys Asp Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Asn Arg Trp Leu Leu Gly Trp Gly Gln Gly Thr Leu Val Thr
            100                 105                 110

Val Ser Ser
        115


<210> SEQ ID NO 74
<211> LENGTH: 9
<212> TYPE: PRT
<213> ORGANISM: Artificial
<220> FEATURE:
<223> OTHER INFORMATION: Synthetic peptide

<400> SEQUENCE: 74

Gln Asn Asp Tyr Ser Tyr Pro Leu Thr
1               5


<210> SEQ ID NO 75
<211> LENGTH: 113
<212> TYPE: PRT
<213> ORGANISM: Artificial
<220> FEATURE:
<223> OTHER INFORMATION: Synthetic peptide

<400> SEQUENCE: 75

Asp Ile Gln Met Ile Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
```

```
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Thr Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys


<210> SEQ ID NO 76
<211> LENGTH: 113
<212> TYPE: PRT
<213> ORGANISM: Artificial
<220> FEATURE:
<223> OTHER INFORMATION: Synthetic peptide

<400> SEQUENCE: 76

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Leu Thr Phe Gly Gln Gly Thr Lys Leu Glu Ile
            100                 105                 110

Lys


<210> SEQ ID NO 77
<211> LENGTH: 10
<212> TYPE: PRT
<213> ORGANISM: Artificial
<220> FEATURE:
<223> OTHER INFORMATION: Synthetic peptide

<400> SEQUENCE: 77

Gly Phe Ser Leu Asn Ser Tyr Gly Val Gly
1               5                   10


<210> SEQ ID NO 78
<211> LENGTH: 16
<212> TYPE: PRT
<213> ORGANISM: Artificial
<220> FEATURE:
<223> OTHER INFORMATION: Synthetic peptide

<400> SEQUENCE: 78

Val Ile Trp Gly Asp Gly Ser Thr Asn Tyr His Ser Val Leu Ile Ser
1               5                   10                  15
```

<210> SEQ ID NO 79
<211> LENGTH: 9
<212> TYPE: PRT
<213> ORGANISM: Artificial
<220> FEATURE:
<223> OTHER INFORMATION: Synthetic peptide

<400> SEQUENCE: 79

```
Ile Thr Arg Gly Asn Ala Met Asp Tyr
1               5
```

<210> SEQ ID NO 80
<211> LENGTH: 117
<212> TYPE: PRT
<213> ORGANISM: Artificial
<220> FEATURE:
<223> OTHER INFORMATION: Synthetic peptide

<400> SEQUENCE: 80

```
Gln Val Gln Leu Lys Glu Ser Gly Pro Gly Leu Val Ala Pro Ser Gln
1               5                   10                  15

Ser Leu Ser Ile Thr Cys Ser Val Ser Gly Phe Ser Leu Asn Ser Tyr
            20                  25                  30

Gly Val Gly Trp Val Arg Gln Pro Pro Gly Lys Gly Leu Glu Trp Leu
        35                  40                  45

Gly Val Ile Trp Gly Asp Gly Ser Thr Asn Tyr His Ser Val Leu Ile
    50                  55                  60

Ser Arg Leu Ser Ile Arg Lys Asp Asn Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Met Ile Thr Arg Gly Asn Ala Met Asp Tyr Trp Gly Gln Gly Thr Ser
            100                 105                 110

Val Thr Val Ser Ser
        115
```

<210> SEQ ID NO 81
<211> LENGTH: 7
<212> TYPE: PRT
<213> ORGANISM: Artificial
<220> FEATURE:
<223> OTHER INFORMATION: Synthetic peptide

<400> SEQUENCE: 81

```
Trp Ala Ser Thr Arg Lys Ser
1               5
```

<210> SEQ ID NO 82
<211> LENGTH: 9
<212> TYPE: PRT
<213> ORGANISM: Artificial
<220> FEATURE:
<223> OTHER INFORMATION: Synthetic peptide

<400> SEQUENCE: 82

```
Gln Asn Asn Tyr Leu Phe Pro Leu Thr
1               5
```

<210> SEQ ID NO 83
<211> LENGTH: 113
<212> TYPE: PRT
<213> ORGANISM: Artificial
<220> FEATURE:
<223> OTHER INFORMATION: Synthetic peptide

<400> SEQUENCE: 83

Asp Ile Val Met Thr Gln Ser Pro Ser Ser Leu Thr Val Thr Ala Gly
1 5 10 15

Glu Lys Ile Thr Met Ser Cys Lys Ser Ser Gln Ser Leu Leu Asn Ser
20 25 30

Gly Asn Gln Arg Asn Tyr Leu Thr Trp Tyr Gln Gln Lys Pro Gly Gln
35 40 45

Thr Pro Lys Leu Leu Ile Tyr Trp Ala Ser Thr Arg Lys Ser Gly Val
50 55 60

Pro Asp Arg Phe Thr Gly Ser Gly Ser Gly Thr Asp Phe Thr Leu Thr
65 70 75 80

Ile Ser Ser Val Gln Ala Glu Asp Leu Ala Val Tyr Ser Cys Gln Asn
85 90 95

Asn Tyr Leu Phe Pro Leu Thr Phe Gly Ala Gly Thr Lys Leu Glu Leu
100 105 110

Lys

<210> SEQ ID NO 84
<211> LENGTH: 16
<212> TYPE: PRT
<213> ORGANISM: Artificial
<220> FEATURE:
<223> OTHER INFORMATION: Synthetic peptide

<400> SEQUENCE: 84

Val Ile Trp Gly Asp Val Ser Thr Asn Tyr His Ser Val Leu Ile Ser
1 5 10 15

<210> SEQ ID NO 85
<211> LENGTH: 117
<212> TYPE: PRT
<213> ORGANISM: Artificial
<220> FEATURE:
<223> OTHER INFORMATION: Synthetic peptide

<400> SEQUENCE: 85

Gln Val Gln Leu Gln Glu Ser Gly Pro Gly Leu Val Lys Pro Ser Glu
1 5 10 15

Thr Leu Ser Leu Thr Cys Thr Val Ser Gly Phe Ser Leu Asn Ser Tyr
20 25 30

Gly Val Gly Trp Ile Arg Gln Pro Pro Gly Lys Gly Leu Glu Trp Ile
35 40 45

Gly Val Ile Trp Gly Asp Val Ser Thr Asn Tyr His Ser Val Leu Ile
50 55 60

Ser Arg Val Thr Ile Ser Lys Asp Thr Ser Lys Asn Gln Val Ser Leu
65 70 75 80

Lys Leu Ser Ser Val Thr Ala Ala Asp Thr Ala Val Tyr Tyr Cys Ala
85 90 95

Arg Ile Thr Arg Gly Asn Ala Met Asp Tyr Trp Gly Gln Gly Thr Leu
100 105 110

Val Thr Val Ser Ser
115

<210> SEQ ID NO 86
<211> LENGTH: 113
<212> TYPE: PRT
<213> ORGANISM: Artificial
<220> FEATURE:

<223> OTHER INFORMATION: Synthetic peptide

<400> SEQUENCE: 86

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Arg Asn Tyr Leu Thr Trp Tyr Gln Gln Lys Pro Gly Gln
        35                  40                  45

Pro Pro Lys Leu Leu Ile Tyr Trp Ala Ser Thr Arg Lys Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asn Tyr Leu Phe Pro Leu Thr Phe Gly Gly Gly Thr Lys Val Glu Ile
            100                 105                 110

Lys
```

<210> SEQ ID NO 87
<211> LENGTH: 10
<212> TYPE: PRT
<213> ORGANISM: Artificial
<220> FEATURE:
<223> OTHER INFORMATION: Synthetic peptide

<400> SEQUENCE: 87

```
Gly Tyr Thr Phe Thr Ser Tyr Trp Ile Asn
1               5                   10
```

<210> SEQ ID NO 88
<211> LENGTH: 16
<212> TYPE: PRT
<213> ORGANISM: Artificial
<220> FEATURE:
<223> OTHER INFORMATION: Synthetic peptide

<400> SEQUENCE: 88

```
Asn Ile Tyr Pro Ser Asp Ser Tyr Thr Asn Tyr Asn Gln Lys Phe Lys
1               5                   10                  15
```

<210> SEQ ID NO 89
<211> LENGTH: 9
<212> TYPE: PRT
<213> ORGANISM: Artificial
<220> FEATURE:
<223> OTHER INFORMATION: Synthetic peptide

<400> SEQUENCE: 89

```
Ser Trp Arg Gly Asn Ser Phe Asp Tyr
1               5
```

<210> SEQ ID NO 90
<211> LENGTH: 118
<212> TYPE: PRT
<213> ORGANISM: Artificial
<220> FEATURE:
<223> OTHER INFORMATION: Synthetic peptide

<400> SEQUENCE: 90

```
Gln Val Gln Leu Gln Gln Pro Gly Ala Glu Leu Val Arg Pro Gly Ala
1               5                   10                  15
```

Ser Val Lys Leu Ser Cys Lys Ala Ser Gly Tyr Thr Phe Thr Ser Tyr
20 25 30

Trp Ile Asn Trp Val Lys Gln Arg Pro Gly Gln Gly Leu Glu Trp Ile
35 40 45

Gly Asn Ile Tyr Pro Ser Asp Ser Tyr Thr Asn Tyr Asn Gln Lys Phe
50 55 60

Lys Asp Lys Ala Thr Leu Thr Val Asp Lys Ser Ser Ser Thr Ala Tyr
65 70 75 80

Met Gln Leu Ser Ser Pro Thr Ser Glu Asp Ser Ala Val Tyr Tyr Cys
85 90 95

Thr Arg Ser Trp Arg Gly Asn Ser Phe Asp Tyr Trp Gly Gln Gly Thr
100 105 110

Thr Leu Thr Val Ser Ser
115

<210> SEQ ID NO 91
<211> LENGTH: 9
<212> TYPE: PRT
<213> ORGANISM: Artificial
<220> FEATURE:
<223> OTHER INFORMATION: Synthetic peptide

<400> SEQUENCE: 91

Gln Asn Asp Tyr Ser Tyr Pro Phe Thr
1 5

<210> SEQ ID NO 92
<211> LENGTH: 113
<212> TYPE: PRT
<213> ORGANISM: Artificial
<220> FEATURE:
<223> OTHER INFORMATION: Synthetic peptide

<400> SEQUENCE: 92

Asp Ile Val Met Thr Gln Ser Pro Ser Ser Leu Thr Val Thr Ala Gly
1 5 10 15

Glu Lys Val Thr Met Ser Cys Lys Ser Ser Gln Ser Leu Leu Asn Ser
20 25 30

Gly Asn Gln Lys Asn Tyr Leu Thr Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Thr Gly Ser Gly Ser Gly Thr Asp Phe Thr Leu Thr
65 70 75 80

Ile Ser Ser Val Gln Ala Glu Asp Leu Ala Val Tyr Tyr Cys Gln Asn
85 90 95

Asp Tyr Ser Tyr Pro Phe Thr Phe Gly Ser Gly Thr Lys Leu Glu Ile
100 105 110

Lys

<210> SEQ ID NO 93
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (6)..(6)
<223> OTHER INFORMATION: Xaa can be any naturally occurring amino acid -continued

```
<400> SEQUENCE: 93

Tyr Ile Ala Pro Phe Xaa Gly Asp Ser Arg Tyr Asn Gln Lys Phe Lys
1               5                   10                  15

Gly


<210> SEQ ID NO 94
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 94

Val Ile Trp Gly Asp Xaa Ser Thr Asn Tyr His Ser Val Leu Ile Ser
1               5                   10                  15
```

ANTI-Claudin18.2 ANTIBODY AND USE THEREOF

The present application is a national stage application of PCT/CN2021/100870, which is based on and claims priority to Chinese Patent Application No. CN202010570517.X filed on Jun. 19, 2020, the disclosure of each of which is incorporated herein by reference in its entirety.

SEQUENCE LISTING

This application contains a Sequence Listing which has been filed electronically in ASCII format and is hereby incorporated by reference in its entirety. Said ASCII copy, created on Dec. 5, 2022, is named 03229750.TXT and is 55,392 bytes in size.

The present invention relates to a novel antibody and an antibody fragment that specifically bind to Claudin18.2 and a composition comprising the antibody or the antibody fragment. In addition, the present invention relates to a nucleic acid encoding the antibody or the antibody fragment thereof, a host cell comprising the nucleic acid, and related uses. Furthermore, the present invention relates to therapeutic and diagnostic uses of the antibody and the antibody fragment.

BACKGROUND

Claudins are a family of proteins and are important components that constitute tight junctions between cells. They establish an intercellular barrier that controls the intercellular flow of molecules, and thus can control the flow of the molecules between cells. Claudins family proteins have a tetraspanin domain, both N-terminus and C-terminus of which are included in the cytoplasm. Different Claudins are expressed on different tissues and their functional changes are associated with the development of cancer in various tissues. For example, Claudin-1 is expressed in colon cancer and has prognostic value, Claudin-18 is expressed in gastric cancer, and Claudin-10 is expressed in hepatocellular carcinoma. Claudins, as cell membrane surface proteins, are useful targets of various therapeutic strategies.

Isoform 2 of Claudin-18 (Claudin18.2 or CLDN18.2) is a highly selective cell lineage marker. Its expression in normal tissues is strictly confined to differentiated epithelial cells of the gastric mucosa and its expression is absent from the gastric stem cell zone. CLDN18.2 is expressed in a considerable portion of primary gastric cancers, and its expression level is retained in gastric metastatic cancer tissue. Expression of CLDN18.2 has also been found in pancreatic cancer in addition to gastric cancer, and it is an ideal target molecule for the treatment of these cancers (Singh, P., Toom, S. & Huang, Y. Anti-CLDN18.2 antibody as new targeted therapy for advanced gastric cancer. *J Hematol Oncol* 10, 105 (2017). doi.org/10.1186/s13045-017-0473-4.

Due to the large unmet clinical need for tumor therapy, the development of drugs targeting Claudin18.2 is necessary. Although some monoclonal antibodies against Claudin18.2 have been developed in the prior art, most of these antibodies are chimeric antibodies, which have a potentially high risk of immunogenicity, low affinity, poor specificity and ordinary ADCC activity. Therefore, there is still a need to develop new antibodies against Claudin18.2, which have lower immunogenicity, stronger binding affinity for Claudin18.2, good specificity, strong ADCC and CDC activity and better anti-tumor activity.

SUMMARY

In some aspects, the present invention relates to an antibody or an antigen-binding fragment thereof that binds to CLDN18.2, which comprises 3 heavy chain variable region CDRs and 3 light chain variable region CDRs as described herein.

In some aspects, the antibody or the antigen-binding fragment thereof that binds to CLDN18.2 of the present invention comprises a heavy chain variable region and/or a light chain variable region as described herein.

In some aspects, the antibody or the antigen-binding fragment thereof that binds to CLDN18.2 of the present invention further comprises a heavy chain constant region and/or a light chain constant region as described herein.

In some aspects, the present invention also relates to the following embodiments.

1. Provided is the antibody or the antigen-binding fragment thereof that binds to CLDN18.2 of the present invention, wherein the antibody is an antibody or an antigen-binding fragment in the form of IgG1, IgG2, IgG3 or IgG4, preferably an antibody or an antigen-binding fragment in the form of IgG1.
2. Provided is the antibody or the antigen-binding fragment thereof that binds to CLDN18.2 of the present invention, wherein the antibody is a monoclonal antibody.
3. Provided is the antibody or the antigen-binding fragment thereof that binds to CLDN18.2 of the present invention, wherein the antibody is a humanized antibody, a human antibody or a chimeric antibody.
4. Provided is the antibody or the antigen-binding fragment thereof that binds to CLDN18.2 of the present invention, wherein the antigen-binding fragment is an antibody fragment selected from: Fab, Fab', Fab'-SH, Fv, a single-chain antibody (e.g., scFv), $(Fab')_2$, a single-domain antibody (e.g., VHH), a domain antibody (dAb) and a linear antibody.
5. Provided is the antibody or the antigen-binding fragment thereof that binds to CLDN18.2 of the present invention, wherein the antibody or the antigen-binding fragment thereof has one or more of the following properties:

(i) binding to CLDN18.2 (e.g., human CLDN18.2) with high affinity, but not binding to CLDN18.1 (e.g., human CLDN18.1);

(ii) binding to human CLDN18.2 with an equilibrium dissociation constant ($K_D$) of less than about 15 nM, preferably less than or equal to about 10 nM, 9.5 nM, 9 nM, 8.5 nM, 8 nM, 7.5 nM, 7 nM, 6.5 nM, 6 nM, 5.5 nM, 5 nM, 4.5 nM, 4 nM, 3.5 nM or 3 nM;

(iii) binding to CLDN18.2 on cell surface, but not binding to CLDN18.1 on cell surface;

(iv) having ADCC activity or CDC activity, e.g., ADCC activity or CDC activity equivalent to or higher than that of a known antibody (e.g., Zmab);

(v) inhibiting tumor cells, e.g., tumor cells expressing CLDN18.2; and (vi) being capable of effectively inhibiting tumor growth with a tumor growth inhibition of greater than or equal to about 25%, 30%, 35%, 40%, 45%, 50%, 55%, 60%, 65% or 70%.

6. Provided is an isolated nucleic acid encoding a light chain variable region or a heavy chain variable region, or a light chain or a heavy chain, of the antibody or the antigen-binding fragment thereof that binds to CLDN18.2 of the present invention.

7. Provided is a vector comprising the nucleic acid of the present invention, wherein, preferably, the vector is an expression vector.
8. Provided is a host cell comprising the nucleic acid or the vector of the present invention, wherein, preferably, the host cell is prokaryotic or eukaryotic, and more preferably, the host cell is selected from yeast cells, mammalian cells (e.g., 293 cells or CHO cells, such as CHO-S cells or HEK293 cells), or additional cells suitable for preparing an antibody or an antigen-binding fragment thereof.
9. Provided is a method for preparing an antibody or an antigen-binding fragment thereof that binds to CLDN18.2, which comprises: cultivating the host cell of the present invention under conditions suitable for expressing the nucleic acid encoding the antibody or the antigen-binding fragment thereof that binds to CLDN18.2 of the present invention, and optionally, isolating the antibody or the antigen-binding fragment thereof; optionally, the method further comprises recovering the antibody or the antigen-binding fragment thereof that binds to CLDN18.2 from the host cell.
10. Provided is an immunoconjugate comprising the antibody or the antigen-binding fragment thereof that binds to CLDN18.2 of the present invention and an additional substance, e.g., a cytotoxic agent.
11. Provided is a pharmaceutical composition comprising the antibody or the antigen-binding fragment thereof that binds to CLDN18.2 of the present invention or the immunoconjugate of the present invention, and optionally one or more additional therapeutic agents, e.g., a chemotherapeutic agent, a cytokine, a cytotoxic agent, an additional antibody, a small molecule drug or an immunomodulatory agent, and optionally a pharmaceutical supplementary material.
12. Provided is a pharmaceutical combination comprising the antibody or the antigen-binding fragment thereof that binds to CLDN18.2 of the present invention or the immunoconjugate of the present invention, and one or more additional therapeutic agents, e.g., a chemotherapeutic agent, a cytokine, a cytotoxic agent, an additional antibody, a small molecule drug or an immunomodulatory agent.
13. Provided is a method for preventing or treating a tumor in a subject, which comprises administering to the subject an effective amount of the antibody or the antigen-binding fragment thereof that binds to CLDN18.2 of the present invention, or the immunoconjugate, the pharmaceutical composition or the pharmaceutical combination of the present invention.
14. Provided is a method for inducing ADCC and/or CDC in a subject, which comprises administering to the subject an effective amount of the antibody or the antigen-binding fragment thereof that binds to CLDN18.2 of the present invention, or the immunoconjugate, the pharmaceutical composition or the pharmaceutical combination of the present invention.
15. Provided is use of the antibody or the immunoconjugate of the present invention in preparing a drug or a pharmaceutical combination for treating or preventing tumors and/or inducing ADCC and/or CDC.
16. Provided is the method or the use of the present invention, wherein the tumor is a cancer; preferably, the cancer has an elevated level of CLDN18.2 (e.g., at the nucleic acid or protein level).
17. Provided is the method of the present invention, wherein the method further comprises administering to a patient one or more therapies, e.g., therapeutic modalities and/or additional therapeutic agents; preferably, the therapeutic modalities comprise surgical treatment and/or radiotherapy, and the additional therapeutic agents are selected from a chemotherapeutic agent, a cytokine, a cytotoxic agent, an additional antibody, a small molecule drug and an immunomodulatory agent.
18. Provided is the use of the present invention, wherein the drug or the pharmaceutical combination is capable of being administered to a subject in combination with one or more therapies, e.g., therapeutic modalities and/or additional therapeutic agents; preferably, the therapeutic modalities comprise surgical treatment and/or radiotherapy, and the additional therapeutic agents are selected from a chemotherapeutic agent, a cytokine, a cytotoxic agent, an additional antibody, a small molecule drug and an immunomodulatory agent.
19. Provided is a method for detecting CLDN18.2 in a sample, which comprises
(a) contacting the sample with the antibody or the antigen-binding fragment thereof of the present invention; and
(b) detecting a complex formed by the antibody or the antigen-binding fragment thereof and CLDN18.2, wherein, optionally, the antibody is detectably labeled.

DETAILED DESCRIPTION

I. Definitions

Figure 1:
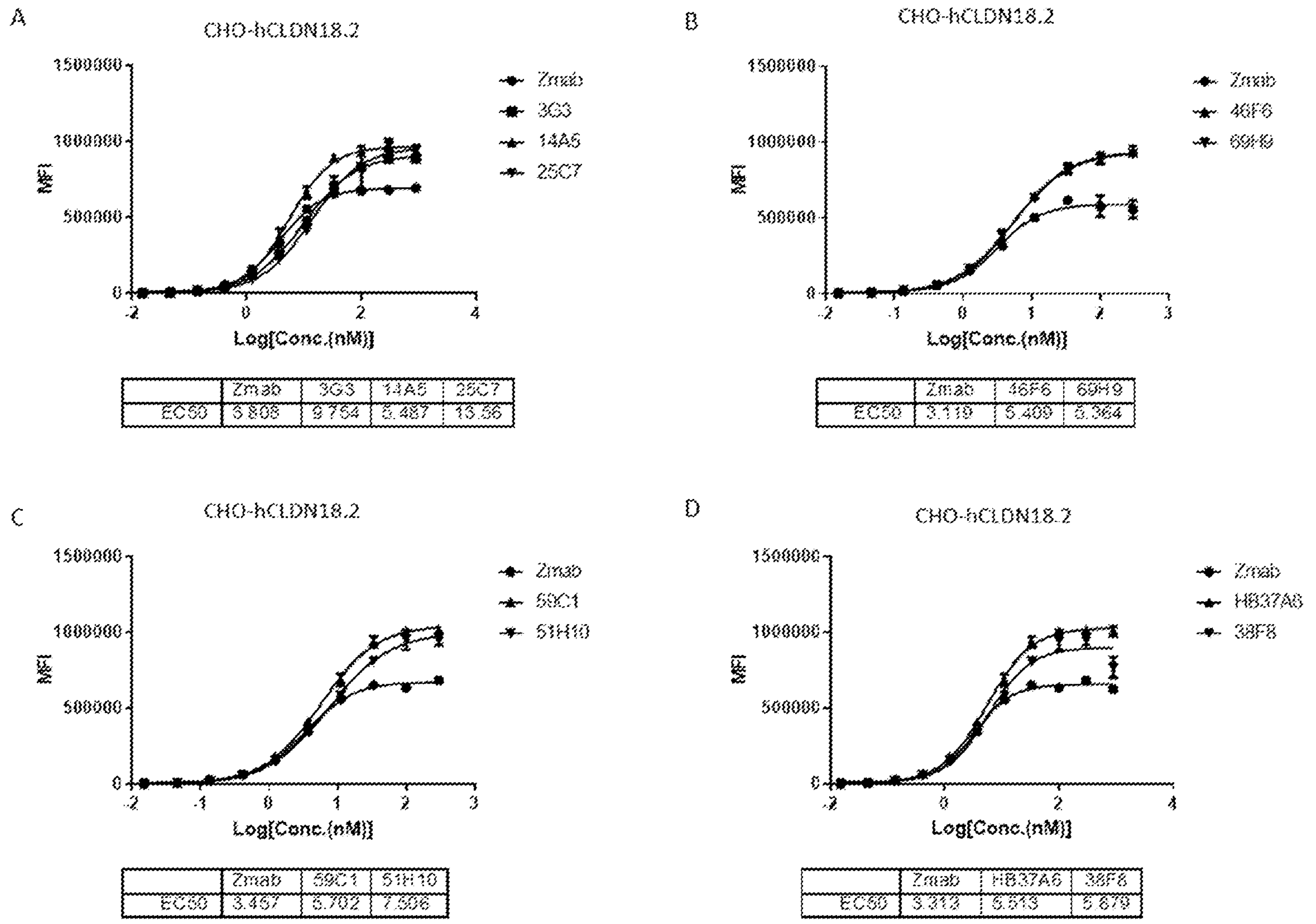
FIG. 1 shows that anti-CLDN18.2 antibodies specifically bind to CLDN18.2 on cell surface.

Before the present invention is described in detail below, it should be understood that the present invention is not limited to the particular methodology, protocols, and reagents described herein, as these may vary. It should also be understood that the terminology used herein is only intended to describe specific embodiments rather than limit the scope of the present invention, which will be limited only by the appended claims. Unless otherwise defined, any technical and scientific term used herein has the same meaning as commonly understood by those of ordinary skill in the art to which the present invention belongs.

For the purpose of explaining this specification, the following definitions will be used, and wherever appropriate, terms used in the singular form may also include the plural form, and vice versa. It should be understood that the terms used herein are for the purpose of describing specific embodiments only, and are not intended to be limiting.

The term "about" used in combination with a numerical value is intended to encompass the numerical values in a range from a lower limit less than the specified numerical value by 5% to an upper limit greater than the specified numerical value by 5%.

As used herein, the term "and/or" refers to any one of the options or any two or more of the options.

As used herein, the term "comprise" or "include" is intended to mean that the described elements, integers or steps are included, but not to the exclusion of any other elements, integers or steps. The term "comprise" or "include" used herein, unless otherwise specified, also encompasses the situation where the entirety consists of the described elements, integers or steps. For example, when referring to an antibody variable region "comprising" a particular sequence, it is also intended to encompass an antibody variable region consisting of the particular sequence.

The term "CLAUDIN" or "CLDN" used herein is the most important skeleton protein that determines the structures of tight junctions between cells, and it is involved in adhesion junctions and plays an important role in the metastasis and invasion of tumor cells. Claudin proteins are widely present in mammalian epithelial and endothelial cells, primarily on the lateral surface of epithelial cells and on the plasma membrane of basal cells. Different Claudin proteins have their respective specific expression in different tissues, wherein the Claudin18 (CLDN18) gene is located at 3q22.3, has a molecular weight of 24 kDa, comprises 261 amino acid residues, and is a member of the Claudins superfamily, and its protein structure comprises 2 extracellular loops and 4 transmembrane domains. Two subtypes of human CLDN18 or Claudin18 protein are Claudin18.1 or CLDN18.1 (UniProt ID: P56856-1) and Claudin18.2 or CLDN18.2 (UniProt ID: P56856-2), respectively. In the primary structural sequences of the two proteins, only the amino acid residues at some positions from the N-terminus signal peptide to the extracellular loop 1 (Loop1) structure are different, and especially at the extracellular loop 1, CLDN18.1 and CLDN18.2 differ by only 8 amino acids. The intergeneric sequence homology of the two subtypes of CLDN18 protein is also very high. The sequences of the extracellular loop 1 of CLDN18.2 are completely identical in different species such as human, mouse and rhesus monkey, while the homology of human and mouse CLDN18.2 proteins reaches 84%, indicating that the sequence of CLDN18.2 protein is extremely conserved (O. Tureci. et al., *Gene,* 481:83-92, 2011). CLDN18.2 or any variants and isoforms thereof may be isolated from cells or tissues in which they are naturally expressed, or recombinantly produced using techniques well known in the art and/or those described herein. In one embodiment, the CLDN18.2 as described herein is a human CLDN18.2.

The term "anti-CLDN18.2 antibody", "anti-CLDN18.2", "CLDN18.2 antibody" or "antibody that binds to CLDN18.2" used herein refers to an antibody capable of binding to (human) CLDN18.2 with sufficient affinity such that the antibody can be used as a therapeutic agent targeting (human) CLDN18.2. In one embodiment, the (human) CLDN18.2 antibody binds to (human) CLDN18.2 with high affinity in vitro or in vivo. In one embodiment, the (human) CLDN18.2 antibody does not bind to CLDN18.1. In one embodiment, the (human) CLDN18.2 antibody binds to cells expressing CLDN18.2 but does not bind to cells expressing CLDN18.1. In some embodiments, the binding is determined, e.g., by radioimmunoassay (RIA), bio-layer interferometry (BLI), MSD assay, surface plasmon resonance (SPR) or flow cytometry.

The term "antibody fragment" includes a portion of an intact antibody. In a preferred embodiment, the antibody fragment is an antigen-binding fragment.

"Antigen-binding fragment" refers to a molecule different from an intact antibody, which comprises a portion of the intact antibody and binds to an antigen to which the intact antibody binds. Examples of the antibody fragments include, but are not limited to, Fv, Fab, Fab', Fab'-SH, $F(ab')_2$, a domain antibody (dAb), a linear antibody, a single-chain antibody (e.g., scFv), a single-domain antibody (e.g., VHH), a bi-valent antibody or a fragment thereof, or a camelid antibody.

The term "antigen" refers to a molecule that induces an immune response. Such an immune response may involve antibody production or activation of specific immune cells, or both. Those skilled will understand that any macromolecules, including essentially all proteins or peptides, can be used as antigens. In addition, an antigen may be derived from recombinant or genomic DNA.

As used herein, the term "epitope" refers to a moiety of an antigen (e.g., CLDN18.2) that specifically interacts with an antibody molecule.

An "antibody that binds to the same or overlapping epitope" as a reference antibody refers to an antibody that blocks 50%, 60%, 70%, 80%, 90% or 95% or more of the binding of the reference antibody to its antigen in a competition assay. Conversely, the reference antibody blocks 50%, 60%, 70%, 80%, 90% or 95% or more of the binding of the antibody to its antigen in a competition assay.

An antibody that competes with a reference antibody for binding to its antigen refers to an antibody that blocks 50%, 60%, 70%, 80%, 90% or 95% or more of the binding of the reference antibody to its antigen in a competition assay. Conversely, the reference antibody blocks 50%, 60%, 70%, 80%, 90% or 95% or more of the binding of the antibody to its antigen in a competition assay. Numerous types of competitive binding assays can be used to determine whether an antibody competes with another antibody, such as direct or indirect solid-phase radioimmunoassay (RIA), direct or indirect solid-phase enzyme immunoassay (EIA) and sandwich competition assay.

An antibody that inhibits (e.g., competitively inhibits) the binding of a reference antibody to its antigen refers to an antibody that inhibits 50%, 60%, 70%, 80%, 90% or 95% or more of the binding of the reference antibody to its antigen. Conversely, the reference antibody inhibits 50%, 60%, 70%, 80%, 90% or 95% or more of the binding of the antibody to its antigen. The binding of an antibody to its antigen can be measured by affinity (e.g., equilibrium dissociation constant). Methods for determining affinity are known in the art.

An antibody that shows the same or similar binding affinity and/or specificity as a reference antibody refers to an antibody that is capable of having at least 50%, 60%, 70%, 80%, 90% or 95% or more of the binding affinity and/or specificity of the reference antibody. This can be determined by any method known in the art for determining binding affinity and/or specificity.

"Complementarity determining region" or "CDR region" or "CDR" is a region in an antibody variable domain that is highly variable in sequence and forms a structurally defined loop ("hypervariable loop") and/or comprises antigen-contacting residues ("antigen contact site"). CDRs are primarily responsible for binding to antigen epitopes. The CDRs of the heavy and light chains are generally referred to as CDR1, CDR2, and CDR3, and are numbered sequentially from the N-terminus. The CDRs located in the heavy chain variable domain of the antibody are referred to as HCDR1, HCDR2 and HCDR3, whereas the CDRs located in the light chain variable domain of the antibody are referred to as LCDR1, LCDR2 and LCDR3. In a given amino acid sequence of a light chain variable region or a heavy chain variable region, the exact amino acid sequence boundary of each CDR can be determined using any one or a combination of many well-known antibody CDR assignment systems including, e.g., Chothia based on the three-dimensional structure of antibodies and the topology of the CDR loops (Chothia et al. (1989) *Nature,* 342:877-883; Al-Lazikani et al., Standard conformations for the canonical structures of immunoglobulins, *Journal of Molecular Biology,* 273:927-948 (1997)), Kabat based on antibody sequence variability (Kabat et al., *Sequences of Proteins of Immunological Interest,* 4$^{th}$ Ed., U.S. Department of Health and Human Services, National Institutes of Health (1987)), AbM (University of Bath), Contact (University College London), International ImMunoGeneTics database (IMGT) (imgt.cines.fr/on the World Wide Web), and North CDR definition based on the affinity propagation clustering using a large number of crystal structures.

For example, according to different CDR determination schemes, the residues of each CDR are as follows.

| CDR | Kabat scheme | AbM scheme | Chothia scheme | Contact scheme |
|---|---|---|---|---|
| (Kabat numbering system) | | | | |
| LCDR1 | L24-L34 | L24-L34 | L26-L32 | L30-L36 |
| LCDR2 | L50-L56 | L50-L56 | L50-L52 | L46-L55 |
| LCDR3 | L89-L97 | L89-L97 | L91-L96 | L89-L96 |
| HCDR1 | H31-H35B | H26-H35B | H26-H32 | H30-H35B |
| (Chothia numbering system) | | | | |
| HCDR1 | H31-H35 | H26-H35 | H26-H32 | H30-H35 |
| (Kabat numbering system) | | | | |
| HCDR2 | H50-H65 | H50-H58 | H53-H55 | H47-H58 |
| HCDR3 | H95-H102 | H95-H102 | H96-H101 | H93-H101 |

CDRs can also be determined based on having the same Kabat numbering positions as a reference CDR sequence (e.g., any of the exemplary CDRs of the present invention).

Unless otherwise stated, the term "CDR" or "CDR sequence" used herein encompasses CDR sequences determined by any one of the schemes above.

Unless otherwise stated, residue positions of an antibody variable region (including heavy chain variable region residues and light chain variable region residues) are numbered according to the Kabat numbering system (Kabat et al., *Sequences of Proteins of Immunological Interest,* 5$^{th}$ Ed. Public Health Service, National Institutes of Health, Bethesda, Md. (1991)).

In one embodiment, the heavy chain variable region CDRs of the antibody of the present invention are determined according to the following rules:

the VH CDR1 is determined according to AbM rules, and the VH CDR 2 and 3 are both determined according to Kabat rules.

In one embodiment, the light chain variable region CDRs of the antibody of the present invention are determined according to Kabat rules.

In one embodiment, the heavy chain variable region CDRs of the antibody of the present invention are determined according to the following rules: the VH CDR1 is determined according to AbM rules, and the VH CDR 2 and 3 are both determined according to Kabat rules; and the light chain variable region CDRs are determined according to Kabat rules.

It should be noted that boundaries of CDRs in variable regions of an antibody determined by different assignment systems may differ. That is, the CDR sequences of variable regions of the same antibody defined by different assignment systems differ. Accordingly, when it comes to defining an antibody with specific CDR sequences defined in the present invention, the scope of antibody also encompasses such antibodies whose variable region sequences comprise the specific CDR sequences, but have claimed CDR boundaries different from the specific CDR boundaries defined by the present invention due to a different scheme (e.g., different assignment system rules or their combinations) applied.

Antibodies with different specificities (i.e., different binding sites for different antigens) have different CDRs (under the same assignment system). However, although CDRs vary from antibody to antibody, only a limited number of amino acid positions within the CDRs are directly involved in antigen binding. The smallest overlapping region can be determined using at least two of the Kabat, Chothia, AbM, Contact, and North methods, thereby providing a "minimal binding unit" for antigen binding. The minimal binding unit may be a sub-portion of the CDR. As will be clear to those skilled in the art, residues in remaining portions of the CDR sequences can be determined by the structure and protein folding of the antibody. Accordingly, variants of any CDR presented herein are also considered. For example, in a variant of one CDR, the amino acid residue of the minimal binding unit may remain unchanged, while the remaining CDR residues defined by the Kabat or Chothia may be conservatively substituted.

The term "Fc region" is used herein to define the constant regions of CH2 and CH3 of immunoglobulin heavy chains, and includes Fc regions of native sequences and variant Fc regions. The Fc region can bind to different Fc receptors on immune cell surface, thereby causing CDC\ADCC\ADCP effector functions. Such effector functions generally require that the Fc region is associated with a binding domain (e.g., an antibody variable domain) and can be assessed using a variety of assays, such as those disclosed herein.

"Antibody in the form of IgG" refers to the heavy chain constant region of the antibody belonging to the IgG form. Heavy chain constant regions of all antibodies of the same type are identical, and heavy chain constant regions of antibodies of different types are different. For example, an antibody in the form of IgG4 refers to the heavy chain constant region of the antibody being from IgG4, or an antibody in the form of IgG1 refers to the heavy chain constant region of the antibody being from IgG1.

"Humanized" antibody refer to an antibody comprising amino acid residues from non-human CDRs and amino acid residues from human FRs. In some embodiments, a humanized antibody will comprise at least one, or generally two of substantially all variable domains in which all or substantially all CDRs (e.g., CDRs) correspond to those of a non-human antibody, and all or substantially all FRs correspond to those of a human antibody. A humanized antibody may optionally comprise at least a portion of an antibody constant region derived from a human antibody. The "humanized form" of an antibody (such as a non-human antibody) refers to an antibody that has been humanized.

"Human antibody", "fully human antibody" and "fully humanized antibody" are used interchangeably, and refer to an antibody having an amino acid sequence which corresponds to the amino acid sequence of an antibody generated by a human or human cell or derived from a non-human source that utilizes human antibody libraries or other human antibody encoding sequences. This definition of a human antibody explicitly excludes humanized antibodies comprising non-human antigen-binding residues.

As used herein, the term "binding" or "specific binding" means that the binding effect is selective for antigens and can be distinguished from unwanted or non-specific interactions. The ability of an antigen-binding site to bind to a particular antigen can be determined by enzyme-linked immunosorbent assay (ELISA) or conventional binding assays known in the art, such as radioimmunoassay (RIA), bio-layer interferometry, MSD assay or surface plasmon resonance (SPR).

"Immunoconjugate" is an antibody conjugated to one or more other substances, including but not limited to cytotoxic agents or labels.

The term "therapeutic agent" used herein encompasses any substance that is effective in preventing or treating a tumor, e.g., cancer, including a chemotherapeutic agent, a cytokine, a cytotoxic agent, an additional antibody, a small molecule drug or an immunosuppressant (e.g., an immunosuppressive agent).

The term "cytotoxic agent" used herein refers to a substance that inhibits or prevents cell functions and/or causes cell death or cell destruction.

"Chemotherapeutic agents" include chemical compounds useful in the treatment of immune system diseases.

The term "small molecule drug" refers to a low molecular weight organic compound capable of regulating biological processes. "Small molecule" is defined as a molecule with a molecular weight of less than 10 kD, usually less than 2 kD and preferably less than 1 kD. The small molecule includes but is not limited to inorganic molecules, organic molecules, organic molecules containing inorganic components, molecules containing radioactive atoms, synthetic molecules, peptide mimetics, and antibody mimetics. As therapeutic agents, small molecules penetrate cells better, are less susceptible to degradation and are less likely to induce an immune response compared with large molecules.

The term "immunomodulatory agent" used herein refers to a natural or synthetic active agent or drug that suppresses or modulates an immune response. The immune response may be a humoral response or a cellular response. The immunomodulatory agent includes an immunosuppressant.

"Immunosuppressant", "immunosuppressive drug" or "immunosuppressive substance" used herein refers to a therapeutic agent used in immunosuppressive therapy to suppress or prevent the activity of the immune system.

The term "effective amount" refers to the amount or dose of the antibody, fragment, conjugate, composition or combination of the present invention that generates expected effects in a patient in need of treatment or prevention after administration to the patient in a single or multiple doses.

"Therapeutically effective amount" refers to an amount effective to achieve a desired therapeutic result at a necessary dose for a necessary period of time. The therapeutically effective amount is also such an amount that any toxic or undesired effect of the antibody or the fragment thereof, or conjugate, composition or combination thereof is inferior to the therapeutically beneficial effect.

The "therapeutically effective amount" preferably inhibits a measurable parameter (e.g., tumor volume) by at least about 20%, more preferably by at least about 40%, and even more preferably by at least about 50%, 60% or 70%, relative to untreated subjects.

"Prophylactically effective amount" refers to an amount effective to achieve a desired prophylactic result at a necessary dose for a necessary period of time. Generally, since a prophylactic dose is administered in a subject before or at an earlier stage of a disease, a prophylactically effective amount will be less than a therapeutically effective amount.

The terms "host cell", "host cell line" and "host cell culture" are used interchangeably and refer to cells into which exogenous nucleic acids are introduced, including progenies of such cells. Host cells include "transformants" and "transformed cells", which include primary transformed cells and progenies derived therefrom, regardless of the number of passages. Progeny may not be exactly the same as parent cells in terms of nucleic acid content, and may contain mutations.

Mutant progeny having the same function or biological activities that are screened or selected from the initially transformed cells are included herein.

The term "label" used herein refers to a compound or composition which is directly or indirectly conjugated or fused to an agent, such as a polynucleotide probe or an antibody, and facilitates the detection of the agent to which it is conjugated or fused. The label itself can be detectable (e.g., a radioisotope label or a fluorescent label) or can catalyze a chemical change to a detectable substrate compound or composition in the case of enzymatic labeling. The term is intended to encompass direct labeling of a probe or an antibody by coupling (i.e., physical linking) a detectable substance to the probe or an antibody and indirect labeling of a probe or antibody by reacting with another reagent which is directly labeled.

"Individual" or "subject" includes mammals. The mammals include, but are not limited to, domestic animals (e.g., cattle, goats, cats, dogs, and horses), primates (e.g., human and non-human primates such as monkeys), rabbits, and rodents (e.g., mice and rats). In some embodiments, the individual or subject is a human.

An "isolated" antibody is an antibody which has been separated from components of its natural environment. In some embodiments, the antibody is purified to a purity greater than 95% or 99% as determined by, e.g., electrophoresis (e.g., SDS-PAGE, isoelectric focusing (IEF) and capillary electrophoresis) or chromatography (e.g., ion exchange or reverse-phase HPLC).

"An isolated nucleic acid encoding an anti-CLDN18.2 antibody or a fragment thereof" refers to one or more nucleic acid molecules encoding the antibody heavy or light chain (or fragment thereof, e.g., heavy chain variable region or light chain variable region), including such nucleic acid molecules in a single vector or separate vectors, and such nucleic acid molecules present at one or more locations in a host cell.

The calculation of sequence identity between sequences is performed as follows.

To determine the percent identity of two amino acid sequences or two nucleic acid sequences, the sequences are aligned for optimal comparison purposes (e.g., for optimal alignment, gaps can be introduced in one or both of the first and second amino acid sequences or nucleic acid sequences, or non-homologous sequences can be discarded for comparison). In one preferred embodiment, for comparison purposes, the length of the aligned reference sequence is at least 30%, preferably at least 40%, more preferably at least 50% or 60%, and even more preferably at least 70%, 80%, 90%, or 100% of the length of the reference sequence. Amino acid residues or nucleotides at corresponding amino acid positions or nucleotide positions are then compared. When a position in the first sequence is occupied by the same amino acid residue or nucleotide at the corresponding position in the second sequence, the molecules are identical at this position.

A mathematical algorithm can be used to compare two sequences and calculate percent identity between the sequences. In one preferred embodiment, the percent identity between two amino acid sequences is determined with the Needlema and Wunsch algorithm ((1970) *J. Mol. Biol.*, 48:444-453; available at www.geg.com) which has been integrated into the GAP program of the GCG software package, using the Blossom 62 matrix or PAM250 matrix and gap weight of 16, 14, 12, 10, 8, 6, or 4 and length weight of 1, 2, 3, 4, 5, or 6. In another preferred embodiment, the percent identity between two nucleotide acid sequences is determined with the GAP program of the GCG software package (available at www.gcg.com), using the NWSgapdna.CMP matrix and a gap weight of 40, 50, 60, 70 or 80 and a length weight of 1, 2, 3, 4, 5 or 6. A particularly preferred parameter set (and one that should be used unless otherwise stated) is a Blossom 62 scoring matrix with a gap penalty of 12, a gap extension penalty of 4, and a frameshift gap penalty of 5. The percent identity between two amino acid sequences or nucleotide sequences can also be determined with PAM120 weighted remainder table, a gap length penalty of 12 and a gap penalty of 4, using the E. Meyers and W. Miller algorithm ((1989) CABIOS, 4:11-17) which has been incorporated into the ALIGN program (version 2.0). Additionally or alternatively, the nucleic acid sequences and protein sequences described herein can be further used as "query sequences" to perform searches against public databases to, e.g., identify other family member sequences or related sequences.

As used herein, the term "hybridization under stringency conditions (such as low stringency, medium stringency, high stringency or extreme stringency)" describes hybridization and washing conditions. Instructions for performing hybridization reactions can be found in *Current Protocols in Molecular Biology*, John Wiley & Sons, N.Y. (1989), 6.3.1-6.3.6, which is incorporated by reference. Aqueous and non-aqueous methods are described in the references and either method can be used. The preferred hybridization conditions mentioned herein are as follows: 1) low stringency hybridization conditions are in 6× sodium chloride/sodium citrate (SSC) at about 45 °C, followed by two washes in 0.2×SSC, 0.1% SDS at least at 50 °C (for low stringency conditions, the temperature of the washes can be increased to 55 °C); 2) medium stringency hybridization conditions are in 6×SSC at about 45 °C, followed by one or more washes in 0.2×SSC, 0.1% SDS at about 60 °C; 3) high stringency hybridization conditions are in 6×SSC at about 45 °C, followed by one or more washes in 0.2×SSC, 0.1% SDS at 65 °C; and preferably 4) extreme stringency hybridization conditions are in 0.5 M sodium phosphate, 7% SDS at 65 °C, followed by one or more washes in 0.2×SSC, 0.1% SDS at 65 °C. Extreme stringency condition (4) is a preferred condition and the one that should be used unless otherwise stated.

The term "anti-tumor effect" refers to a biological effect that can be demonstrated by a variety of means, including but not limited to, for example, decrease in tumor volume, decrease in number of tumor cells, decrease in tumor cell proliferation, or decrease in tumor cell viability.

The terms "tumor" and "cancer" are used interchangeably herein and encompass solid and liquid tumors.

The terms "cancer" and "cancerous" refer to or describe a physiological disease in mammals that is typically characterized by unregulated cell growth. In certain embodiments, cancers suitable for treatment with the antibody of the present invention include gastric cancer or pancreatic cancer, including metastatic forms of such cancers.

The term "tumor" refers to all neoplastic cell growth and proliferation, whether being malignant or benign, and all pre-cancerous and cancerous cells and tissues. The terms "cancer", "cancerous" and "tumor" are not mutually exclusive when referred to herein.

The term "pharmaceutical supplementary material" refers to diluents, adjuvants (e.g., Freund's adjuvants (complete and incomplete)), excipients, carriers, stabilizers, or the like, which are administered with the active substance.

The term "pharmaceutical composition" refers to such a composition that exists in a form allowing effective biological activity of the active ingredient contained therein, and does not contain additional ingredients having unacceptable toxicity to a subject to which the composition is administered.

The term "pharmaceutical combination" refers to a non-fixed combination product or a fixed combination product, including but not limited to a kit and a pharmaceutical composition. The term "non-fixed combination" means that the active ingredients (e.g., (i) an anti-CLDN18.2 antibody or a fragment thereof, and (ii) an additional therapeutic agent) are administered, either simultaneously or sequentially (without specific time limitation or at identical or different time intervals), to a patient as separate entities, wherein such administration provides two or more prophylactically or therapeutically effective active agents in the patient. In some embodiments, the anti-CLDN18.2 antibody or the fragment thereof and the additional therapeutic agent used in the pharmaceutical combination are administered at levels that do not exceed their levels when used alone. The term "fixed combination" means that two or more active agents are administered to a patient simultaneously in the form of a single entity. The dose and/or time intervals of two or more active agents are preferably selected such that the combined use of the components can result in a therapeutic effect on the disease or disorder which is greater than that achieved by the use of either component alone. The ingredients may each take a separate formulation form and such separate formulation forms may be the same or different.

The term "combination therapy" refers to the administration of two or more therapeutic agents or modalities (e.g., radiotherapy or surgery) to treat the diseases as described herein. Such administration includes co-administration of these therapeutic agents in a substantially simultaneous manner, for example, in a single capsule with a fixed proportion of active ingredients. Alternatively, such administration includes co-administration of the active ingredients in a variety of or separate containers (such as tablets, capsules, powder and liquid). The powder and/or liquid can be reconstituted or diluted to a desired dose before administration. In addition, such administration also includes using each type of the therapeutic agents at approximately the same time or in a sequential manner at different times. In any case, the therapeutic regimen will provide the beneficial effect of the pharmaceutical combination in the treatment of disorders or symptoms described herein.

As used herein, "treatment" (or "treat" or "treating") refers to slowing, interrupting, arresting, alleviating, stopping, lowering, or reversing the progression or severity of an existing symptom, disorder, condition, or disease.

As used herein, "prevention" (or "prevent" or "preventing") includes the inhibition of the development or progression of symptoms of a disease or disorder, or a specific disease or disorder.

In some embodiments, subjects with family history of cancer are candidates for preventive regimens. Generally, in the context of cancer, the term "prevention" refers to the administration of a drug prior to the onset of signs or symptoms of a cancer, particularly in subjects at risk of cancer.

The term "vector" used herein refers to a nucleic acid molecule capable of proliferating another nucleic acid to which it is linked. The term includes vectors that serve as self-replicating nucleic acid structures as well as vectors binding to the genome of a host cell into which they have been introduced. Some vectors are capable of directing the expression of a nucleic acid to which they are operably linked. Such vectors are called "expression vectors" herein.

"Subject/patient/individual sample" refers to a collection of cells or fluids obtained from a patient or a subject. The source of tissue or cell samples can be solid tissues, e.g., from fresh, frozen and/or preserved organ or tissue samples or biopsy samples or puncture samples; blood or any blood component; body fluids such as cerebrospinal fluids, amniotic fluids, peritoneal fluids, or interstitial fluids; and cells from a subject at any time during pregnancy or development. Tissue samples may comprise compounds which are naturally not mixed with tissues, such as preservatives, anticoagulants, buffers, fixatives, nutrients and antibiotics.

II. Antibodies

In some embodiments, the anti-CLDN18.2 antibody or the antigen-binding fragment thereof of the present invention binds to CLDN18.2 (e.g., human CLDN18.2) with high affinity. In some embodiments, the anti-CLDN18.2 antibody of the present invention specifically binds to CLDN18.2 (e.g., human CLDN18.2), but does not bind to CLDN18.1 (e.g., human CLDN18.1). In some embodiments, the antibody or the antigen-binding fragment thereof of the present invention has a higher binding affinity for human CLDN18.2 than that of a known CLDN18.2 antibody, e.g., zolbetuximab (abbreviated as Zmab) antibody. In some embodiments, the affinity of the antibody is determined by bio-layer interferometry or surface plasmon resonance.

In some embodiments, the anti-CLDN18.2 antibody of the present invention binds to human CLDN18.2 with an equilibrium dissociation constant ($K_D$) of less than about 15 nM, preferably less than or equal to about 10 nM, 9.5 nM, 9 nM, 8.5 nM, 8 nM, 7.5 nM, 7 nM, 6.5 nM, 6 nM, 5.5 nM, 5 nM, 4.5 nM, 4 nM, 3.5 nM or 3 nM, and in some embodiments, the $K_D$ is between the aforementioned values (including endpoints).

In some embodiments, the antibody or the antigen-binding fragment thereof of the present invention binds to CLDN18.2 on cell surface. In some embodiments, the antibody or the antigen-binding fragment thereof of the present invention does not bind to CLDN18.1 on cell surface. In some embodiments, CLDN18.2 is expressed or overexpressed on cell surface. In some embodiments, the cell is a CHO cell or a 293 cell expressing CLDN18.2, e.g., a CHO-S cell or a HEK293 cell. In some embodiments, the cell is a cancer cell expressing CLDN18.2, e.g., a cell naturally expressing CLDN18.2 or artificially transfected to express CLDN18.2 or artificially transfected to have an increased expression level of CLDN18.2, e.g., a gastric cancer cell line or a pancreatic cancer cell line expressing CLDN18.2, such as NUGC-4, KATO III and DAN-G cell lines, e.g., KATO III and DAN-G cell lines that overexpress CLDN18.2.

In some embodiments, the binding is determined by flow cytometry. In some embodiments, the antibody of the present invention binds to CLDN18.2 overexpressed on CHO cells with an $EC_{50}$ of less than or equal to about 15 nM, 10 nM, 9 nM, 8 nM, 7 nM, 6 nM or 5.5 nM. In some embodiments, the antibody of the present invention binds to a cancer cell expressing CLDN18.2, e.g., a gastric cancer cell line or a pancreatic cancer cell line expressing CLDN18.2, such as NUGC-4, KATO III and DAN-G cell lines, e.g., KATO III and DAN-G cell lines that overexpress CLDN18.2, with an $EC_{50}$ of less than or equal to about 4 nM, 3.7 nM, 3.5 nM, 3 nM, 2.5 nM, 2 nM, 1.5 nM, 1 nM, 0.9 nM, 0.8 nM, 0.7 nM or 0.6 nM. In some embodiments, the antibody of the present invention have an $EC_{50}$ for binding to a cell expressing CLDN18.2 that is comparable to, or less than, the $EC_{50}$ of the known antibody, e.g., Zmab, or less than 75%, 70%, 65%, 60%, 55%, 50%, 45%, 40%, 35%, 30%, 25%, 20% or 15% of the $EC_{50}$ of the known antibody Zmab.

In some embodiments, the antibody or the antigen-binding fragment thereof of the present invention has ADCC activity or CDC activity, e.g., ADCC activity or CDC activity comparable to or higher than that of the known antibody (e.g., Zmab).

In some embodiments, the antibody or the antigen-binding fragment thereof of the present invention is capable of inhibiting a tumor cell, e.g., a tumor cell expressing CLDN18.2.

In some embodiments, the antibody or the antigen-binding fragment thereof of the present invention can be used to treat cancers. In some embodiments, the antibody or the antigen-binding fragment thereof of the present invention is capable of effectively inhibiting tumor growth with a tumor growth inhibition of greater than or equal to about 25%, 30%, 35%, 40%, 45%, 50%, 55%, 60%, 65% or 70%.

In some embodiments, the anti-CLDN18.2 antibody or the antigen-binding fragment thereof of the present invention comprises 3 complementarity determining regions from a heavy chain variable region (HCDRs): HCDR1, HCDR2 and HCDR3.

In some embodiments, the anti-CLDN18.2 antibody or the antigen-binding fragment thereof of the present invention comprises 3 complementarity determining regions from a light chain variable region (LCDRs): LCDR1, LCDR2 and LCDR3.

In some embodiments, the anti-CLDN18.2 antibody or the antigen-binding fragment thereof of the present invention comprises 3 complementarity determining regions from a heavy chain variable region (HCDRs) and 3 complementarity determining regions from a light chain variable region (LCDRs).

In some aspects, the anti-CLDN18.2 antibody or the antigen-binding fragment thereof of the present invention comprises a heavy chain variable region (VH). In some aspects, the anti-CLDN18.2 antibody or the antigen-binding fragment thereof of the present invention comprises a light chain variable region (VL). In some aspects, the anti-CLDN18.2 antibody or the antigen-binding fragment thereof of the present invention comprises a heavy chain variable region (VH) and a light chain variable region (VL). In some embodiments, the heavy chain variable region comprises 3 complementarity determining regions (CDRs) from the heavy chain variable region: HCDR1, HCDR2 and HCDR3. In some embodiments, the light chain variable region comprises 3 complementarity determining regions (CDRs) from the light chain variable region: LCDR1, LCDR2 and LCDR3.

In some embodiments, the anti-CLDN18.2 antibody or the antigen-binding fragment thereof of the present invention further comprises an antibody heavy chain constant region HC. In some embodiments, the anti-CLDN18.2 antibody or the antigen-binding fragment thereof of the present invention further comprises an antibody light chain constant region LC. In some embodiments, the anti-CLDN18.2 antibody or the antigen-binding fragment thereof of the present invention further comprises a heavy chain constant region HC and a light chain constant region LC.

In some embodiments, the heavy chain variable region of the present invention

- (i) comprises or consists of an amino acid sequence having at least 90%, 91%, 92%, 93%, 94%, 95%, 96%, 97%, 98% or 99% identity to an amino acid sequence selected from SEQ ID NOs: 4, 15, 21, 26, 27, 36, 37, 45, 48, 53, 56, 61, 66, 72, 73, 80 and 85; or
- (ii) comprises or consists of an amino acid sequence selected from SEQ ID NOs: 4, 15, 21, 26, 27, 36, 37, 45, 48, 53, 56, 61, 66, 72, 73, 80 and 85; or
- (iii) comprises or consists of an amino acid sequence having one or more (preferably no more than 10, and more preferably no more than 5, 4, 3, 2 or 1) amino acid changes (preferably amino acid replacements, and more preferably amino acid conservative replacements) as compared to an amino acid sequence selected from SEQ ID NOs: 4, 15, 21, 26, 27, 36, 37, 45, 48, 53, 56, 61, 66, 72, 73, 80 and 85, wherein preferably, the amino acid changes do not occur in CDRs.

In some embodiments, the light chain variable region of the present invention

- (i) comprises or consists of an amino acid sequence having at least 90%, 91%, 92%, 93%, 94%, 95%, 96%, 97%, 98% or 99% identity to an amino acid sequence selected from SEQ ID NOs: 9, 19, 22, 31, 32, 40, 41, 47, 49, 55, 57, 65, 68, 75, 76, 83 and 86; or
- (ii) comprises or consists of an amino acid sequence selected from SEQ ID NOs: 9, 19, 22, 31, 32, 40, 41, 47, 49, 55, 57, 65, 68, 75, 76, 83 and 86; or
- (iii) comprises or consists of an amino acid sequence having one or more (preferably no more than 10, and more preferably no more than 5, 4, 3, 2 or 1) amino acid changes (preferably amino acid replacements, and more preferably amino acid conservative replacements) as compared to an amino acid sequence selected from SEQ ID NOs: 9, 19, 22, 31, 32, 40, 41, 47, 49, 55, 57, 65, 68, 75, 76, 83 and 86, wherein preferably, the amino acid changes do not occur in CDRs.

In some embodiments, the 3 complementarity determining regions from a heavy chain variable region (HCDRs) of the present invention, HCDR1, HCDR2 and HCDR3, are selected from

- (i) three complementarity determining regions HCDR1, HCDR2 and HCDR3 contained in a VH set forth in SEQ ID NO: 4,
- (ii) three complementarity determining regions HCDR1, HCDR2 and HCDR3 contained in a VH set forth in SEQ ID NO: 15 or 21,
- (iii) three complementarity determining regions HCDR1, HCDR2 and HCDR3 contained in a VH set forth in SEQ ID NO: 26 or 27,
- (iv) three complementarity determining regions HCDR1, HCDR2 and HCDR3 contained in a VH set forth in SEQ ID NO: 36 or 37,
- (v) three complementarity determining regions HCDR1, HCDR2 and HCDR3 contained in a VH set forth in SEQ ID NO: 45 or 48,
- (vi) three complementarity determining regions HCDR1, HCDR2 and HCDR3 contained in a VH set forth in SEQ ID NO: 53 or 56,
- (vii) three complementarity determining regions HCDR1, HCDR2 and HCDR3 contained in a VH set forth in SEQ ID NO: 61 or 66,
- (viii) three complementarity determining regions HCDR1, HCDR2 and HCDR3 contained in a VH set forth in SEQ ID NO: 72 or 73,
- (ix) three complementarity determining regions HCDR1, HCDR2 and HCDR3 contained in a VH set forth in SEQ ID NO: 80 or 85, and
- (x) relative to the sequence of any one of (i)-(ix), a sequence comprising a total of at least one and no more than 5, 4, 3, 2, or 1 amino acid change (preferably amino acid replacement, and more preferably conservative replacement) in the three HCDRs.

In some embodiments, the 3 complementarity determining regions from a light chain variable region (LCDRs) of the present invention, LCDR1, LCDR2, and LCDR3, are selected from

- (i) three complementarity determining regions LCDR1, LCDR2 and LCDR3 contained in a VL set forth in SEQ ID NO: 9,
- (ii) three complementarity determining regions LCDR1, LCDR2 and LCDR3 contained in a VL set forth in SEQ ID NO: 19 or 22,
- (iii) three complementarity determining regions LCDR1, LCDR2 and LCDR3 contained in a VL set forth in SEQ ID NO: 31 or 32,
- (iv) three complementarity determining regions LCDR1, LCDR2 and LCDR3 contained in a VL set forth in SEQ ID NO: 40 or 41,
- (v) three complementarity determining regions LCDR1, LCDR2 and LCDR3 contained in a VL set forth in SEQ ID NO: 47 or 49,
- (vi) three complementarity determining regions LCDR1, LCDR2 and LCDR3 contained in a VL set forth in SEQ ID NO: 55 or 57,
- (vii) three complementarity determining regions LCDR1, LCDR2 and LCDR3 contained in a VL set forth in SEQ ID NO: 65 or 68,
- (viii) three complementarity determining regions LCDR1, LCDR2 and LCDR3 contained in a VL set forth in SEQ ID NO: 75 or 76,
- (ix) three complementarity determining regions LCDR1, LCDR2 and LCDR3 contained in a VL set forth in SEQ ID NO: 83 or 86, and
- (x) relative to the sequence of any one of (i)-(ix), a sequence comprising a total of at least one and no more than 5, 4, 3, 2, or 1 amino acid change (preferably amino acid replacement, and more preferably conservative replacement) in the three LCDRs.

In some embodiments, the HCDR1 comprises or consists of an amino acid sequence set forth in SEQ ID NO: 1, 12, 23, 33, 42, 50, 58, 69 or 77, or the HCDR1 comprises an amino acid sequence having one, two or three changes (preferably amino acid replacements, and more preferably conservative replacements) as compared to the amino acid sequence set forth in SEQ ID NO: 1, 12, 23, 33, 42, 50, 58, 69 or 77.

In some embodiments, the HCDR2 comprises or consists of an amino acid sequence set forth in SEQ ID NO: 2, 13, 20, 24, 34, 43, 51, 59, 70, 78, 84, 93 or 94, or the HCDR2 comprises an amino acid sequence having one, two or three changes (preferably amino acid replacements, and more preferably conservative replacements) as compared to the amino acid sequence set forth in SEQ ID NO: 2, 13, 20, 24, 34, 43, 51, 59, 70, 78, 84, 93 or 94, wherein the SEQ ID NO: 93 is YIAPFXGDSRYNQKFKG, where X is any amino acid, preferably N or Q or a conservative amino acid substitution thereof; or the SEQ ID NO: 94 is VIWGDXSTNYHSVLIS, where X is any amino acid, preferably G or V or a conservative amino acid substitution thereof.

In some embodiments, the HCDR3 comprises or consists of an amino acid sequence set forth in SEQ ID NO: 3, 14, 25, 35, 44, 52, 60, 71 or 79, or the HCDR3 comprises an amino acid sequence having one, two or three changes (preferably amino acid replacements, and more preferably conservative replacements) as compared to the amino acid sequence set forth in SEQ ID NO: 3. 14, 25, 35, 44, 52, 60, 71 or 79.

In some embodiments, the LCDR1 comprises or consists of an amino acid sequence set forth in SEQ ID NO: 6, 16, 28, 38, 62, 67 or 11, or the LCDR1 comprises an amino acid sequence having one, two or three changes (preferably amino acid replacements, and more preferably conservative replacements) as compared to the amino acid sequence set forth in SEQ ID NO: 6. 16, 28, 38, 62, 67 or 11;

wherein the SEQ ID NO: 11 is KSSQSLLXGGNQKNYLT, where X is any amino acid, preferably N or Q or a conservative amino acid substitution thereof.

In some embodiments, the LCDR2 comprises or consists of an amino acid sequence set forth in SEQ ID NO: 7, 17, 29, 63 or 81, or the LCDR2 comprises an amino acid sequence having one, two or three changes (preferably amino acid replacements, and more preferably conservative replacements) as compared to the amino acid sequence set forth in SEQ ID NO: 7, 17, 29, 63 or 81.

In some embodiments, the LCDR3 comprises or consists of an amino acid sequence set forth in SEQ ID NO: 8, 18, 30, 39, 46, 54, 64, 74 or 82, or the LCDR3 comprises an amino acid sequence having one, two or three changes (preferably amino acid replacements, and more preferably conservative replacements) as compared to the amino acid sequence set forth in SEQ ID NO: 8, 18, 30, 39, 46, 54, 64, 74 or 82.

In some embodiments, the antibody heavy chain constant region HC of the present invention is a heavy chain constant region of IgG1, IgG2, IgG3 or IgG4, preferably a heavy chain constant region of IgG1. In some embodiments, the antibody light chain constant region LC of the present invention is a lambda or kappa light chain constant region, preferably a kappa light chain constant region.

In some preferred embodiments, the antibody heavy chain constant region HC of the present invention (i) comprises or consists of an amino acid sequence having at least 85%, 90%, 91%, 92%, 93%, 94%, 95%, 96%, 97%, 98% or 99% identity to an amino acid sequence selected from SEQ ID NO: 5;

(ii) comprises or consists of an amino acid sequence selected from SEQ ID NO: 5; or (iii) comprises or consists of an amino acid sequence having one or more (preferably no more than 20 or 10, and more preferably no more than 5, 4, 3, 2 or 1) amino acid changes (preferably amino acid replacements, and more preferably amino acid conservative replacements) as compared to an amino acid sequence selected from SEQ ID NO: 5.

In some embodiments, the amino acid change occurs in an Fc region. In one embodiment, the amino acid change in the Fc region increases the CDC or ADCC activity of the antibody.

In some embodiments, the antibody light chain constant region LC of the present invention (i) comprises or consists of an amino acid sequence having at least 85%, 90%, 91%, 92%, 93%, 94%, 95%, 96%, 97%, 98% or 99% identity to an amino acid sequence selected from SEQ ID NO: 10;

(ii) comprises or consists of an amino acid sequence selected from SEQ ID NO: 10; or (iii) comprises or consists of an amino acid sequence having one or more (preferably no more than 20 or 10, and more preferably no more than 5, 4, 3, 2 or 1) amino acid changes (preferably amino acid replacements, and more preferably amino acid conservative replacements) as compared to an amino acid sequence selected from SEQ ID NO: 10.

In some specific embodiments of the present invention, the anti-CLDN18.2 antibody or the antigen-binding fragment thereof of the present invention comprises:

(i) three complementarity determining regions HCDR1, HCDR2 and HCDR3 contained in a VH set forth in SEQ ID NO: 4, and three complementarity determining regions LCDR1, LCDR2 and LCDR3 contained in a VL set forth in SEQ ID NO: 9;

(ii) three complementarity determining regions HCDR1, HCDR2 and HCDR3 contained in a VH set forth in SEQ ID NO: 15 or 21, and three complementarity determining regions LCDR1, LCDR2 and LCDR3 contained in a VL set forth in SEQ ID NO: 19 or 22;

(iii) three complementarity determining regions HCDR1, HCDR2 and HCDR3 contained in a VH set forth in SEQ ID NO: 26 or 27, and three complementarity determining regions LCDR1, LCDR2 and LCDR3 contained in a VL set forth in SEQ ID NO: 31 or 32;

(iv) three complementarity determining regions HCDR1, HCDR2 and HCDR3 contained in a VH set forth in SEQ ID NO: 36 or 37, and three complementarity determining regions LCDR1, LCDR2 and LCDR3 contained in a VL set forth in SEQ ID NO: 40 or 41;

(v) three complementarity determining regions HCDR1, HCDR2 and HCDR3 contained in a VH set forth in SEQ ID NO: 45 or 48, and three complementarity determining regions LCDR1, LCDR2 and LCDR3 contained in a VL set forth in SEQ ID NO: 47 or 49;

(vi) three complementarity determining regions HCDR1, HCDR2 and HCDR3 contained in a VH set forth in SEQ ID NO: 53 or 56, and three complementarity determining regions LCDR1, LCDR2 and LCDR3 contained in a VL set forth in SEQ ID NO: 55 or 57;

(vii) three complementarity determining regions HCDR1, HCDR2 and HCDR3 contained in a VH set forth in SEQ ID NO: 61 or 66, and three complementarity determining regions LCDR1, LCDR2 and LCDR3 contained in a VL set forth in SEQ ID NO: 65 or 68;

(viii) three complementarity determining regions HCDR1, HCDR2 and HCDR3 contained in a VH set forth in SEQ ID NO: 72 or 73, and three complementarity determining regions LCDR1, LCDR2 and LCDR3 contained in a VL set forth in SEQ ID NO: 75 or 76;

(ix) three complementarity determining regions HCDR1, HCDR2 and HCDR3 contained in a VH set forth in SEQ ID NO: 80 or 85, and three complementarity determining regions LCDR1, LCDR2 and LCDR3 contained in a VL set forth in SEQ ID NO: 83 or 86.

In some specific embodiments of the present invention, the anti-CLDN18.2 antibody or the antigen-binding fragment thereof of the present invention comprises:

(i) HCDR1, HCDR2 and HCDR3 set forth in amino acid sequences of SEQ ID NOs: 1, 2 and 3, respectively, and LCDR1, LCDR2 and LCDR3 set forth in amino acid sequences of SEQ ID NOs: 6, 7 and 8, respectively;

(ii) HCDR1, HCDR2 and HCDR3 set forth in amino acid sequences of SEQ ID NOs: 12, 13 and 14, respectively, and LCDR1, LCDR2 and LCDR3 set forth in amino acid sequences of SEQ ID NOs: 16, 17 and 18, respectively;

(iii) HCDR1, HCDR2 and HCDR3 set forth in amino acid sequences of SEQ ID NOs: 12, 20 and 14, respectively, and LCDR1, LCDR2 and LCDR3 set forth in amino acid sequences of SEQ ID NOs: 16, 17 and 18, respectively;

(iv) HCDR1, HCDR2 and HCDR3 set forth in amino acid sequences of SEQ ID NOs: 12, 93 and 14, respectively, and LCDR1, LCDR2 and LCDR3 set forth in amino acid sequences of SEQ ID NOs: 16, 17 and 18, respectively;

(v) HCDR1, HCDR2 and HCDR3 set forth in amino acid sequences of SEQ ID NOs: 23, 24 and 25, respectively, and LCDR1, LCDR2 and LCDR3 set forth in amino acid sequences of SEQ ID NOs: 28, 29 and 30, respectively;

(vi) HCDR1, HCDR2 and HCDR3 set forth in amino acid sequences of SEQ ID NOs: 33, 34 and 35, respectively, and LCDR1, LCDR2 and LCDR3 set forth in amino acid sequences of SEQ ID NOs: 38, 17 and 39, respectively;

(vii) HCDR1, HCDR2 and HCDR3 set forth in amino acid sequences of SEQ ID NOs: 42, 43 and 44, respectively, and LCDR1, LCDR2 and LCDR3 set forth in amino acid sequences of SEQ ID NOs: 38, 17 and 46, respectively;

(viii) HCDR1, HCDR2 and HCDR3 set forth in amino acid sequences of SEQ ID NOs: 50, 51 and 52, respectively, and LCDR1, LCDR2 and LCDR3 set forth in amino acid sequences of SEQ ID NOs: 28, 17 and 54, respectively;

(ix) HCDR1, HCDR2 and HCDR3 set forth in amino acid sequences of SEQ ID NOs: 58, 59 and 60, respectively, and LCDR1, LCDR2 and LCDR3 set forth in amino acid sequences of SEQ ID NOs: 62, 63 and 64, respectively;

(x) HCDR1, HCDR2 and HCDR3 set forth in amino acid sequences of SEQ ID NOs: 58, 59 and 60, respectively, and LCDR1, LCDR2 and LCDR3 set forth in amino acid sequences of SEQ ID NOs: 67, 63 and 64, respectively;

(xi) HCDR1, HCDR2 and HCDR3 set forth in amino acid sequences of SEQ ID NOs: 58, 59 and 60, respectively, and LCDR1, LCDR2 and LCDR3 set forth in amino acid sequences of SEQ ID NOs: 11, 63 and 64, respectively;

(xii) HCDR1, HCDR2 and HCDR3 set forth in amino acid sequences of SEQ ID NOs: 69, 70 and 71, respectively, and LCDR1, LCDR2 and LCDR3 set forth in amino acid sequences of SEQ ID NOs: 38, 17 and 74, respectively;

(xiii) HCDR1, HCDR2 and HCDR3 set forth in amino acid sequences of SEQ ID NOs: 77, 78 and 79, respectively, and LCDR1, LCDR2 and LCDR3 set forth in amino acid sequences of SEQ ID NOs: 28, 81 and 82, respectively;

(xiv) HCDR1, HCDR2 and HCDR3 set forth in amino acid sequences of SEQ ID NOs: 77, 84 and 79, respectively, and LCDR1, LCDR2 and LCDR3 set forth in amino acid sequences of SEQ ID NOs: 28, 81 and 82, respectively;

(xv) HCDR1, HCDR2 and HCDR3 set forth in amino acid sequences of SEQ ID NOs: 77, 94 and 79, respectively, and LCDR1, LCDR2 and LCDR3 set forth in amino acid sequences of SEQ ID NOs: 28, 81 and 82, respectively.

In some specific embodiments of the present invention, the anti-CLDN18.2 antibody or the antigen-binding fragment thereof of the present invention comprises:

(i) a VH comprising or consisting of an amino acid sequence set forth in SEQ ID NO: 4 or an amino acid sequence having at least 90% identity thereto, and a VL comprising or consisting of an amino acid sequence set forth in SEQ ID NO: 9 or an amino acid sequence having at least 90% identity thereto;

(ii) a VH comprising or consisting of an amino acid sequence set forth in SEQ ID NO: 15 or 21 or an amino acid sequence having at least 90% identity thereto, and a VL comprising or consisting of an amino acid sequence set forth in SEQ ID NO: 19 or 22 or an amino acid sequence having at least 90% identity thereto;

(iii) a VH comprising or consisting of an amino acid sequence set forth in SEQ ID NO: 15 or an amino acid sequence having at least 90% identity thereto, and a VL comprising or consisting of an amino acid sequence set forth in SEQ ID NO: 19 or an amino acid sequence having at least 90% identity thereto;

(iv) a VH comprising or consisting of an amino acid sequence set forth in SEQ ID NO: 21 or an amino acid sequence having at least 90% identity thereto, and a VL comprising or consisting of an amino acid sequence set forth in SEQ ID NO: 22 or an amino acid sequence having at least 90% identity thereto;

(v) a VH comprising or consisting of an amino acid sequence set forth in SEQ ID NO: 26 or 27 or an amino acid sequence having at least 90% identity thereto, and a VL comprising or consisting of an amino acid sequence set forth in SEQ ID NO: 31 or 32 or an amino acid sequence having at least 90% identity thereto;

(vi) a VH comprising or consisting of an amino acid sequence set forth in SEQ ID NO: 26 or an amino acid sequence having at least 90% identity thereto, and a VL comprising or consisting of an amino acid sequence set forth in SEQ ID NO: 31 or an amino acid sequence having at least 90% identity thereto;

(vii) a VH comprising or consisting of an amino acid sequence set forth in SEQ ID NO: 27 or an amino acid sequence having at least 90% identity thereto, and a VL comprising or consisting of an amino acid sequence set forth in SEQ ID NO: 32 or an amino acid sequence having at least 90% identity thereto;

(viii) a VH comprising or consisting of an amino acid sequence set forth in SEQ ID NO: 36 or 37 or an amino acid sequence having at least 90% identity thereto, and a VL comprising or consisting of an amino acid sequence set forth in SEQ ID NO: 40 or 41 or an amino acid sequence having at least 90% identity thereto;

(ix) a VH comprising or consisting of an amino acid sequence set forth in SEQ ID NO: 36 or an amino acid sequence having at least 90% identity thereto, and a VL comprising or consisting of an amino acid sequence set forth in SEQ ID NO: 40 or an amino acid sequence having at least 90% identity thereto;

(x) a VH comprising or consisting of an amino acid sequence set forth in SEQ ID NO: 37 or an amino acid sequence having at least 90% identity thereto, and a VL comprising or consisting of an amino acid sequence set forth in SEQ ID NO: 41 or an amino acid sequence having at least 90% identity thereto;

(xi) a VH comprising or consisting of an amino acid sequence set forth in SEQ ID NO: 45 or 48 or an amino acid sequence having at least 90% identity thereto, and a VL comprising or consisting of an amino acid sequence set forth in SEQ ID NO: 47 or 49 or an amino acid sequence having at least 90% identity thereto;

(xii) a VH comprising or consisting of an amino acid sequence set forth in SEQ ID NO: 45 or an amino acid sequence having at least 90% identity thereto, and a VL comprising or consisting of an amino acid sequence set forth in SEQ ID NO: 47 or an amino acid sequence having at least 90% identity thereto;

(xiii) a VH comprising or consisting of an amino acid sequence set forth in SEQ ID NO: 48 or an amino acid sequence having at least 90% identity thereto, and a VL comprising or consisting of an amino acid sequence set forth in SEQ ID NO: 49 or an amino acid sequence having at least 90% identity thereto;

(xiv) a VH comprising or consisting of an amino acid sequence set forth in SEQ ID NO: 53 or 56 or an amino acid sequence having at least 90% identity thereto, and a VL comprising or consisting of an amino acid sequence set forth in SEQ ID NO: 55 or 57 or an amino acid sequence having at least 90% identity thereto;

(xv) a VH comprising or consisting of an amino acid sequence set forth in SEQ ID NO: 53 or an amino acid sequence having at least 90% identity thereto, and a VL comprising or consisting of an amino acid sequence set forth in SEQ ID NO: 55 or an amino acid sequence having at least 90% identity thereto;

(xvi) a VH comprising or consisting of an amino acid sequence set forth in SEQ ID NO: 56 or an amino acid sequence having at least 90% identity thereto, and a VL comprising or consisting of an amino acid sequence set forth in SEQ ID NO: 57 or an amino acid sequence having at least 90% identity thereto;

(xvii) a VH comprising or consisting of an amino acid sequence set forth in SEQ ID NO: 61 or 66 or an amino acid sequence having at least 90% identity thereto, and a VL comprising or consisting of an amino acid sequence set forth in SEQ ID NO: 65 or 68 or an amino acid sequence having at least 90% identity thereto;

(xviii) a VH comprising or consisting of an amino acid sequence set forth in SEQ ID NO: 61 or an amino acid sequence having at least 90% identity thereto, and a VL comprising or consisting of an amino acid sequence set forth in SEQ ID NO: 65 or an amino acid sequence having at least 90% identity thereto;

(xix) a VH comprising or consisting of an amino acid sequence set forth in SEQ ID NO: 66 or an amino acid sequence having at least 90% identity thereto, and a VL comprising or consisting of an amino acid sequence set forth in SEQ ID NO: 68 or an amino acid sequence having at least 90% identity thereto;

(xx) a VH comprising or consisting of an amino acid sequence set forth in SEQ ID NO: 72 or 73 or an amino acid sequence having at least 90% identity thereto, and a VL comprising or consisting of an amino acid sequence set forth in SEQ ID NO: 75 or 76 or an amino acid sequence having at least 90% identity thereto;

(xxi) a VH comprising or consisting of an amino acid sequence set forth in SEQ ID NO: 72 or an amino acid sequence having at least 90% identity thereto, and a VL comprising or consisting of an amino acid sequence set forth in SEQ ID NO: 75 or an amino acid sequence having at least 90% identity thereto;

(xxii) a VH comprising or consisting of an amino acid sequence set forth in SEQ ID NO: 73 or an amino acid sequence having at least 90% identity thereto, and a VL comprising or consisting of an amino acid sequence set forth in SEQ ID NO: 76 or an amino acid sequence having at least 90% identity thereto;

(xxiii) a VH comprising or consisting of an amino acid sequence set forth in SEQ ID NO: 80 or 85 or an amino acid sequence having at least 90% identity thereto, and a VL comprising or consisting of an amino acid sequence set forth in SEQ ID NO: 83 or 86 or an amino acid sequence having at least 90% identity thereto;

(xxiv) a VH comprising or consisting of an amino acid sequence set forth in SEQ ID NO: 80 or an amino acid sequence having at least 90% identity thereto, and a VL comprising or consisting of an amino acid sequence set forth in SEQ ID NO: 83 or an amino acid sequence having at least 90% identity thereto;

(xxv) a VH comprising or consisting of an amino acid sequence set forth in SEQ ID NO: 85 or an amino acid sequence having at least 90% identity thereto, and a VL comprising or consisting of an amino acid sequence set forth in SEQ ID NO: 86 or an amino acid sequence having at least 90% identity thereto.

In one embodiment of the present invention, the amino acid change described herein includes amino acid replacement, insertion or deletion. Preferably, the amino acid change described herein is an amino acid replacement, preferably a conservative replacement.

In a preferred embodiment, the amino acid change described herein occurs in a region outside the CDRs (e.g., in FR). More preferably, the amino acid change described herein occurs in a region outside the heavy chain variable region and/or outside the light chain variable region. In some embodiments, the amino acid change described herein occurs in the Fc region of the antibody heavy chain constant region. In preferred embodiments, the amino acid change in the Fc region increases the ADCC and/or CDC effect of the antibody.

In some embodiments, the replacement is a conservative replacement. A conservative replacement refers to the replacement of an amino acid by another amino acid of the same class, e.g., the replacement of an acidic amino acid by another acidic amino acid, the replacement of a basic amino acid by another basic amino acid, or the replacement of a neutral amino acid by another neutral amino acid. Exemplary replacements are shown in table below:

| Original residues | Exemplary replacement | Preferred conservative amino acid replacement |
|---|---|---|
| Ala (A) | Val, Leu, Ile | Val |
| Arg (R) | Lys, Gln, Asn | Lys |

-continued

| Original residues | Exemplary replacement | Preferred conservative amino acid replacement |
|---|---|---|
| Asn (N) | Gln, His, Asp, Lys, Arg | Gln |
| Asp (D) | Glu, Asn | Glu |
| Cys (C) | Ser, Ala | Ser |
| Gln (Q) | Asn, Glu | Asn |
| Glu (E) | Asp, Gln | Asp |
| Gly (G) | Ala | Ala |
| His (H) | Asn, Gln, Lys, Arg | Arg |
| Ile (I) | Leu, Val, Met, Ala, Phe, Nle | Leu |
| Leu (L) | Nle, Ile, Val, Met, Ala, Phe | Ile |
| Lys (K) | Arg, Gln, Asn | Arg |
| Met (M) | Leu, Phe, Ile | Leu |
| Phe (F) | Trp, Leu, Val, Ile, Ala, Tyr | Tyr |
| Pro (P) | Ala | Ala |
| Ser (S) | Thr | Thr |
| Thr (T) | Val, Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Nle | Leu |

In certain embodiments, the replacement occurs in the CDRs of the antibody. Generally, the obtained variant has modifications (e.g., improvements) in certain biological properties (e.g., increased affinity) relative to the parent antibody and/or will substantially retain certain biological properties of the parent antibody. Exemplary replacement variants are affinity-matured antibodies.

In certain embodiments, the antibody provided herein is altered to increase or decrease the extent to which the antibody is glycosylated. Addition or deletion of glycosylation sites of an antibody can be conveniently achieved by altering the amino acid sequence to create or remove one or more glycosylation sites. When the antibody comprises an Fc region, carbohydrate attached thereto can be altered. In some applications, modifications that remove undesired glycosylation sites may be useful, for example, removing fucose motif to enhance antibody-dependent cell-mediated cytotoxicity (ADCC) function (see Shield, et al. (2002) JBC277:26733). In other applications, galactosidylation modification can be carried out to modify complement-dependent cytotoxicity (CDC).

In certain embodiments, one or more amino acid modifications may be introduced into the Fc region of the antibody provided herein, thereby producing an Fc region variant to alter one or more functional properties of the antibody, such as serum half-life, complement fixation, complement-dependent cytotoxicity, Fc receptor binding and/or antibody-dependent cell-mediated cytotoxicity. The Fc region variant may comprise a human Fc region sequence (such as human IgG1, IgG2, IgG3 or IgG4 Fc region) comprising an amino acid change (e.g., replacement) at one or more amino acid positions.

In one embodiment of the present invention, changes are introduced in the Fc region of the antibody described herein to increase the ADCC activity or CDC activity of the antibody.

In certain embodiments, antibodies modified by cysteine engineering may need to be produced, such as "sulfo-MAb", wherein one or more residues of the antibodies are replaced by cysteine residues.

In certain embodiments, the antibody provided herein can be further modified to comprise other non-protein portions known in the art and readily available. Suitable portions for antibody derivatization include, but are not limited to, water-soluble polymers. Non-limiting examples of water-soluble polymers include, but are not limited to, polyethylene glycol (PEG), ethylene glycol/propylene glycol copolymer, carboxymethyl cellulose, glucan, polyvinyl alcohol, polyvinylpyrrolidone, poly-1,3-dioxane, poly-1,3,6-trioxane, ethylene/maleic anhydride copolymer, polyamino acid (homopolymer or random copolymer), and glucan or poly(n-vinylpyrrolidone)polyethylene glycol, propylene glycol homopolymer, polypropylene oxide/ethylene oxide copolymer, polyoxyethylated polyol (e.g., glycerol), polyvinyl alcohol and mixtures thereof.

In some embodiments, the anti-CLDN18.2 antibody or the antigen-binding fragment thereof of the present invention has one or more of the following properties:

(i) showing the same or similar binding affinity and/or specificity for CLDN18.2 as the antibody of the present invention;

(ii) inhibiting (e.g., competitively inhibiting) the binding of the antibody of the present invention to CLDN18.2;

(iii) binding to the same or overlapping epitope as the antibody of the present invention;

(iv) competing with the antibody of the present invention for binding to CLDN18.2;

(v) having one or more biological properties of the antibody of the present invention.

In some embodiments, the anti-CLDN18.2 antibody of the present invention is an antibody in the form of IgG1, IgG2, IgG3 or IgG4, preferably an antibody in the form of IgG1.

In some embodiments, the anti-CLDN18.2 antibody is a monoclonal antibody.

In some embodiments, the anti-CLDN18.2 antibody is a humanized antibody.

In some embodiments, the anti-CLDN18.2 antibody is a human antibody.

In some embodiments, the anti-CLDN18.2 antibody is a chimeric antibody.

In some embodiments, at least a portion of the framework sequence of the anti-CLDN18.2 antibody is a human consensus framework sequence.

In one embodiment, the anti-CLDN18.2 antibody of the present invention also encompasses an antibody fragment (e.g., an antigen-binding fragment) thereof, preferably an antibody fragment selected from: Fab, Fab', Fab'-SH, Fv, a single-chain antibody (e.g., scFv), $(Fab')_2$, a single-domain antibody (e.g., VHH), a domain antibody (dAb) and a linear antibody.

III. Nucleic Acid of the Present Invention and Host Cell Comprising Same

In one aspect, the present invention provides a nucleic acid encoding any of the aforementioned anti-CLDN18.2 antibodies or the fragments thereof. In one embodiment, provided is a vector comprising the nucleic acid. In one embodiment, the vector is an expression vector, e.g., pcDNA3.1. In one embodiment, provided is a host cell comprising the nucleic acid or the vector. In one embodiment, the host cell is eukaryotic. In another embodiment, the host cell is selected from yeast cells, mammalian cells (e.g., CHO cells (e.g., CHO-S) or 293 cells (e.g., 293F or HEK293 cells)), or additional cells suitable for producing an antibody or a fragment thereof. In another embodiment, the host cell is prokaryotic.

In one aspect, the present invention provides a nucleic acid encoding any of the anti-CLDN18.2 antibodies or the fragments thereof described herein. The nucleic acid can include a nucleic acid encoding an amino acid sequence of the light chain variable region and/or heavy chain variable region of the antibody, or a nucleic acid encoding an amino acid sequence of the light chain and/or heavy chain of the antibody.

For example, the nucleic acid of the present invention comprises a nucleic acid encoding an amino acid sequence selected from any one of SEQ ID NOs: 4, 15, 21, 26, 27, 36, 37, 45, 48, 53, 56, 61, 66, 72, 73, 80 and 85, or SEQ ID NOs: 9, 19, 22, 31, 32, 40, 41, 47, 49, 55, 57, 65, 68, 75, 76, 83 and 86; or a nucleic acid encoding an amino acid sequence having at least 85%, 90%, 91%, 92%, 93%, 94%, 95%, 96%, 97%, 98% or 99% identity to an amino acid sequence selected from any one of SEQ ID NOs: 4, 15, 21, 26, 27, 36, 37, 45, 48, 53, 56, 61, 66, 72, 73, 80 and 85, or SEQ ID NOs: 9, 19, 22, 31, 32, 40, 41, 47, 49, 55, 57, 65, 68, 75, 76, 83 and 86.

The present invention also encompasses a nucleic acid that hybridizes under stringency conditions to, or has one or more replacements (e.g., conservative replacements), deletions or insertions as compared to, a nucleic acid that comprises a nucleic acid sequence encoding an amino acid sequence selected from any one of SEQ ID NOs: 4, 15, 21, 26, 27, 36, 37, 45, 48, 53, 56, 61, 66, 72, 73, 80 and 85, or SEQ ID NOs: 9, 19, 22, 31, 32, 40, 41, 47, 49, 55, 57, 65, 68, 75, 76, 83 and 86; or a nucleic acid that comprises a nucleic acid sequence encoding an amino acid sequence having at least 85%, 90%, 91%, 92%, 93%, 94%, 95%, 96%, 97%, 98% or 99% identity to an amino acid sequence selected from any one of SEQ ID NOs: 4, 15, 21, 26, 27, 36, 37, 45, 48, 53, 56, 61, 66, 72, 73, 80 and 85, or SEQ ID NOs: 9, 19, 22, 31, 32, 40, 41, 47, 49, 55, 57, 65, 68, 75, 76, 83 and 86.

In one embodiment, provided are one or more vectors comprising the nucleic acid. In one embodiment, the vector is an expression vector, such as a eukaryotic expression vector. The vector includes, but is not limited to, a virus, a plasmid, a cosmid, a k phage or a yeast artificial chromosome (YAC). In one embodiment, the vector is pcDNA3.1.

In one embodiment, provided is a host cell comprising the vector. The suitable host cell for cloning or expressing the vector encoding the antibody includes prokaryotic cells or eukaryotic cells described herein. For example, the antibody may be produced in bacteria, particularly when glycosylation and Fc effector functions are not required. After expression, the antibody can be isolated from bacterial cell paste in soluble fraction and can be further purified.

In one embodiment, the host cell is eukaryotic. In another embodiment, the host cell is selected from yeast cells, mammalian cells, and additional cells suitable for producing an antibody or a fragment thereof. For example, eukaryotic microorganisms, such as filamentous fungi or yeast, are suitable cloning or expression hosts for the vector encoding the antibody. For example, fungus and yeast strains in which a glycosylation pathway has been "humanized" may produce antibodies having a partial or full human glycosylation pattern. Host cells suitable for expressing a glycosylated antibody are also derived from multicellular organisms (invertebrates and vertebrates). Vertebrate cells may also be used as hosts. For example, a mammalian cell line engineered to be suitable for suspension growth may be used. Other examples of useful mammalian host cell lines are monkey kidney CV1 line (COS-7) transformed with SV40, human embryonic kidney line (HEK293, 293F or 293T cells), and the like. Other useful mammalian host cell lines include Chinese hamster ovary (CHO) cells, including DHFR-CHO cells, CHO-S cells, ExpiCHO and the like; and myeloma cell lines such as Y0, NS0 and Sp2/0. Mammalian host cell lines suitable for producing antibodies are known in the art.

IV. Production and Purification of the Antibody Molecule of the Present Invention In one embodiment, the present invention provides a method for preparing the antibody molecule or the fragment (preferably the antigen-binding fragment) thereof of the present invention, wherein the method comprises culturing the host cell under conditions suitable for expressing the nucleic acid encoding the antibody molecule or the fragment (preferably the antigen-binding fragment) thereof of the present invention, and optionally isolating the antibody or the fragment (e.g., the antigen-binding fragment) thereof. In a certain embodiment, the method further comprises recovering the antibody molecule or the fragment (e.g., the antigen-binding fragment) thereof of the present invention from the host cell.

In one embodiment, provided is a method for preparing the antibody molecule of the present invention, wherein the method comprises culturing the host cell comprising a nucleic acid encoding the antibody (e.g., any one and/or more polypeptide chains) or an expression vector comprising the nucleic acid, as provided above, under conditions suitable for expressing antibodies, and optionally recovering the antibody from the host cell (or the host cell medium).

For recombinant production of the antibody molecule of the present invention, a nucleic acid encoding the antibody (e.g., the antibody described above, e.g., any one and/or more polypeptide chains) is isolated and inserted into one or more vectors for further cloning and/or expressing in the host cells. Such a nucleic acid can be easily isolated and sequenced by using conventional procedures (e.g., by using oligonucleotide probes that are capable of specifically binding to genes encoding heavy and light chains of antibodies).

The antibody molecule prepared as described herein can be purified by known prior art such as high performance liquid chromatography, ion exchange chromatography, gel electrophoresis, affinity chromatography, and size exclusion chromatography. The actual conditions used to purify a particular protein also depend on factors such as net charge, hydrophobicity and hydrophilicity, and these will be apparent to those skilled in the art. The purity of the antibody molecule of the present invention can be determined by any one of a variety of well-known analytical methods including size exclusion chromatography, gel electrophoresis, high performance liquid chromatography, and the like.

V. Assays

The anti-CLDN18.2 antibody provided herein can be identified, screened, or characterized for physical/chemical properties and/or bioactivity thereof through a variety of assays known in the art. In one aspect, the antibody of the present invention is tested for the antigen-binding activity, for example, by known methods such as ELISA and Western blotting. The binding to CLDN18.2 can be determined by methods known in the art, and exemplary methods are disclosed herein. In some embodiments, the binding is determined by radioimmunoassay (RIA), bio-layer interferometry, MSD assay, surface plasmon resonance (SPR) or flow cytometry.

In another aspect, a competition assay can be used to identify antibodies that compete for binding to CLDN18.2 with any of the anti-CLDN18.2 antibodies disclosed herein.

In certain embodiments, such a competitive antibody binds to the same or an overlapping epitope (e.g., a linear or conformational epitope) as any of the anti-CLDN18.2 antibodies disclosed herein.

The present invention also provides an assay for identifying anti-CLDN18.2 antibody having bioactivities. Bioactivities may include, for example, binding to CLDN18.2 (e.g., binding to human CLDN18.2), binding to cells expressing CLDN18.2, activity for CDC or ADCC of the cells, inhibition of tumor cells, and the like. Further provided is an antibody having such bioactivities in vivo and/or in vitro.

In certain embodiments, the antibody of the present invention is characterized for such bioactivities.

Cells for use in any of the above in vitro assays include cell lines that naturally express CLDN18.2 or are engineered to express or overexpress CLDN18.2. Such cells also include cell lines that express CLDN18.2 and cell lines that do not normally express CLDN18.2 but have been transfected with a DNA encoding CLDN18.2. In some embodiments, such cells are gastric cancer cells or pancreatic cancer cells. In some embodiments, the cells are CHO cells expressing CLDN18.2. In some embodiments, the cells are NUGC-4, KATO III and DAN-G cell lines, such as KATO III and DAN-G cell lines that overexpress CLDN18.2.

It will be appreciated that any of the above assays can be performed by using the immunoconjugate of the present invention in place of or in addition to the anti-CLDN18.2 antibody.

It will be appreciated that any of the above assays can be performed using a combination of the anti-CLDN18.2 antibody and other active agents.

VI. Immunoconjugate

In some embodiments, the present invention provides an immunoconjugate comprising any of the anti-CLDN18.2 antibodies provided herein and additional substances, such as therapeutic agents, including a chemotherapeutic agent, a cytokine, a cytotoxic agent, an additional antibody, a small molecule drug or an immunomodulatory agent (e.g., an anti-inflammatory agent or immunosuppressant). In one embodiment, the additional substances such as cytotoxic agents include any agents that are harmful to cells.

In some embodiments, the immunoconjugate is used to prevent or treat cancers.

VII. Pharmaceutical Compositions and Pharmaceutical Preparations

In some embodiments, the present invention provides a composition comprising any of the anti-CLDN18.2 antibodies or the fragments thereof (preferably the antigen-binding fragments thereof), or the immunoconjugates thereof described herein, wherein, preferably, the composition is a pharmaceutical composition. In one embodiment, the composition further comprises a pharmaceutical supplementary material. In one embodiment, the composition, e.g., the pharmaceutical composition, comprises the anti-CLDN18.2 antibody or the fragment thereof, or the immunoconjugate thereof of the present invention, and a combination of one or more additional therapeutic agents.

The present invention also includes a composition (including a pharmaceutical composition or a pharmaceutical preparation) comprising an anti-CLDN18.2 antibody or an immunoconjugate thereof, or a composition (including a pharmaceutical composition or a pharmaceutical preparation) comprising a polynucleotide encoding the anti-CLDN18.2 antibody. In certain embodiments, the composition comprises one or more antibodies or fragments thereof binding to CLDN18.2, or one or more polynucleotides encoding one or more anti-CLDN18.2 antibodies or fragments thereof. Such compositions can further comprise a suitable pharmaceutical supplementary material, such as a pharmaceutical carrier and a pharmaceutical excipient known in the art, including buffers.

As used herein, the "pharmaceutical carrier" includes any and all solvents, dispersion media, isotonic agents and absorption delaying agents, and the like that are physiologically compatible.

For use and application of pharmaceutical supplementary materials, see *Handbook of Pharmaceutical Excipients,* $8^{th}$ Ed., R. C. Rowe, P. J. Seskey and S. C. Owen, Pharmaceutical Press, London, Chicago.

The compositions of the present invention may be in a variety of forms. These forms include, for example, liquid, semi-solid and solid dosage forms, such as liquid solutions (e.g., injectable solutions and infusible solutions), pulvis or suspensions, liposomes, and suppositories. The preferred form depends on the intended mode of administration and therapeutic use.

The pharmaceutical preparation, preferably in the form of a lyophilized preparation or an aqueous solution, comprising the antibody described herein can be prepared by mixing the antibody of desired purity of the present invention with one or more optional pharmaceutical supplementary materials.

The pharmaceutical composition or preparation of the present invention may also comprise more than one active ingredient required by a particular indication treated, preferably those having complementarity activity without adversely affecting one another. For example, it may be desirable to also provide additional therapeutic agents, such as a chemotherapeutic agent, a cytokine, a cytotoxic agent, a vaccine, an additional antibody, a small molecule drug, or an immunomodulatory agent. The active ingredients are suitably combined in an amount effective for an intended purpose.

A sustained release preparation can be prepared. Suitable examples of the sustained release preparation include a semipermeable matrix of a solid hydrophobic polymer containing an antibody. The matrix is in the form of a shaped article, such as a film or a microcapsule.

VIII. Pharmaceutical Combination and Kit

In some embodiments, the present invention also provides a pharmaceutical combination or a pharmaceutical combination product comprising the anti-CLDN18.2 antibody or the fragment (preferably the antigen-binding fragment) thereof, or the immunoconjugate thereof of the present invention, and one or more additional therapeutic agents (e.g., a chemotherapeutic agent, a cytokine, a cytotoxic agent, an additional antibody, a small molecule drug, or an immunomodulatory agent).

Another object of the present invention is to provide a kit of parts comprising the pharmaceutical combination of the present invention; preferably, the kit is in the form of a pharmaceutical dose unit. Dose units may thus be provided according to the dosing regimen or the interval between drug administrations.

In one embodiment, the kit of parts of the present invention comprises in the same package:

a first container containing a pharmaceutical composition comprising the anti-CLDN18.2 antibody or the fragment thereof;

a second container containing a pharmaceutical composition comprising other therapeutic agents.

IX. Use and Method

One aspect of the present invention provides a method for preventing or treating a tumor (e.g., cancer) in a subject, which comprises administering to the subject an effective amount of the anti-CLDN18.2 antibody or the fragment (preferably the antigen-binding fragment) thereof, the immunoconjugate, the pharmaceutical composition, the pharmaceutical combination or the kit of the present invention.

In some embodiments, the tumor (e.g., cancer) patient has CLDN18.2 (e.g., at an elevated level, e.g., at a nucleic acid or protein level).

In some embodiments, the tumor, e.g., cancer, includes solid tumors and hematological tumors as well as metastatic lesions. In one embodiment, examples of the solid tumors include malignant tumors. The cancer may be at an early, intermediate or advanced stage, or may be a metastatic cancer.

In some embodiments, the tumor treatment will benefit from inhibition of CLDN18.2 at a nucleic acid or protein level. In some embodiments, the tumor treatment benefits from ADCC or CDC effect induced by the antibody of the present invention.

In a specific embodiment, the anti-CLDN18.2 antibody of the present invention is capable of inhibiting proliferation of tumor cells, e.g., tumor cells expressing CLDN18.2, such as gastric cancer cells or pancreatic cancer cells.

In a specific embodiment, the anti-CLDN18.2 antibody of the present invention has strong ADCC or CDC activity.

In some embodiments, the tumor is a tumor immune escape.

In some embodiments, the tumor is cancer, e.g., gastric cancer or pancreatic cancer.

The subject may be a mammal, e.g., a primate, preferably a higher primate, e.g., a human (e.g., an individual suffering from or at risk of suffering from the disease described herein). In one embodiment, the subject suffers from or is at risk of suffering from the disease described herein (e.g., cancer). In certain embodiments, the subject is receiving or has received additional therapies, e.g., chemotherapy and/or radiotherapy. In some embodiments, the subject has previously received or is receiving immunotherapy.

In other aspects, the present invention provides use of the antibody molecule or the fragment thereof, the immunoconjugate thereof, the pharmaceutical composition, the pharmaceutical combination or the kit in producing or preparing a drug for the use described herein, e.g., for use in preventing or treating a related disease or disorder mentioned herein.

In some embodiments, the antibody molecule or the fragment thereof, the immunoconjugate thereof, the pharmaceutical composition, the pharmaceutical combination or the kit of the present invention delays the onset of the disorder and/or symptoms associated with the disorder.

In some embodiments, the antibody molecule or the fragment thereof, the immunoconjugate thereof, or the pharmaceutical composition of the present invention can also be administered in combination with one or more other therapies, e.g., therapeutic modalities and/or other therapeutic agents, for the use described herein, e.g., for use in preventing or treating a related disease or disorder mentioned herein.

In some embodiments, the treatment modality includes surgery, radiotherapy, partial irradiation, focused irradiation, or the like.

In some embodiments, the therapeutic agent is selected from a chemotherapeutic agent, a cytokine, a cytotoxic agent, a vaccine, an additional antibody, a small molecule drug or an immunomodulatory agent.

Exemplary immunomodulatory agents include immunosuppressants or anti-inflammatory agents.

In some embodiments, the antibody combination described herein can be administered separately, e.g., as a separate antibody.

Such combination therapies encompass both co-administration (e.g., two or more therapeutic agents are contained in the same preparation or separate preparations), and separate administrations, in which the antibody of the present invention can be administered prior to, concurrently with, and/or after the administration of other therapeutic agents and/or pharmaceuticals.

The route of administration of the pharmaceutical composition is based on a known method, for example, oral, intravenous, intraperitoneal, intracerebral (intraparenchymal), intraventricular, intramuscular, intraocular, intraarterial, intraportal or intralesional route; via sustained release systems or via implanted devices. In certain embodiments, the composition can be administered by bolus injection or by continuous infusion or by an implanted device.

The composition can also be administered topically via an implanted membrane, sponge, or another suitable material that absorbs or encapsulates the desired molecule. In certain embodiments, when an implanted device is used, the device can be implanted into any suitable tissue or organ, and the desired molecule can be delivered via diffusion, time-released bolus, or continuous administration.

X. Methods and Compositions for Diagnosis and Detection

In certain embodiments, any of the anti-CLDN18.2 antibodies or fragments (preferably antigen-binding fragments) thereof provided herein may be used to detect the presence of CLDN18.2 in a biological sample. The term "detection" or "detect" used herein includes quantitative and qualitative detections, and exemplary detections may involve immunohistochemistry, immunocytochemistry, flow cytometry (e.g., FACS), magnetic beads complexed with antibody molecules, ELISA, and PCR (e.g., RT-PCR). In certain embodiments, the biological sample is blood, serum, or other liquid samples of biological origin. In certain embodiments, the biological sample includes cells or tissues. In some embodiments, the biological sample is derived from a hyperproliferative or cancerous lesion.

In one embodiment, provided is an anti-CLDN18.2 antibody or a fragment thereof for use in a diagnostic or detection method. In another aspect, provided is a method for detecting the presence of CLDN18.2 in a biological sample. In certain embodiments, the method comprises detecting the presence of the CLDN18.2 protein in a biological sample. In certain embodiments, the CLDN18.2 is a human CLDN18.2. In certain embodiments, the method comprises contacting a biological sample with the anti-CLDN18.2 antibody or the fragment thereof described herein under conditions allowing binding of the anti-CLDN18.2 antibody or the fragment thereof to CLDN18.2, and detecting whether a complex is formed by the anti-CLDN18.2 antibody or the fragment thereof and CLDN18.2. The formation of the complex indicates the presence of CLDN18.2. The method may be an in vitro or in vivo method. In one embodiment, the anti-CLDN18.2 antibody or the fragment thereof is used to select a subject eligible for treatment with the anti-CLDN18.2 antibody or the fragment thereof, e.g., wherein CLDN18.2 is a biomarker for selecting the subject.

In one embodiment, the antibody of the present invention can be used to diagnose a tumor, e.g., cancer, e.g., to assess (e.g., monitor) the treatment or progression, diagnosis and/or stage of the disease described herein in an individual. In certain embodiments, provided is a labeled anti-CLDN18.2 antibody or fragment thereof. The label includes, but is not limited to, a label or moiety that is detected directly, e.g., a fluorescent label, a chromophoric label, an electron-dense label, a chemiluminescent label, and a radioactive label, and a moiety that is detected indirectly, such as an enzyme or a ligand, for example, by enzymatic reaction or molecular interaction.

In some embodiments provided herein, the sample is obtained prior to treatment with the anti-CLDN18.2 antibody or the fragment thereof. In some embodiments, the sample is obtained prior to application of other therapies. In some embodiments, the sample is obtained during treatment with other therapies, or after treatment with other therapies.

In some embodiments, the sample is a formalin-fixed, paraffin-embedded (FFPE) sample. In some embodiments, the sample is a biopsy (e.g., a core biopsy) specimen, a surgical specimen (e.g., a specimen from a surgical resection), or a fine-needle aspirate.

In some embodiments, CLDN18.2 is detected prior to treatment, e.g., prior to initial treatment or prior to a treatment after an interval from a certain treatment.

In some embodiments, provided is a method for treating the disease of the present invention, and the method comprises: detecting the presence of CLDN18.2 in a subject (e.g., a sample) (e.g., a sample of the subject), thereby determining a CLDN18.2 value; comparing the CLDN18.2 value to a control value; and if the CLDN18.2 value is greater than the control value, administering to the subject a therapeutically effective amount of the anti-CLDN18.2 antibody or the fragment thereof (e.g., the anti-CLDN18.2 antibody or the fragment thereof described herein), optionally, in combination with one or more other therapies, thereby treating the disease.

These and other aspects and embodiments of the present invention are illustrated in the drawings (brief description of the drawings follows) and in the following detailed description of the present invention and are described in the following examples. Any or all of the features described above and throughout the present invention may be combined in various embodiments of the present invention. The following examples further illustrate the present invention. However, it should be understood that the examples are described by way of illustration rather than limitation, and various modifications may be made by those skilled in the art.

EXAMPLES

TABLE A

SEQ ID NO numbering for sequences of exemplary antibodies of the present invention and positive control antibody (HCDR1 defined by the AbM rules, and HCDR2, HCDR3, LCDR1, LCDR2 and LCDR3 defined by the Kabat rules)

| | Antibodies | | | | | | | | |
|---|---|---|---|---|---|---|---|---|---|
| | HB37A6 (fully human antibody) | 69H9 | Hz69H9 | 38F8 | Hz38F8 | 59C1 | Hz59C1 | 51H10 | Hz51H10 |
| HCDR1 | 1 | 12 | 12 | 23 | 23 | 33 | 33 | 42 | 42 |
| HCDR2 | 2 | 13 | 20 | 24 | 24 | 34 | 34 | 43 | 43 |
| HCDR3 | 3 | 14 | 14 | 25 | 25 | 35 | 35 | 44 | 44 |
| VH | 4 | 15 | 21 | 26 | 27 | 36 | 37 | 45 | 48 |
| HC | 5 | 5 | 5 | 5 | 5 | 5 | 5 | 5 | 5 |
| LCDR1 | 6 | 16 | 16 | 28 | 28 | 38 | 38 | 38 | 38 |
| LCDR2 | 7 | 17 | 17 | 29 | 29 | 17 | 17 | 17 | 17 |
| LCDR3 | 8 | 18 | 18 | 30 | 30 | 39 | 39 | 46 | 46 |
| VL | 9 | 19 | 22 | 31 | 32 | 40 | 41 | 47 | 49 |
| LC | 10 | 10 | 10 | 10 | 10 | 10 | 10 | 10 | 10 |

| | Antibodies | | | | | | | | |
|---|---|---|---|---|---|---|---|---|---|
| | 46F6 | Hz46F6 | 25C7 | Hz25C7 | 3G3 | Hz3G3 | 14A5 | Hz14A5 | Positive control antibody Zmab |
| HCDR1 | 50 | 50 | 58 | 58 | 69 | 69 | 77 | 77 | 87 |
| HCDR2 | 51 | 51 | 59 | 59 | 70 | 70 | 78 | 84 | 88 |
| HCDR3 | 52 | 52 | 60 | 60 | 71 | 71 | 79 | 79 | 89 |
| VH | 53 | 56 | 61 | 66 | 72 | 73 | 80 | 85 | 90 |
| HC | 5 | 5 | 5 | 5 | 5 | 5 | 5 | 5 | 5 |
| LCDR1 | 28 | 28 | 62 | 67 | 38 | 38 | 28 | 28 | 38 |
| LCDR2 | 17 | 17 | 63 | 63 | 17 | 17 | 81 | 81 | 17 |
| LCDR3 | 54 | 54 | 64 | 64 | 74 | 74 | 82 | 82 | 91 |
| VL | 55 | 57 | 65 | 68 | 75 | 76 | 83 | 86 | 92 |
| LC | 10 | 10 | 10 | 10 | 10 | 10 | 10 | 10 | 10 |

Example 1. Construction of Stably Expressing Cell Lines

Preparation of Cell Lines Overexpressing Human CLDN18.2

According to the manufacturer's instructions, the Freedom® CHO-S® kit (Invitrogen, A1369601) was used to construct cell lines stably expressing human Claudin18.2 (abbreviated as CLDN18.2, the same applies hereinafter). Firstly, the human CLDN18.2 (UniProt ID: P56856-2) full-length gene was constructed into a vector pCHO1.0, the constructed plasmids were transfected into CHO-S cells (Invitrogen, A1369601) and HEK293 cells (Invitrogen, A14527) by chemical transfection and electrotransfection, and the transfected cells were subjected to two rounds of pressurized screening to obtain cell pools expressing CLDN18.2. Then, the cells highly expressing CLDN18.2 were sorted out by using a flow cytometric sorter (MoFlo XDP, Beckman Coulter), and the monoclonal cell lines CHO-hCLDN18.2 and HEK293-hCLDN18.2 that stably express CLDN18.2 were obtained by dilution.

Preparation of Cell Line Overexpressing Human CLDN18.1

According to the manufacturer's instructions, the Freedom® CHO-S® kit (Invitrogen, A1369601) was used to construct cell lines stably expressing human Claudin18.1 (abbreviated as CLDN18.1, the same applies hereinafter). Firstly, the human CLDN18.1 (UniProt ID: P56856-1) full-length gene was constructed into a vector pCHO1.0 (Invitrogen, A1369601), the constructed plasmids were transfected into CHO-S cells (Invitrogen, A1369601) by chemical transfection, and the transfected cells were subjected to two rounds of pressurized screening to obtain cell pools expressing CLDN18.1. Then, the cells highly expressing CLDN18.1 were sorted out by using a flow cytometric sorter (MoFlo XDP, Beckman Coulter), and the monoclonal cell line CHO-hCLDN18.1 stably expressing CLDN18.1 was obtained by dilution.

Construction of Tumor Cell Lines Overexpressing CLDN18.2

The human CLDN18.2 (UniProt ID: P56856-2) full-length gene was constructed into a vector pWPT-GFP (Addgene, 12255) to replace the GFP sequence therein, and the construct was transfected, together with the packaging vectors psPAX2 (Addgene, 12260) and pMD2.G (Addgene, 12259) of the lentivirus, into HEK293T (ATCC, CRL-3216) cells for virus packaging. The culture supernatants cultured for 48 h and 72 h were each collected, and the lentivirus was concentrated using PEG8000. The pancreatic cancer DAN-G cells and gastric cancer KATO III cells were transfected with the concentrated virus, and then the cells expressing CLDN18.2 were sorted out by using a flow cytometric sorter (MoFlo XDP, Beckman Coulter) to obtain the tumor cell lines DAN-G-CLDN18.2 and KATO III-CLDN18.2 stably transfected with CLDN18.2.

Example 2. Screening of Hybridomas for Anti-hCLDN18.2 Monoclonal Antibodies

The hybridoma technology was adopted in the present invention. Mice were immunized using the cells (CHO-huClaudin18.2) obtained in Example 1 (the method and the process are shown in Table 1), and then the obtained spleen cells of the mice were fused with myeloma cells, thus obtaining the hybridoma cells capable of secreting the CLDN18.2 antibodies.

Immunization of Mice

TABLE 1

| Experimental animals and immunization information | |
|---|---|
| Mice | Bal b/c mice (purchased from Beijing Vital River Laboratory Animal Technology Co., Ltd.); H2L2 fully human antibody transgenic mice (purchased from Harbour BioMed) |
| Immunizing antigen | CHO-hCLDN18.2 |
| Immunizing method | $1 \times 10^7$ cells/mouse, intraperitoneal injection |
| Times of immunizing | 4 |
| Final booster immunization | $1 \times 10^7$ cells/mouse, intraperitoneal injection, 3 days before fusion |

Fusion of Hybridomas

The mice were sacrificed, the abdominal cavity was opened aseptically to take out the spleen, and the connective tissue attached around the spleen was removed. The spleen cells were fully released by squeezing using a needle to prepare the spleen cell suspension. The cell suspension was filtered through a 70 μM cell screen, washed once with RPMI-1640 medium, and centrifuged at 1200 rpm for 6 min. The supernatant was removed, the cells were resuspended with RBC lysis buffer (GIBCO), and then the RBCs were lysed. The suspension was centrifuged to remove the supernatant, and the cells were resuspended in RPMI-1640 medium and counted. The SP2/0 cells and spleen cells with RBCs lysed were mixed in a ratio of 1:2 to 1:1, and centrifuged at 1000 rpm for 6 min. After the supernatant was removed, the mixed cells were resuspended in fusion buffer. Then 15 mL of fusion buffer was added, and the mixture was centrifuged at 1000 rpm for 5 min to remove the supernatant. The above steps were repeated once. The cells were resuspended in an appropriate volume of fusion buffer and the density of mixed cells was adjusted to $1\times10^7$ cells/mL. After fusion by the electrofusion apparatus, the cells were left to stand in the electrofusion dish at room temperature for 5 min. The cells were transferred into a centrifuge tube and diluted to 1-$2\times10^4$ cells/mL. 100 μL of cell suspension was added to each well of a 96-well plate. The medium was changed on day 5 after fusion. After 10 days (or longer, depending on the cell growth state) of culture, the supernatant was collected and determined by a flow cytometer (FACS), and the positive clones were screened out.

High-Throughput Screening of Hybridoma Cells

Hybridoma cells specifically expressing the anti-CLDN18.2 antibody were screened out by a flow cytometer (FACS), and the secreted antibody did not bind to CLDN18.1.

The cells to be tested (HEK293-hCLDN18.2) obtained in Example 1 were counted, diluted to $1\times10^6$ cells/mL, and then added to a U-bottom 96-well plate at 100 μL/well. The cells were centrifuged at 500 g for 5 min to remove the cell medium. The hybridoma culture supernatant in the 96-well plate was added to the U-shaped plate at 100 μL/well, and the cells were resuspended, and the suspension was left to stand on ice for 30 min. The suspension was centrifuged at 500 g for 5 min to remove the supernatant, and the cells were washed once with PBS. 100 μL of FITC-labeled anti-mouse Fab secondary antibody (1:500 dilution in PBS) was added to each well, and 100 μL of FITC-labeled anti-human Fab secondary antibody was added to the positive control antibody. The mixture was incubated for 30 min on ice in the dark. The mixture was centrifuged at 500 g for 5 min to remove the supernatant, and the cells were washed once with PBS. The cells were resuspended with 50 μL of 1×PBS and determined by FACS.

The positive clones were rescreened for CHO-hCLDN18.1 in the same manner as described above to obtain 9 strains of hybridoma cells that bind to human CLDN18.2 but do not bind to human CLDN18.1. 8 strains of the hybridoma cells were derived from Bal b/c mice, and 1 strain of the hybridoma cells was derived from H2L2 fully human transgenic mice. See Table 2 for details.

TABLE 2

Candidate antibody clones obtained by high-throughput screening of hybridomas

| Mice | Name of clone |
|---|---|
| Bal b/c mice | 3G3, 14A5, 25C7, 38F8, 69H9, 46F6, 59C1, 51H10 |
| H2L2 fully human transgenic mice | HB37A6 |

Example 3. Acquisition of Antibody Genes

Antibody light and heavy chain gene sequences of the 9 strains of hybridoma cells obtained in Example 2 (3G3, 14A5, 25C7, 38F8, 69H9, 46F6, 59C1, 51H10 and HB37A6) were extracted by using molecular biology techniques. The total RNA of each of the 9 hybridoma cells was extracted by an RNA extraction kit (Biomiga, R6311-02), and then reversely transcribed with the PrimeScript II 1st Strand cDNA Synthesis Kit (Takara, 6110A) to obtain cDNA. The heavy and light chain variable region sequences of the antibody were each amplified with a degenerate primer and inserted into a pMD20-T vector (Takara, 6028), and the clones were picked out and sequenced after ligation and transformation.

See Table A for antibody sequences.

Example 4. Preparation of Recombinant CLDN18.2 Antibodies

The 9 antibodies (3G3, 14A5, 25C7, 38F8, 69H9, 46F6, 59C1, 51H10 and HB37A6) screened out in Example 2 and the control antibody zolbetuximab (abbreviated as Zmab, sequence derived from INN117) were expressed in HEK293 cells (Invitrogen, A14527) as full-length monoclonal antibodies. The expression vector was constructed firstly. Each of the 9 paired heavy chain variable regions and light chain variable regions were placed at N-termini of the heavy chain constant region (SEQ ID NO: 5) and the light chain kappa constant region (SEQ ID NO: 10) of human IgG1, respectively, and constructed into a pcDNA3.1 expression vector with N-terminus signal peptide to obtain the light and heavy chain expression vectors. The obtained light and heavy chain expression vectors were each co-transfected with PEI (Polysciences Inc, 23966) to transiently transfect HEK293 cells, and the medium supernatant was collected after 7 days of culturing. The supernatant was purified by a Protein A column (Hitrap Mabselect Sure, GE 11-0034-95), followed by ultrafiltration and buffer-exchange into PBS (Gibco, 70011-044). The concentration was determined by the A280 method and the purity was determined by the SEC-HPLC method, thus obtaining an antibody solution with a purity of greater than 95%.

Example 5. Determination of Affinity of Recombinant CLDN18.2 Antibodies for Antigen by BLI The equilibrium dissociation constant ($K_D$) for binding of the antibodies of the present invention to human CLDN18.2 was determined by bio-layer interferometry (BLI). A BLI affinity assay was conducted according to the existing method (Estep, P et al., High throughput solution based measurement of antibody-antigen affinity and epitope binding. MAbs, 2013.5(2): p. 270-8). The AHC (18-5060, Fortebio) sensor was soaked in SD buffer (1×PBS, BSA 0.1%, Tween-20 0.05%). 100 μL of SD buffer, each antibody and human Claudin18.2 protein (P50251802, GenScript) were added to a 96-well black polystyrene half-area microplate (Greiner, 675076), respectively. The detection was performed using Fortebio Octet Red96, and the $K_D$ values were analyzed using Fortebio Octet analysis software. The affinity data of the antibodies are shown in Table 3: all 9 antibodies have high affinity, wherein except that 3G3 was comparable in affinity to the control antibody Zmab, all others are superior to the control antibody Zmab.

TABLE 3

Affinity constants of CLDN18.2 antibodies

| Clone ID | $K_D$ (M) |
|---|---|
| 3G3 | 2.80E−09 |
| 14A5 | 5.29E−10 |
| 25C7 | 1.46E−09 |
| 38F8 | 1.03E−09 |
| 69H9 | 9.46E−10 |
| 46F6 | 7.32E−10 |
| 59C1 | 1.01E−09 |
| 51H10 | 1.90E−09 |
| HB37A6 | 3.26E−10 |
| Zmab | 2.14E−09 |

Example 6. Binding Specificity of CLDN18.2 Antibodies to CLDN18 Cells

Figure 2:
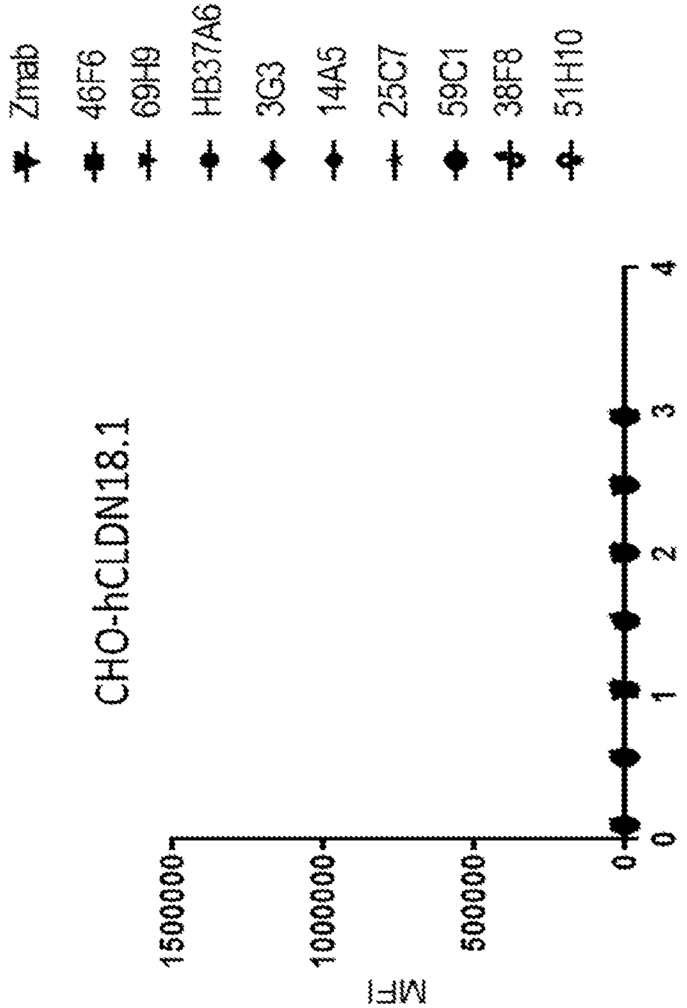
FIG. 2 shows that anti-CLDN18.2 antibodies do not bind to CLDN18.1 on cell surface.

The binding of each of the above 9 antibodies to the CHO-S cell lines stably transfected with human CLDN18.2 and human CLDN18.1 (i.e., CHO-hCLDN18.2 and CHO-hCLDN18.1 prepared as described in the Examples) obtained in Example 1 was determined by flow cytometry (FACS). Reference was made to Example 2 for the experimental methods. The experimental data were analyzed using GraphPad Prism software, and FIGS. 1 and 2 were obtained. As shown in FIGS. 1 and 2, all of the 9 antibodies specifically bind to human CLDN18.2 but do not bind to human CLDN18.1.

Example 7. Reporter Gene-Based ADCC Activity Assay for CLDN18.2 Antibodies

Figure 3:
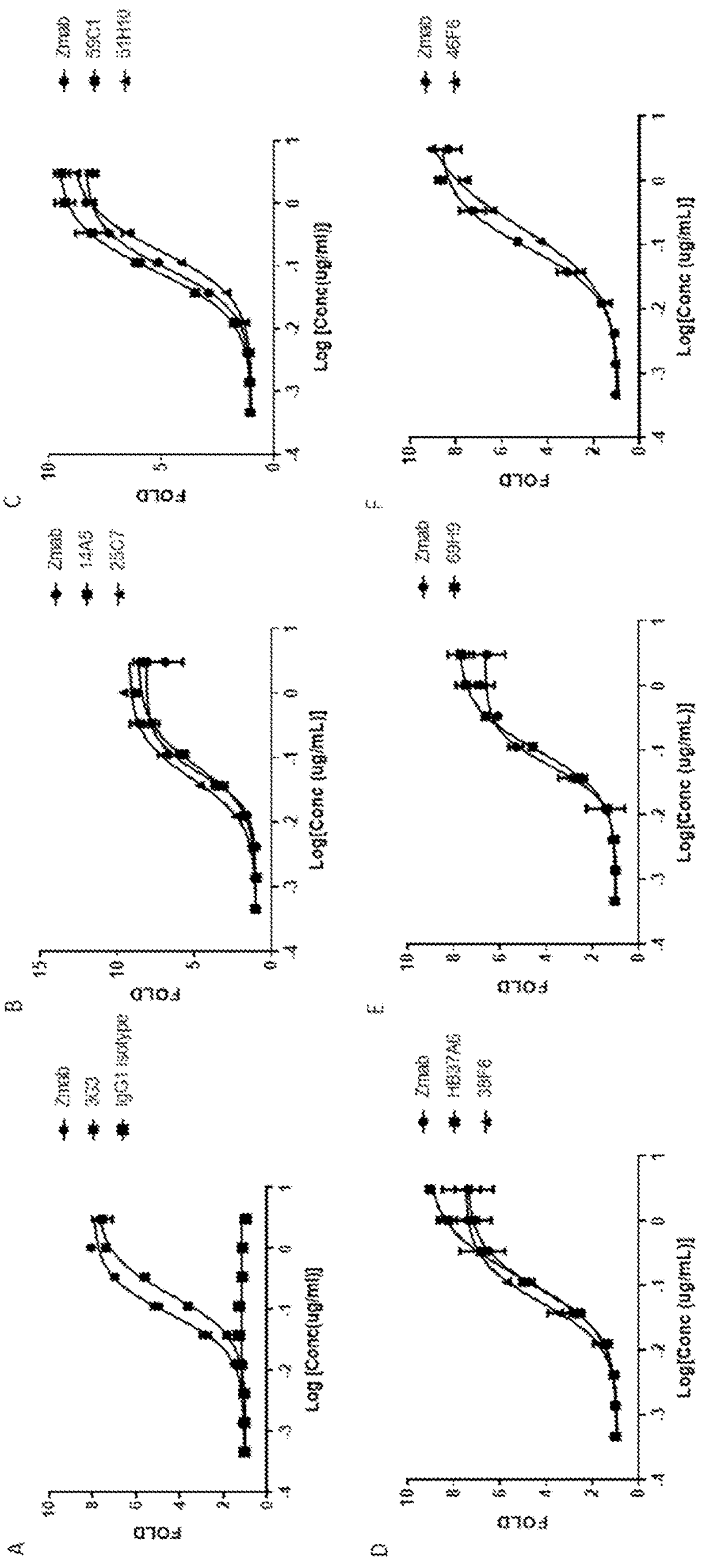
FIG. 3 shows the reporter gene-based ADCC activity of anti-CLDN18.2 antibodies for CHO-hCLDN18.2.

The ADCC activity of the above 9 antibodies was determined using ADCC effector cells (Promega, G7102) containing luciferase reporter gene. The target cells CHO-hCLDN18.2 and ADCC effector cells in logarithmic growth phase were counted separately and added to a 96-well white bottom plate at a ratio of 1:6 in a total volume of 50 μL, a total of $1.75\times10^5$ cells per well. Then, each of the above antibodies was added to each well, and the cells were incubated at 37 °C, 5% $CO_2$ for 8-10 h. The respective concentrations of the antibodies were as follows: the starting point was 3 nM, and then 3-fold dilution was performed to obtain a total of 9 concentration points; that is, the concentrations used for each antibody were: 3 nM, 1 nM, 0.333 nM, 0.111 nM, 0.037 nM, 0.123 nM, 0.0041 nM, 0.0014 nM and 0.00046 nM. According to the manufacturer's instructions, the fluorescence detection was performed using the Bio- Glo™ Luciferase reagent (Promega, G7940). As shown in the results of FIG. 3, all of the 9 antibodies have ADCC activity comparable to that of the control antibody Zmab.

Example 8. Humanization of Murine Antibodies 8 murine antibodies (3G3, 14A5, 25C7, 38F8, 69H9, 46F6, 59C1 and 51H10) in Example 3 were selected for humanization. The CDR regions of the antibody were determined, with Abm naming rules for the heavy chain CDR1 and Kabat naming rules for the remaining CDRs. Through sequence alignment for similarity, a human germline gene sequence that had the highest similarity as compared to the murine antibody variable region sequence was selected as a framework region template of the humanized antibody, and then the CDR regions were transplanted into the templates. The three-dimensional structure of each antibody was constructed by using Discovery Studio software, and the amino acids in the framework region affecting the CDR regions were back-mutated to obtain a humanized antibody sequence. The sequences of humanized antibodies Hz3G3, Hz14A5, Hz25C7, Hz38F8, Hz69H9, Hz46F6, Hz59C1 and Hz51H10 are shown in Table A.

These humanized recombinant antibodies were prepared and purified according to the method described in Example 4 to obtain antibody solutions in PBS with a purity of greater than 95%.

Example 9. Determination of Affinity of CLDN18.2 Antibodies by SPR

The equilibrium dissociation constant ($K_D$) for binding of the 8 humanized antibodies (Hz3G3, Hz14A5, Hz25C7, Hz38F8, Hz69H9, Hz46F6, Hz59C1 and Hz51H10) and 1 fully human antibody (HB37A6) to human CLDN18.2 was determined by surface plasmon resonance (SPR). According to the manufacturer's instructions, human Claudin18.2 (GenScrip, P50251802) was coupled to the surface of a CM5 chip (GE Healthcare, 29-1496-03) using the amino coupling kit (GE Healthcare, BR-1006-33), and the remaining activation sites were blocked by injection of 1 M ethanolamine after coupling. According to the manufacturer's instructions, the binding and dissociation between the antigen on the chip surface and antibodies in the mobile phase were determined by Biacore (GE Healthcare, T200) to obtain affinity and kinetic constants. The antibodies (0-100 nM) after gradient dilution flowed over the chip surface in an order from low to high concentrations, with the binding time of 180 s and the dissociation time of 600 s. Finally, the chip was regenerated using 10 mM Glycine pH 1.5 (GE Healthcare, BR-1003-54). Kinetic analysis of the data results were performed using Biacore T200 analysis software with a 1:1 binding model. As shown in Table 4, except for Hz25C7 and Hz3G3, the other antibodies were all superior to the control antibody Zmab in terms of affinity.

TABLE 4

Determination of affinity constant (equilibrium dissociation constant) of CLDN18.2 antibodies by SPR

| Antibodies | ka (1/Ms) | kd (1/s) | KD (M) |
|---|---|---|---|
| Zmab | 3.482E+5 | 7.894E−4 | 2.267E−9 |
| Hz69H9 | 3.869E+5 | 1.155E−4 | 2.986E−10 |
| Hz38F8 | 3.180E+5 | 9.969E−5 | 3.135E−10 |
| Hz14A5 | 4.245E+5 | 2.081E−4 | 4.901E−10 |
| HB37A6 | 4.252E+5 | 3.063E−4 | 7.203E−10 |
| Hz59C1 | 2.482E+5 | 4.330E−4 | 1.745E−9 |
| Hz51H10 | 3.246E+5 | 6.309E−4 | 1.944E−9 |
| Hz46F6 | 1.466E+5 | 1.504E−4 | 1.026E−9 |
| Hz25C7 | 1.158E+5 | 0.001139 | 9.836E−9 |
| Hz3G3 | 5.646E+4 | 7.988E−4 | 1.415E−8 |

Example 10. Reporter Gene-Based ADCC Activity Assay for Humanized Antibodies

Figure 4:
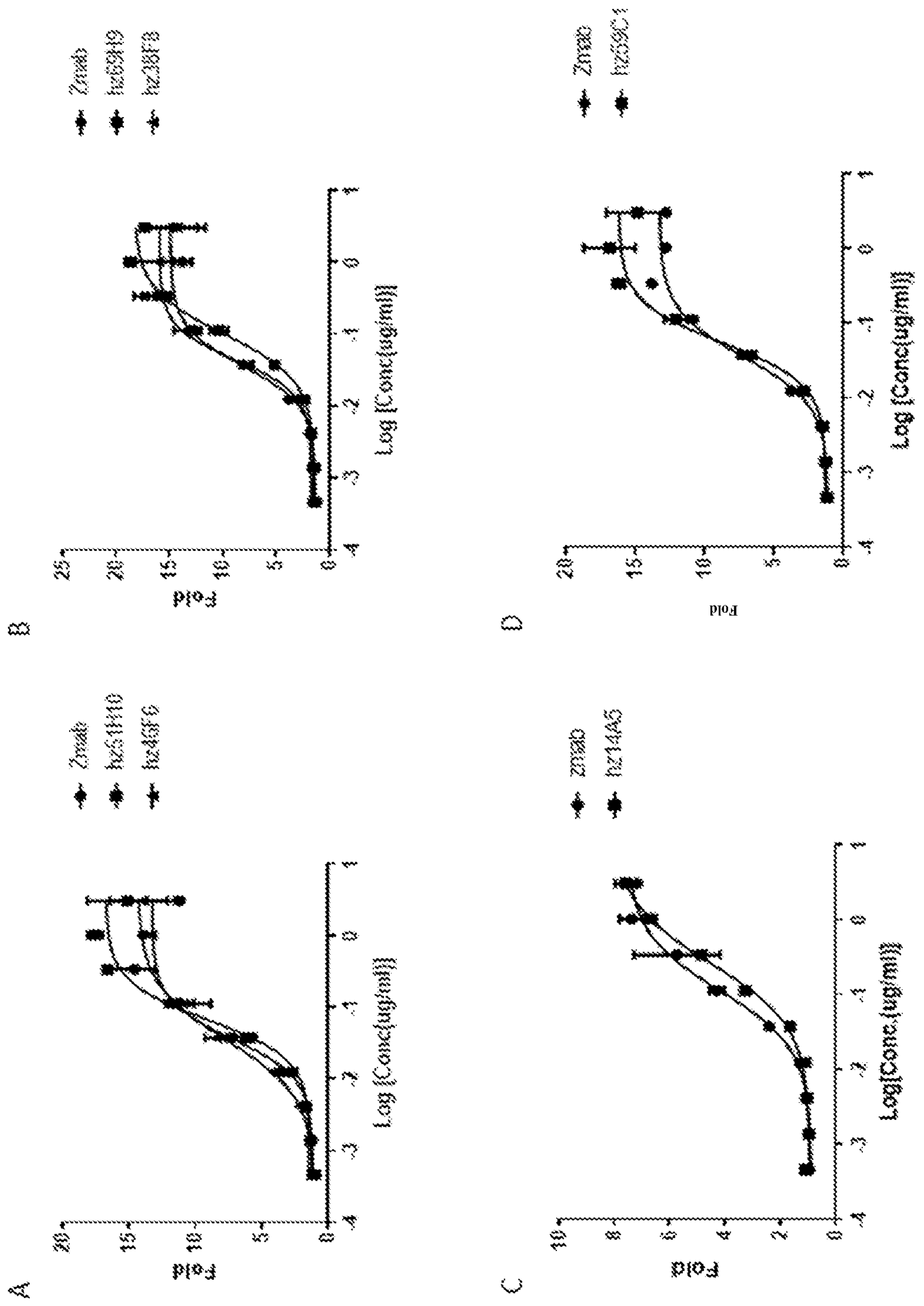
FIG. 4 shows the reporter gene-based ADCC activity of humanized anti-CLDN18.2 antibodies for CHO-hCLDN18.2.

Based on SPR affinity data, Hz14A5, Hz38F8, Hz69H9, Hz46F6, Hz59C1 and Hz51H10 were selected for reporter gene-based ADCC activity assay. Reference was made to Example 7 for the experimental process. As shown in FIG. 4, the humanized antibodies Hz14A5, Hz38F8, Hz69H9, Hz46F6, Hz59C1 and Hz51H10 all show ADCC activity comparable to that of the control antibody.

Example 11. Binding of CLDN18.2 Antibodies to Tumor Cell Lines

Figure 5:
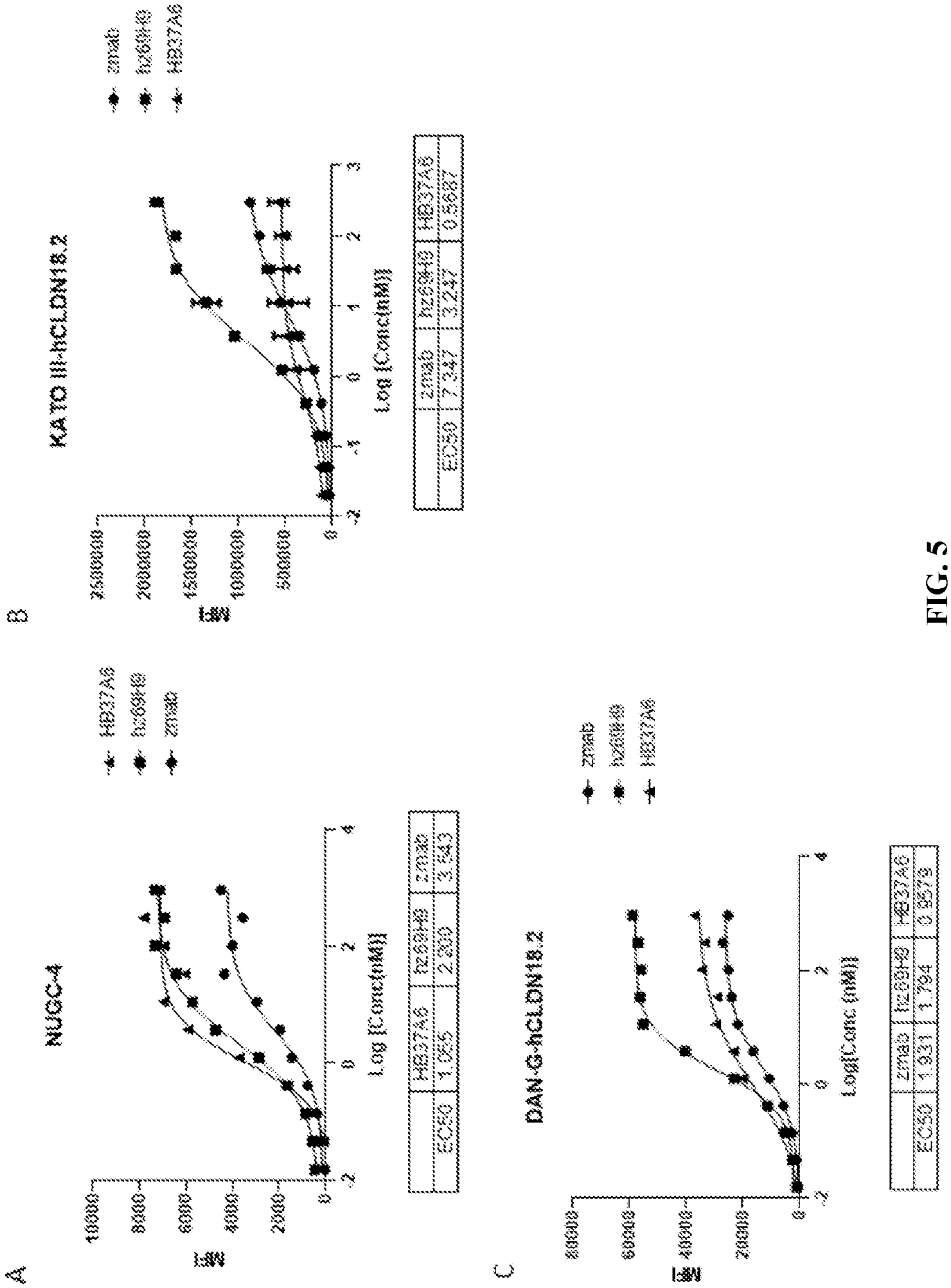
FIG. 5 shows the binding of anti-CLDN18.2 antibodies to the gastric cancer cell line NUGC-4, the gastric cancer cell line KATO III-hCLDN18.2 and the pancreatic cancer cell line DAN-G-hCLDN18.2.

Based on the above results, 1 humanized antibody Hz69H9 and 1 fully human antibody HB37A6 were selected for further determination. Referring to Example 4, the binding of the two antibodies to each of the gastric cancer cell line NUGC-4, the gastric cancer cell line KATO III-hCLDN18.2 and the pancreatic cancer cell line DAN-G-hCLDN18.2 was determined by FACS. FIG. 5 shows that humanized antibody Hz69H9 and fully human antibody HB37A6 both have relatively good tumor cell specific binding, which is better than that of the control antibody Zmab.

Example 12. CDC Activity Assay for CLDN18.2 Antibodies

Figure 6:
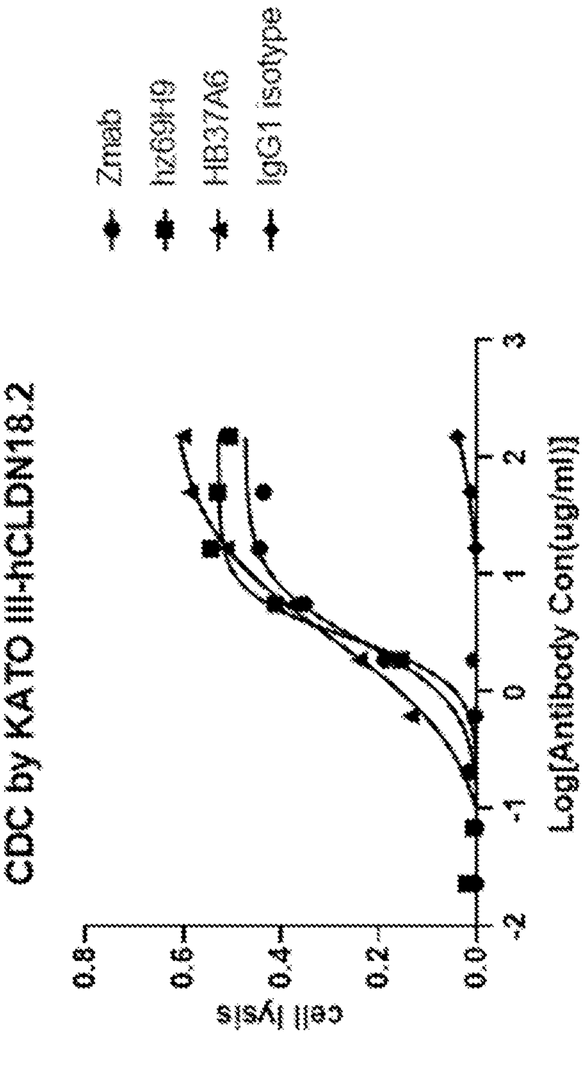
FIG. 6 shows the CDC activity assay for anti-CLDN18.2 antibodies.

The CDC activity of the antibody molecules was determined using the KATO III-CLDN18.2 cell line. $1\times10^5$ target cells KATO III-hCLDN18.2 were added to a 96-well plate, and then the antibody molecule at an appropriate concentration was added. The reaction system was incubated at 37 °C for 30 min, and then the freshly prepared human serum complement (Sigma, S1764) was added. The concentrations of the antibody were as follows: serial dilution concentrations, with an initial concentration of 150 μg/mL, a total of 9 concentration points after 3-fold dilution. The reaction system was incubated again in an incubator at 37 °C for 3 h, and then the data were read by a microplate reader (ThermoFisher, MULTISKAN FC) using the CCK-8 kit (Dojindo, CK04). The results are shown in FIG. 6, where Hz69H9 and HB37A6 have CDC activity comparable to that of the control antibody Zmab.

Example 13. ADCC Activity Assay for CLDN18.2 Antibodies

The human peripheral blood mononuclear cells (PBMCs, Allcells or Saily) were resuspended in complete medium RPMI-1640 (Hyclone, SH30809.01)+10% fetal bovine serum (FBS, Hyclone, SH30084.03), and the PBMCs were adjusted to $1\times10^7$ cells/mL. The NUGC-4 cells or the DAN-G tumor target cells DAN-G-CLDN18.2 overexpressing Claudin18.2 were labeled with Far-Red (Invitrogen) for 10 min, washed twice, and then resuspended in complete medium RPMI-1640 (Hyclone, SH30809.01)+10% fetal bovine serum (FBS, Hyclone, SH30084.03). The cell concentration was adjusted to $2\times10^5$ cells/mL. The PBMCs were mixed with each of anti-claudin18.2 monoclonal antibodies Hz69H9 and HB37A6 and the control antibody Zmab (an initial concentration of 30 nM for each antibody, 3-fold serial dilution, a total of 12 concentration points). The mixture was incubated at 37 °C for 30 min, and then 50 μL of tumor target cells ($1\times10^4$) were added to 50 μL of PBMC effector cells at a effector-to-target ratio of 50:1. The mixture was incubated at 37 °C for 8 h and centrifuged, the cells were resuspended in propidium iodide (PI, Invitrogen) at a final concentration of 10 μg/mL, and the Far-Red and PI double positive cells were detected by a flow cytometer (BD, FACSCELESTA). The killing ratio for tumor target cells was calculated by FACSDiva software (BD, Celestsa).

Figure 7:
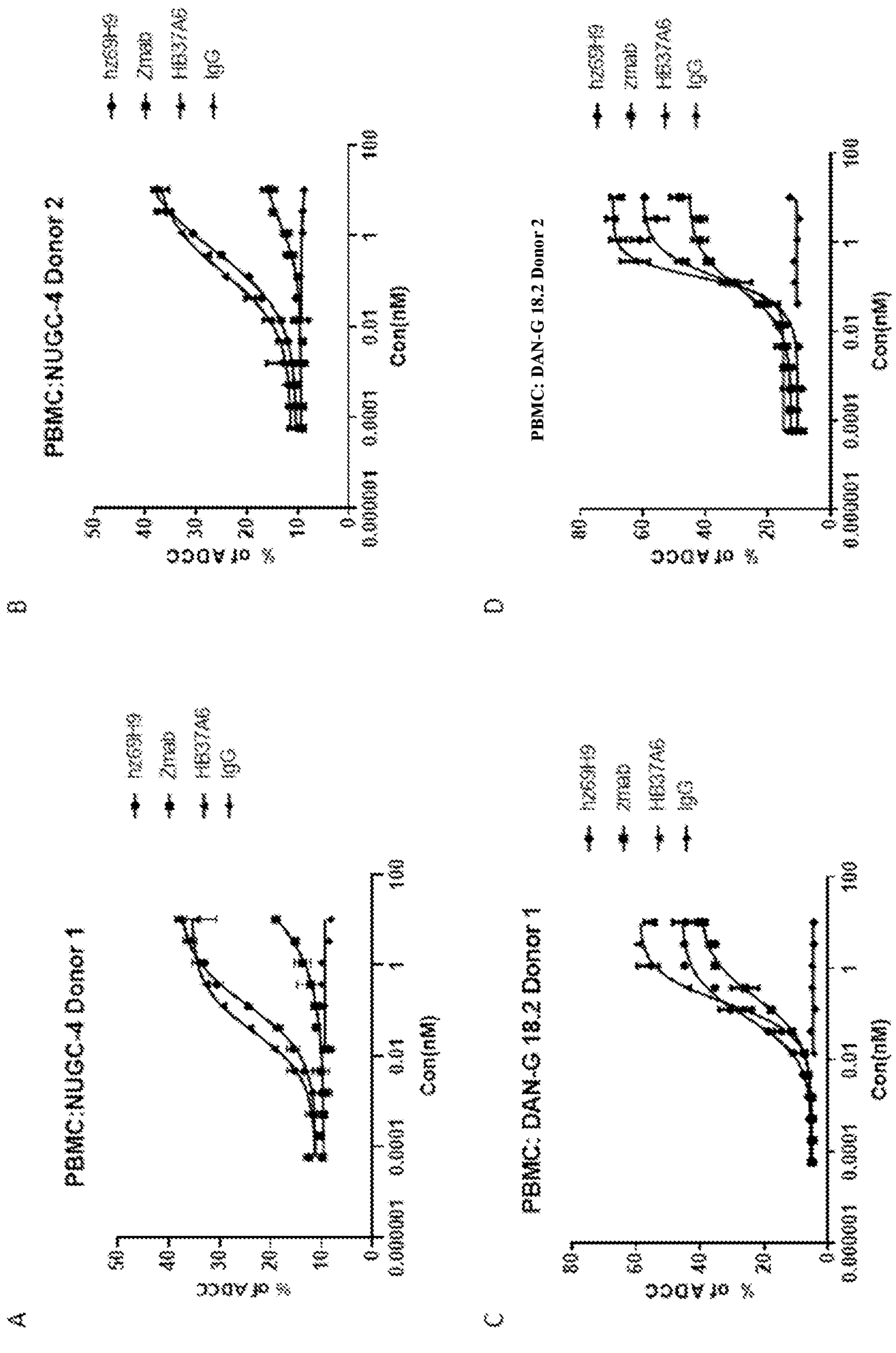
FIG. 7 shows the ADCC activity assay for anti-CLDN18.2 antibodies.

The results of anti-Claudin18.2 monoclonal antibody-dependent cell-mediated NUGC-4 tumor cytotoxicity are shown in FIGS. 7A and 7B, where Hz69H9 and HB37A6 as well as the control antibody Zmab can dose-dependently mediate cytotoxic killing of NK cells against NUGC-4 cells, and the maximal killing of Hz69H9 and HB37A6 against the tumor cells is greater than that of the control antibody Zmab. It is shown that Hz69H9 and HB37A6 have stronger cell-mediated tumor cytotoxicity. The results of anti-Claudin18.2 monoclonal antibody-dependent cell-mediated DAN-G tumor cytotoxicity are shown in FIGS. 7C and 7D, where Hz69H9 and HB37A6 as well as the control antibody Zmab can dose-dependently mediate cytotoxic killing of NK cells against the tumor cells, and the maximal killing mediated by HB37A6 and Hz69H9 in PBMCs of two different donors is greater than that of the control antibody Zmab. The above results indicate that Hz69H9 and HB37A6 have stronger cell-mediated tumor cytotoxicity as compared to the control antibody Zmab.

Example 14. In Vivo Anti-Tumor Effect of CLDN18.2 Antibodies

1. Activity of Antibodies on DAN-G-CLDN18.2 Tumor-Bearing Mouse Models

The HZ69H9 and HB37A6 antibodies were selected to test their anti-tumor effect in NOD-SCID mice (60 female NOD-SCID mice (15-18 g) purchased from Beijing Vital River Laboratory Animal Technology Co., Ltd.) with human pancreatic cancer. The human pancreatic cancer cells DAN-G-CLDN18.2 constructed in Example 1 were subcultured conventionally for subsequent in vivo experiments. The cells were collected by centrifugation, and the DAN-G-CLDN18.2 cells were dispersed with PBS (1×) to obtain a suspension with a cell density of $12\times10^5$/mL. The cell suspension was mixed with matrigel at 1:1 to prepare a cell suspension with a cell concentration of $6\times10^5$/mL. On day 0, 0.2 mL of the cell suspension was subcutaneously inoculated into the right abdominal region of each of the NOD-SCID mice to establish DAN-G-CLDN18.2 tumor-bearing mouse models.

The tumor volume of each mouse was measured 5 days after tumor cell inoculation, and the mice with the tumor volume in the range of 43.36 $mm^3$-89.47 $mm^3$ were selected and divided into groups in a serpentine manner according to the size of the tumor volume (8 mice in each group).

The hIgG (Equitech-Bio, batch No. 160308-02), Hz69H9 and HB37A6 as well as the control antibody Zmab were administered, at a dose of 10 mg/kg each time, to the mice on days 5, 9, 12 and 16 after inoculation, and the tumor volume of the mice was monitored 2-3 times per week.

Tumor volume measurement: The maximum length of major axis (L) and maximum length of minor axis (W) of tumors were measured with a vernier caliper, and tumor volume was calculated using the following formula: $V=L\times W^2/2$. The mice were weighted using an electronic balance.

2. Activity of Antibodies on NUCG-4 Tumor-Bearing Mouse Models

The HZ69H9 and HB37A6 antibodies were selected to test their anti-tumor effect in NOG mice (100 female NOG mice (15-18 g) purchased from Beijing Vital River Laboratory Animal Technology Co., Ltd.) with human gastric cancer. The PBMC cells (Allcells) were resuscitated and centrifuged to collect cells. The PBMC cells were dispersed with PBS (1×) to obtain a cell suspension with a cell density of $2.5\times10^6$/mL. On day 0, 0.2 mL of cell suspension was injected into each of the NOG mice via the ophthalmic vein to establish NOG humanized mouse models.

The NUGC-4 cells were resuscitated and subcultured conventionally for subsequent in vivo experiments. The cells were collected by centrifugation, and the NUGC-4 cells were dispersed with PBS (1×) to obtain a suspension with a cell density of $12\times10^6$/mL. The suspension was mixed with the matrigel at 1:1 to prepare a cell suspension with a cell concentration of $6\times10^6$/mL. On day 5, 0.2 mL of the cell suspension was subcutaneously inoculated into the right abdominal region of each of the NOG humanized mice to establish NUCG-4 tumor-bearing mouse models.

The mice were randomly divided into groups on day 1 after inoculation with tumor cells (7 mice per group). The hIgG (Equitech-Bio, batch No. 160308-02), Hz69H9 and HB37A6 as well as the control antibody Zmab were administered, at a dose of 10 mg/kg each time, to the mice on days 1, 5, 8 and 12 after inoculation, and the tumor volume and body weight of the mice were monitored 2-3 times per week. Tumor volume measurement: The maximum length of major axis (L) and maximum length of minor axis (W) of tumors were measured with a vernier caliper, and tumor volume was calculated using the following formula: $V=L\times W^2/2$. The mice were weighted using an electronic balance.

3. Results

Figure 8:
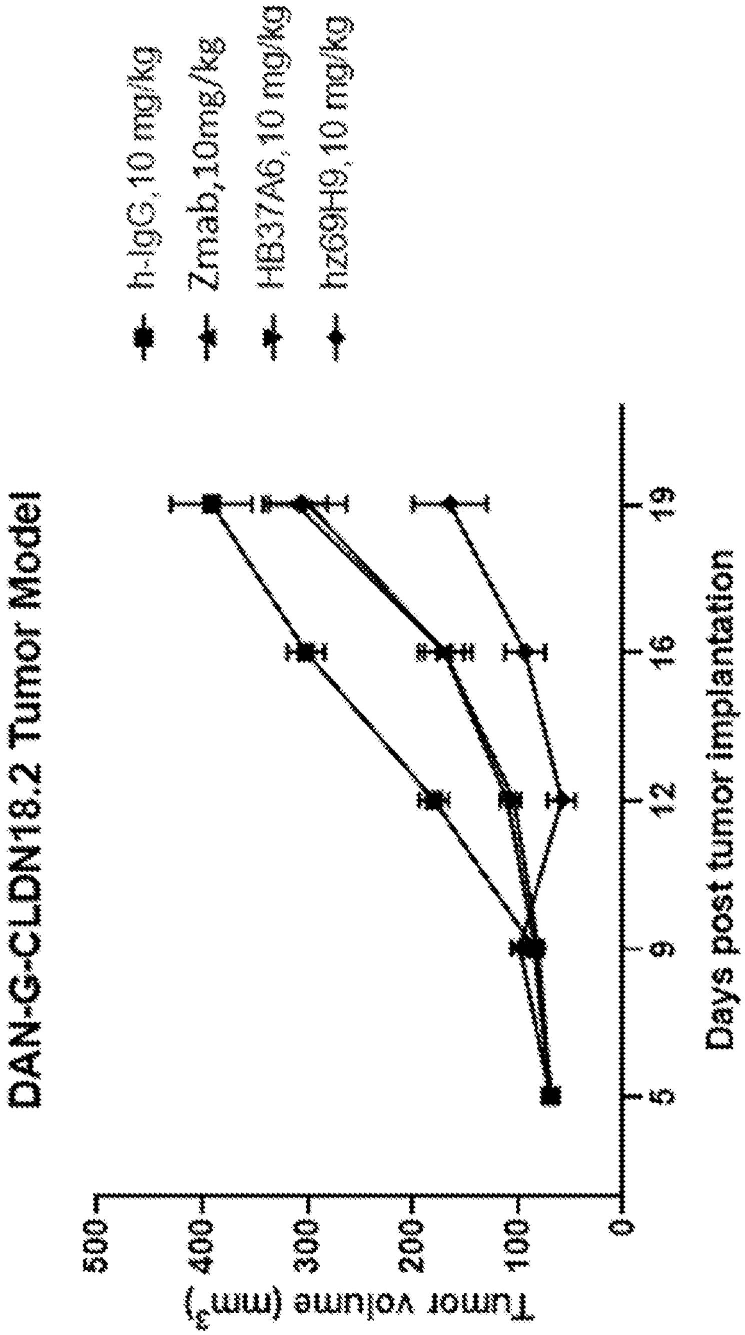
FIG. 8 shows the anti-tumor effect of anti-CLDN18.2 antibodies in mouse models of pancreatic cancer.
Figure 9:
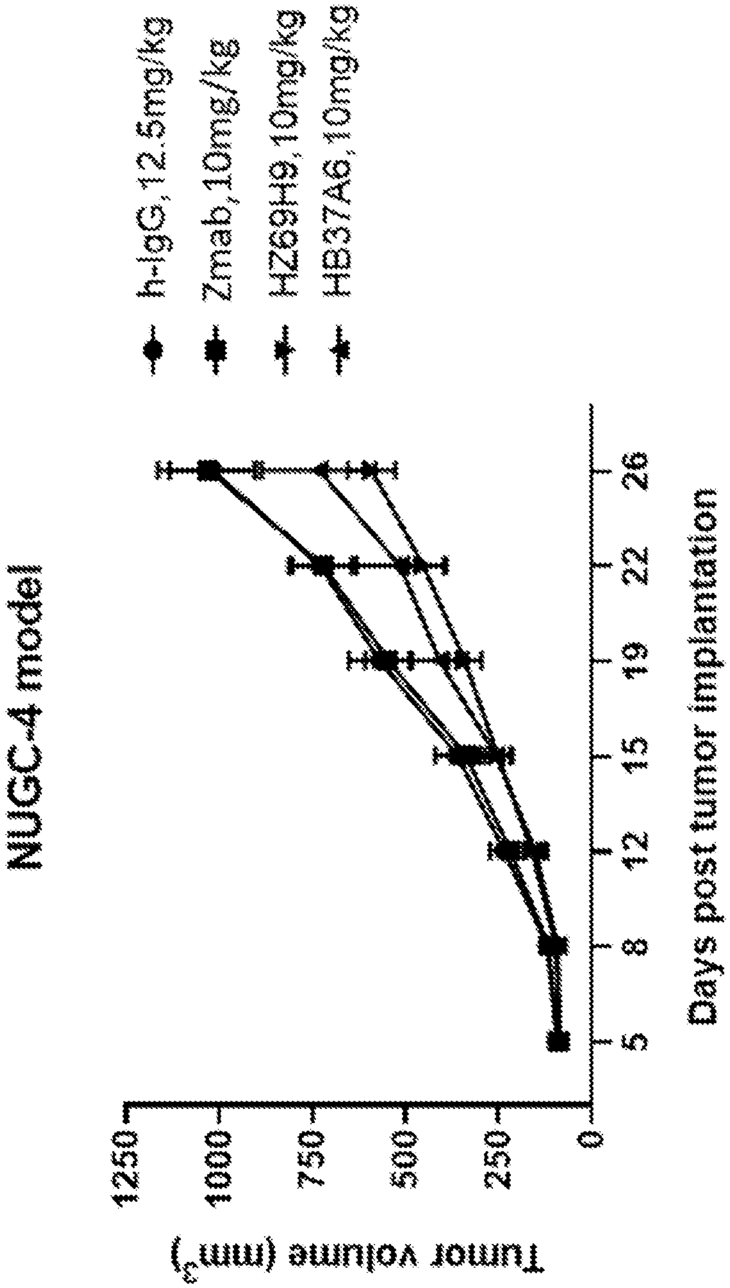
FIG. 9 shows the anti-tumor effect of anti-CLDN18.2 antibodies in mouse models of gastric cancer.

The results are shown in FIG. 8, where Hz69H9 and HB37A6 as well as the control antibody Zmab all can inhibit tumor growth in the human pancreatic cancer DAN-G-hCLDN18.2 mouse models. As shown in FIG. 9, Hz69H9 and HB37A6 show better anti-tumor effect than that of the control antibody Zmab in the human gastric cancer NUGC-4 mouse models.

The relative tumor growth inhibition (TGI %) was calculated on day 26 of inoculation, and the calculation formula is as follows:

TGI %=100%×(tumor volume of the control group−tumor volume of the treatment group)/(tumor volume of the control group−tumor volume of the control group before administration).

In the DAN-G-CLDN18.2 tumor-bearing mouse models, the TGIs of Hz69H9 and HB37A6 were 70% and 28%, respectively, and the TGI of Zmab was 24%;

in the NUGC-4 tumor-bearing mouse models, the TGIs of Hz69H9 and HB37A6 were 46% and 31%, respectively, and the TGI of Zmab was 0%.

Sequence Information:

| SEQ ID NO | Antibody | HB37A6 |
|---|---|---|
| 1 | HCDR1 | GFTFSSYVMS |
| 2 | HCDR2 | TISHSGGSTYYADSVKG |
| 3 | HCDR3 | DAPYYDILTGYRY |
| 4 | Heavy chain variable region (VH) | EVQLLDSGGGLVQPGGSLRLSCAASGFTFSSYVMSWVRQAPGKGLN WVSTISHSGGSTYYADSVKGRFTISRDNSKNTLYLQMNSLRAEDTAVY YCAIDAPYYDILTGYRYWGQGTLVTVSS |
| 5 | Heavy chain constant region (HC) | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK KAEPKSCDKTHTCPPCPAPELLGGPSVFLFPPKPKDTLMISRTPEVTCV VVDVSHEDPEVKFNWYVDGVEVHNAKTKPREEQYNSTYRVVSVLTV LHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFF LYSKLTVDKSRWQQGNVFSCSVMHEALHNHYTQKSLSLSPGK |
| 6 | LCDR1 | RASQSISSWLA |
| 7 | LCDR2 | KASSLES |
| 8 | LCDR3 | QQYNSYSYT |
| 9 | Light chain variable region (VL) | DIQMTQSPSTLSASVGDRVTITCRASQSISSWLAWYQQKPGKAPKLLIY KASSLESGVPSRFSGSGSGTEFTLTISSLQPDDFATYYCQQYNSYSYTFG QGTKLEIK |
| 10 | Light chain constant region (LC) | RTVAAPSVFIFPPSDEQLKSGTASVVCLLNNFYPREAKVQWKVDNALQ SGNSQESVTEQDSKDSTYSLSSTLTLSKADYEKHKVYACEVTHQGLSS PVTKSFNRGEC |

| SEQ ID NO | Antibody | 69H9 |
|---|---|---|
| 12 | HCDR1 | GYSFSSYNIH |
| 13 | HCDR2 | YIAPFNGDSRYNQKFKG |
| 14 | HCDR3 | LNRGNSLDY |
| 15 | VH | EVQLQQSGPELMKPGASVKISCKATGYSFSSYNIHWVKQSHGKSLEWI GYIAPFNGDSRYNQKFKGKATVTVDKSSSTAYMHLSSLTSEDSAVYYC GRLNRGNSLDYWGQGTSLTVSS |
| 5 | HC | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK KAEPKSCDKTHTCPPCPAPELLGGPSVFLFPPKPKDTLMISRTPEVTCV VVDVSHEDPEVKFNWYVDGVEVHNAKTKPREEQYNSTYRVVSVLTV LHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFF LYSKLTVDKSRWQQGNVFSCSVMHEALHNHYTQKSLSLSPGK |
| 16 | LCDR1 | KSSQSLFNSGNQRNYLT |
| 17 | LCDR2 | WASTRES |
| 18 | LCDR3 | QNNYIYPLT |
| 19 | VL | DIVMTQSPSSLTVTAGEKVTMSCKSSQSLFNSGNQRNYLTWYQQKPG QPPKLLIYWASTRESGVPDRFTGSGSGTDFTLTISSVQAEDLAFYYCQN NYIYPLTFGAGTKLELK |
| 10 | LC | RTVAAPSVFIFPPSDEQLKSGTASVVCLLNNFYPREAKVQWKVDNALQ SGNSQESVTEQDSKDSTYSLSSTLTLSKADYEKHKVYACEVTHQGLSS PVTKSFNRGEC |

| SEQ ID NO | Antibody | HB37A6 |
|---|---|---|
| 12 | HCDR1 | GYSFSSYNIH |
| 20 | HCDR2 | YIAPFQGDSRYNQKFKG |
| 14 | HCDR3 | LNRGNSLDY |

-continued

| | | |
|---|---|---|
| 21 | VH | QVQLVQSGAEVKKPGSSVKVSCKASGYSFSSYNIHWVRQAPGQGLE WMGYIAPFQGDSRYNQKFKGRVTITADKSTSTAYMELSSLRSEDTAVY YCARLNRGNSLDYWGQGTLVTVSS |
| 5 | HC | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK KAEPKSCDKTHTCPPCPAPELLGGPSVFLFPPKPKDTLMISRTPEVTCV VVDVSHEDPEVKFNWYVDGVEVHNAKTKPREEQYNSTYRVVSVLTV LHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFF LYSKLTVDKSRWQQGNVFSCSVMHEALHNHYTQKSLSLSPGK |
| 16 | LCDR1 | KSSQSLFNSGNQRNYLT |
| 17 | LCDR2 | WASTRES |
| 18 | LCDR3 | QNNYIYPLT |
| 22 | VL | DIVMTQSPDSLAVSLGERATINCKSSQSLFNSGNQRNYLTWYQQKPGQ PPKLLIYWASTRESGVPDRFSGSGSGTDFTLTISSLQAEDVAVYYCQNN YIYPLTFGGGTKVEIK |
| 10 | LC | RTVAAPSVFIFPPSDEQLKSGTASVVCLLNNFYPREAKVQWKVDNALQ SGNSQESVTEQDSKDSTYSLSSTLTLSKADYEKHKVYACEVTHQGLSS PVTKSFNRGEC |

| SEQ ID NO | Antibody | 38F8 |
|---|---|---|
| 23 | HCDR1 | GFSFSDYGMH |
| 24 | HCDR2 | YINSGSRTLYYADTVKG |
| 25 | HCDR3 | NAYYGNAMDY |
| 26 | VH | EVQLVESGGGLVKPGGSLKLSCAASGFSFSDYGMHWVRQAPEKGLE WIAYINSGSRTLYYADTVKGRFTISRDNAKNTLFLQMTSLRSEETAMY YCTRNAYYGNAMDYWGQGTSVTVSS |
| 5 | HC | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK KAEPKSCDKTHTCPPCPAPELLGGPSVFLFPPKPKDTLMISRTPEVTCV VVDVSHEDPEVKFNWYVDGVEVHNAKTKPREEQYNSTYRVVSVLTV LHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFF LYSKLTVDKSRWQQGNVFSCSVMHEALHNHYTQKSLSLSPGK |
| 28 | LCDR1 | KSSQSLLNSGNQRNYLT |
| 29 | LCDR2 | WSSTRGS |
| 30 | LCDR3 | QNVYYYPFT |
| 31 | VL | DIQMTQSPSSLTVTAGEKVTMSCKSSQSLLNSGNQRNYLTWYQQIPGQ PPKLLIYWSSTRGSGVPDRFTGSGSGTDFTLTISSVQAEDLAVYFCQNV YYYPFTFGSGTRLEVK |
| 10 | LC | RTVAAPSVFIFPPSDEQLKSGTASVVCLLNNFYPREAKVQWKVDNALQ SGNSQESVTEQDSKDSTYSLSSTLTLSKADYEKHKVYACEVTHQGLSS PVTKSFNRGEC |

| SEQ ID NO | Antibody | Hz38F8 |
|---|---|---|
| 23 | HCDR1 | GFSFSDYGMH |
| 24 | HCDR2 | YINSGSRTLYYADTVKG |
| 25 | HCDR3 | NAYYGNAMDY |
| 27 | VH | EVQLVESGGGLVQPGGSLRLSCAASGFSFSDYGMHWVRQAPGKGLE WVSYINSGSRTLYYADTVKGRFTISRDNAKNSLYLQMNSLRDEDTAVY YCARNAYYGNAMDYWGQGTLVTVSS |
| 5 | HC | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK KAEPKSCDKTHTCPPCPAPELLGGPSVFLFPPKPKDTLMISRTPEVTCV VVDVSHEDPEVKFNWYVDGVEVHNAKTKPREEQYNSTYRVVSVLTV LHQDWLNGKEYKCKVSNKALPAPIEKTISKAKGQPREPQVYTLPPSRD |

-continued

| | | |
|---|---|---|
| | | ELTKNQVSLTCLVKGFYPSDIAVEWESNGQPENNYKTTPPVLDSDGSFF LYSKLTVDKSRWQQGNVFSCSVMHEALHNHYTQKSLSLSPGK |
| 28 | LCDR1 | KSSQSLLNSGNQRNYLT |
| 29 | LCDR2 | WSSTRGS |
| 30 | LCDR3 | QNVYYYPFT |
| 32 | VL | DIVMTQSPDSLAVSLGERATINCKSSQSLLNSGNQRNYLTWYQQKPGQ PPKLLIYWSSTRGSGVPDRFSGSGSGTDFTLTISSLQAEDVAVYYCQNV YYYPFTFGQGTRLEIK |
| 10 | LC | RTVAAPSVFIFPPSDEQLKSGTASVVCLLNNFYPREAKVQWKVDNALQ SGNSQESVTEQDSKDSTYSLSSTLTLSKADYEKHKVYACEVTHQGLSS PVTKSFNRGEC |

| SEQ ID NO | Antibody | 59C1 |
|---|---|---|
| 33 | HCDR1 | GYSITSGYGWN |
| 34 | HCDR2 | YIHFSGSTNYNPSLKS |
| 35 | HCDR3 | SGKGNAMDY |
| 36 | VH | QVQLKESGPDLVKPSQSLSLTCTVTGYSITSGYGWNWIRQFPGNKLEW MGYIHFSGSTNYNPSLKSRISITRDTSKNQFFLQLNSVTTEDTATYYCA RSGKGNAMDYWGQGTSVTVSS |
| 5 | HC | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK KAEPKSCDKTHTCPPCPAPELLGGPSVFLFPPKPKDTLMISRTPEVTCV VVDVSHEDPEVKFNWYVDGVEVHNAKTKPREEQYNSTYRVVSVLTV LHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFF LYSKLTVDKSRWQQGNVFSCSVMHEALHNHYTQKSLSLSPGK |
| 38 | LCDR1 | KSSQSLLNSGNQKNYLT |
| 17 | LCDR2 | WASTRES |
| 39 | LCDR3 | QNDYYFPFT |
| 40 | VL | DIQMTQSPSSLTVTAGEKVTMSCKSSQSLLNSGNQKNYLTWYQQKPG QPPKLLIYWASTRESGVPDRFTGSGSGTDFTLTVINMQAEDLALYYCQ NDYYFPFTFGSGTKLEIK |
| 10 | LC | RTVAAPSVFIFPPSDEQLKSGTASVVCLLNNFYPREAKVQWKVDNALQ SGNSQESVTEQDSKDSTYSLSSTLTLSKADYEKHKVYACEVTHQGLSS PVTKSFNRGEC |

| SEQ ID NO | Antibody | Hz59C1 |
|---|---|---|
| 33 | HCDR1 | GYSITSGYGWN |
| 34 | HCDR2 | YIHFSGSTNYNPSLKS |
| 35 | HCDR3 | SGKGNAMDY |
| 37 | VH | QVQLQESGPGLVKPSETLSLTCTVSGYSITSGYGWNWIRQPPGKGLEW IGYIHFSGSTNYNPSLKSRVTISVDTSKNQFSLKLSSVTAADTAVYYCA RSGKGNAMDYWGQGTLVTVSS |
| 5 | HC | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK KAEPKSCDKTHTCPPCPAPELLGGPSVFLFPPKPKDTLMISRTPEVTCV VVDVSHEDPEVKFNWYVDGVEVHNAKTKPREEQYNSTYRVVSVLTV LHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFF LYSKLTVDKSRWQQGNVFSCSVMHEALHNHYTQKSLSLSPGK |
| 38 | LCDR1 | KSSQSLLNSGNQKNYLT |
| 17 | LCDR2 | WASTRES |
| 39 | LCDR3 | QNDYYFPFT |

-continued

| | | |
|---|---|---|
| 41 | VL | DIVMTQSPDSLAVSLGERATINCKSSQSLLNSGNQKNYLTWYQQKPGQ PPKLLIYWASTRESGVPDRFSGSGSGTDFTLTISSLQAEDVAVYYCQND YYFPFTFGGGTKVEIK |
| 10 | LC | RTVAAPSVFIFPPSDEQLKSGTASVVCLLNNFYPREAKVQWKVDNALQ SGNSQESVTEQDSKDSTYSLSSTLTLSKADYEKHKVYACEVTHQGLSS PVTKSFNRGEC |

| SEQ ID NO | Antibody | 51H10 |
|---|---|---|
| 42 | HCDR1 | GYTFTKYIIQ |
| 43 | HCDR2 | YINPYNDDTKYNEKFKG |
| 44 | HCDR3 | TYYGNSFPN |
| 45 | VH | EVQLQQSVPELVKPGASVRMSCKASGYTFTKYIIQWVKQKPGQGLEW IAYINPYNDDTKYNEKFKGKATLTSDKSASTAYMELSSLTSEDSAVYYC ATTYYGNSFPNWGQGTLVTVSA |
| 5 | HC | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK KAEPKSCDKTHTCPPCPAPELLGGPSVFLFPPKPKDTLMISRTPEVTCV VVDVSHEDPEVKFNWYVDGVEVHNAKTKPREEQYNSTYRVVSVLTV LHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFF LYSKLTVDKSRWQQGNVFSCSVMHEALHNHYTQKSLSLSPGK |
| 38 | LCDR1 | KSSQSLLNSGNQKNYLT |
| 17 | LCDR2 | WASTRES |
| 46 | LCDR3 | QNDYSFPFT |
| 47 | VL | DIVMTQSPSSLTVTAGERVTMTCKSSQSLLNSGNQKNYLTWYQQKPG QPPKLLIYWASTRESGVPDRFTGSGSGTDFTLTISSLQSEDLAVYFCQN DYSFPFTFGSGTKLEIK |
| 10 | LC | RTVAAPSVFIFPPSDEQLKSGTASVVCLLNNFYPREAKVQWKVDNALQ SGNSQESVTEQDSKDSTYSLSSTLTLSKADYEKHKVYACEVTHQGLSS PVTKSFNRGEC |

| SEQ ID NO | Antibody | Hz51H10 |
|---|---|---|
| 42 | HCDR1 | GYTFTKYIIQ |
| 43 | HCDR2 | YINPYNDDTKYNEKFKG |
| 44 | HCDR3 | TYYGNSFPN |
| 48 | VH | QVQLVQSGAEVKKPGASVKVSCKASGYTFTKYIIQWVRQAPGQRLE WMGYINPYNDDTKYNEKFKGRVTITRDTSASTAYMELSSLRSEDMAV YYCARTYYGNSFPNWGQGTLVTVSS |
| 5 | HC | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK KAEPKSCDKTHTCPPCPAPELLGGPSVFLFPPKPKDTLMISRTPEVTCV VVDVSHEDPEVKFNWYVDGVEVHNAKTKPREEQYNSTYRVVSVLTV LHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFF LYSKLTVDKSRWQQGNVFSCSVMHEALHNHYTQKSLSLSPGK |
| 38 | LCDR1 | KSSQSLLNSGNQKNYLT |
| 17 | LCDR2 | WASTRES |
| 46 | LCDR3 | QNDYSFPFT |
| 49 | VL | DIVMTQSPDSLAVSLGERATINCKSSQSLLNSGNQKNYLTWYQQKPGQ PPKLLIYWASTRESGVPDRFSGSGSGTDFTLTISSLQAEDVAVYYCQND YSFPFTFGGGTKVEIK |
| 10 | LC | RTVAAPSVFIFPPSDEQLKSGTASVVCLLNNFYPREAKVQWKVDNALQ SGNSQESVTEQDSKDSTYSLSSTLTLSKADYEKHKVYACEVTHQGLSS PVTKSFNRGEC |

-continued

| SEQ ID NO | Antibody | 46F6 |
|---|---|---|
| 50 | HCDR1 | GFSLTDYGVS |
| 51 | HCDR2 | VMWGGGNTYYNSALKS |
| 52 | HCDR3 | QRYGGNAMDY |
| 53 | VH | QVQLKESGPGLVAPSQSLSITCTVSGFSLTDYGVSWIRQPPGKGLEWLG VMWGGGNTYYNSALKSRLSISKDNSKSQVFLKMNSLQSDDTAMYYC AKQRYGGNAMDYWGQGTSVTVSS |
| 5 | HC | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK KAEPKSCDKTHTCPPCPAPELLGGPSVFLFPPKPKDTLMISRTPEVTCV VVDVSHEDPEVKFNWYVDGVEVHNAKTKPREEQYNSTYRVVSVLTV LHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFF LYSKLTVDKSRWQQGNVFSCSVMHEALHNHYTQKSLSLSPGK |
| 28 | LCDR1 | KSSQSLLNSGNQRNYLT |
| 17 | LCDR2 | WASTRES |
| 54 | LCDR3 | QNSYFYPFT |
| 55 | VL | DIQMTQSPSSLTVTAGEKVTMSCKSSQSLLNSGNQRNYLTWYQQIPGQ PPKLLIYWASTRESGVPNRFTGSGSGAEFTLTISSVQTEDLAVYYCQNS YFYPFTFGAGTKLELK |
| 10 | LC | RTVAAPSVFIFPPSDEQLKSGTASVVCLLNNFYPREAKVQWKVDNALQ SGNSQESVTEQDSKDSTYSLSSTLTLSKADYEKHKVYACEVTHQGLSS PVTKSFNRGEC |

| SEQ ID NO | Antibody | Hz46F6 |
|---|---|---|
| 50 | HCDR1 | GFSLTDYGVS |
| 51 | HCDR2 | VMWGGGNTYYNSALKS |
| 52 | HCDR3 | QRYGGNAMDY |
| 56 | VH | QVQLQESGPGLVKPSETLSLTCTVSGFSLTDYGVSWIRQPPGKGLEWIG VMWGGGNTYYNSALKSRVTISVDTSKNQFSLKLSSVTAADTAVYYCA RQRYGGNAMDYWGQGTLVTVSS |
| 5 | HC | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK KAEPKSCDKTHTCPPCPAPELLGGPSVFLFPPKPKDTLMISRTPEVTCV VVDVSHEDPEVKFNWYVDGVEVHNAKTKPREEQYNSTYRVVSVLTV LHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFF LYSKLTVDKSRWQQGNVFSCSVMHEALHNHYTQKSLSLSPGK |
| 28 | LCDR1 | KSSQSLLNSGNQRNYLT |
| 17 | LCDR2 | WASTRES |
| 54 | LCDR3 | QNSYFYPFT |
| 57 | VL | DIVMTQSPDSLAVSLGERATINCKSSQSLLNSGNQRNYLTWYQQKPGQ PPKLLIYWASTRESGVPDRFSGSGSGTDFTLTISSLQAEDVAVYYCQNS YFYPFTFGGGTKVEIK |
| 10 | LC | RTVAAPSVFIFPPSDEQLKSGTASVVCLLNNFYPREAKVQWKVDNALQ SGNSQESVTEQDSKDSTYSLSSTLTLSKADYEKHKVYACEVTHQGLSS PVTKSFNRGEC |

| SEQ ID NO | Antibody | 25C7 |
|---|---|---|
| 58 | HCDR1 | GFTFSDYGMA |
| 59 | HCDR2 | FINNLAYSIYYVDTVTG |
| 60 | HCDR3 | FTTGNVMDY |

-continued

| | | |
|---|---|---|
| 61 | VH | EVMLVESGGGLVQPGGSRKLSCAASGFTFSDYGMAWVRQAPGKGPE WVAFINNLAYSIYYVDTVTGRFTISRENAKDTLYLEMSSLRSEDTALYY CARFTTGNVMDYWGQGTSVTVSS |
| 5 | HC | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK KAEPKSCDKTHTCPPCPAPELLGGPSVFLFPPKPKDTLMISRTPEVTCV VVDVSHEDPEVKFNWYVDGVEVHNAKTKPREEQYNSTYRVVSVLTV LHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFF LYSKLTVDKSRWQQGNVFSCSVMHEALHNHYTQKSLSLSPGK |
| 62 | LCDR1 | KSSQSLLNGGNQKNYLT |
| 63 | LCDR2 | WSSTRES |
| 64 | LCDR3 | QNSYSYPLT |
| 65 | VL | DIVMTQSPSSLTVTAGEKVTMTCKSSQSLLNGGNQKNYLTWYQQKPG QPPKLLIYWSSTRESGVPDRFTGSGSGTDFTLTITSVQAEDLAVYYCQN SYSYPLTFGSGTKLELK |
| 10 | LC | RTVAAPSVFIFPPSDEQLKSGTASVVCLLNNFYPREAKVQWKVDNALQ SGNSQESVTEQDSKDSTYSLSSTLTLSKADYEKHKVYACEVTHQGLSS PVTKSFNRGEC |

| SEQ ID NO | Antibody | Hz25C7 |
|---|---|---|
| 58 | HCDR1 | GFTFSDYGMA |
| 59 | HCDR2 | FINNLAYSIYYVDTVTG |
| 60 | HCDR3 | FTTGNVMDY |
| 66 | VH | EVQLVESGGGLVQPGGSLRLSCAASGFTFSDYGMAWVRQAPGKGLE WVAFINNLAYSIYYVDTVTGRFTISRDNAKNSLYLQMNSLRAEDTAVY YCARFTTGNVMDYWGQGTLVTVSS |
| 5 | HC | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK KAEPKSCDKTHTCPPCPAPELLGGPSVFLFPPKPKDTLMISRTPEVTCV VVDVSHEDPEVKFNWYVDGVEVHNAKTKPREEQYNSTYRVVSVLTV LHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFF LYSKLTVDKSRWQQGNVFSCSVMHEALHNHYTQKSLSLSPGK |
| 67 | LCDR1 | KSSQSLLQGGNQKNYLT |
| 63 | LCDR2 | WSSTRES |
| 64 | LCDR3 | QNSYSYPLT |
| 68 | VL | DIVMTQSPDSLAVSLGERATINCKSSQSLLQGGNQKNYLTWYQQKPG QPPKLLIYWSSTRESGVPDRFSGSGSGTDFTLTISSLQAEDVAVYYCQN SYSYPLTFGGGTKVEIK |
| 10 | LC | RTVAAPSVFIFPPSDEQLKSGTASVVCLLNNFYPREAKVQWKVDNALQ SGNSQESVTEQDSKDSTYSLSSTLTLSKADYEKHKVYACEVTHQGLSS PVTKSFNRGEC |

| SEQ ID NO | Antibody | 3G3 |
|---|---|---|
| 69 | HCDR1 | GYSFTTYWMH |
| 70 | HCDR2 | LIDPSDSETRLNQKFKD |
| 71 | HCDR3 | NRWLLG |
| 72 | VH | QVQLQQSGPQLVRPGASVKISCKASGYSFTTYWMHWVKQRPGQGLE WIGLIDPSDSETRLNQKFKDKATLTVDKSSSTAYMRLSSPTSEDSAVYY CASNRWLLGWGQGTLVTVSS |
| 5 | HC | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK KAEPKSCDKTHTCPPCPAPELLGGPSVFLFPPKPKDTLMISRTPEVTCV VVDVSHEDPEVKFNWYVDGVEVHNAKTKPREEQYNSTYRVVSVLTV LHQDWLNGKEYKCKVSNKALPAPIEKTISKAKGQPREPQVYTLPPSRD |

-continued

| | | |
|---|---|---|
| | | ELTKNQVSLTCLVKGFYPSDIAVEWESNGQPENNYKTTPPVLDSDGSFF LYSKLTVDKSRWQQGNVFSCSVMHEALHNHYTQKSLSLSPGK |
| 38 | LCDR1 | KSSQSLLNSGNQKNYLT |
| 17 | LCDR2 | WASTRES |
| 74 | LCDR3 | QNDYSYPLT |
| 75 | VL | DIQMIQSPSSLTVTAGEKVTMSCKSSQSLLNSGNQKNYLTWYQQKPG QPPKLLIYWASTRESGVPDRFTGSGSGTDFTLTISSVQTEDLAVYYCQN DYSYPLTFGAGTKLEIK |
| 10 | LC | RTVAAPSVFIFPPSDEQLKSGTASVVCLLNNFYPREAKVQWKVDNALQ SGNSQESVTEQDSKDSTYSLSSTLTLSKADYEKHKVYACEVTHQGLSS PVTKSFNRGEC |

| SEQ ID NO | Antibody | Hz3G3 |
|---|---|---|
| 69 | HCDR1 | GYSFTTYWMH |
| 70 | HCDR2 | LIDPSDSETRLNQKFKD |
| 71 | HCDR3 | NRWLLG |
| 73 | VH | QVQLVQSGAEVKKPGASVKVSCKASGYSFTTYWMHWVRQAPGQGL EWMGLIDPSDSETRLNQKFKDRVTMTVDTSTSTVYMELSSLRSEDTAV YYCASNRWLLGWGQGTLVTVSS |
| 5 | HC | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK KAEPKSCDKTHTCPPCPAPELLGGPSVFLFPPKPKDTLMISRTPEVTCV VVDVSHEDPEVKFNWYVDGVEVHNAKTKPREEQYNSTYRVVSVLTV LHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFF LYSKLTVDKSRWQQGNVFSCSVMHEALHNHYTQKSLSLSPGK |
| 38 | LCDR1 | KSSQSLLNSGNQKNYLT |
| 17 | LCDR2 | WASTRES |
| 74 | LCDR3 | QNDYSYPLT |
| 76 | VL | DIVMTQSPDSLAVSLGERATINCKSSQSLLNSGNQKNYLTWYQQKPGQ PPKLLIYWASTRESGVPDRFSGSGSGTDFTLTISSLQAEDVAVYYCQND YSYPLTFGQGTKLEIK |
| 10 | LC | RTVAAPSVFIFPPSDEQLKSGTASVVCLLNNFYPREAKVQWKVDNALQ SGNSQESVTEQDSKDSTYSLSSTLTLSKADYEKHKVYACEVTHQGLSS PVTKSFNRGEC |

| SEQ ID NO | Antibody | 14A5 |
|---|---|---|
| 77 | HCDR1 | GFSLNSYGVG |
| 78 | HCDR2 | VIWGDGSTNYHSVLIS |
| 79 | HCDR3 | ITRGNAMDY |
| 80 | VH | QVQLKESGPGLVAPSQSLSITCSVSGFSLNSYGVGWVRQPPGKGLEWL GVIWGDGSTNYHSVLISRLSIRKDNSKSQVFLKLNSLQTDDTATYYCA MITRGNAMDYWGQGTSVTVSS |
| 5 | HC | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK KAEPKSCDKTHTCPPCPAPELLGGPSVFLFPPKPKDTLMISRTPEVTCV VVDVSHEDPEVKFNWYVDGVEVHNAKTKPREEQYNSTYRVVSVLTV LHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFF LYSKLTVDKSRWQQGNVFSCSVMHEALHNHYTQKSLSLSPGK |
| 28 | LCDR1 | KSSQSLLNSGNQRNYLT |
| 81 | LCDR2 | WASTRKS |
| 82 | LCDR3 | QNNYLFPLT |

-continued

| | | |
|---|---|---|
| 83 | VL | DIVMTQSPSSLTVTAGEKITMSCKSSQSLLNSGNQRNYLTWYQQKPGQ TPKLLIYWASTRKSGVPDRFTGSGSGTDFTLTISSVQAEDLAVYSCQNN YLFPLTFGAGTKLELK |
| 10 | LC | RTVAAPSVFIFPPSDEQLKSGTASVVCLLNNFYPREAKVQWKVDNALQ SGNSQESVTEQDSKDSTYSLSSTLTLSKADYEKHKVYACEVTHQGLSS PVTKSFNRGEC |

| SEQ ID NO | Antibody | Hz14A5 |
|---|---|---|
| 77 | HCDR1 | GFSLNSYGVG |
| 84 | HCDR2 | VIWGDVSTNYHSVLIS |
| 79 | HCDR3 | ITRGNAMDY |
| 85 | VH | QVQLQESGPGLVKPSETLSLTCTVSGFSLNSYGVGWIRQPPGKGLEWI GVIWGDVSTNYHSVLISRVTISKDTSKNQVSLKLSSVTAADTAVYYCA RITRGNAMDYWGQGTLVTVSS |
| 5 | HC | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK KAEPKSCDKTHTCPPCPAPELLGGPSVFLFPPKPKDTLMISRTPEVTCV VVDVSHEDPEVKFNWYVDGVEVHNAKTKPREEQYNSTYRVVSVLTV LHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFF LYSKLTVDKSRWQQGNVFSCSVMHEALHNHYTQKSLSLSPGK |
| 28 | LCDR1 | KSSQSLLNSGNQRNYLT |
| 81 | LCDR2 | WASTRKS |
| 82 | LCDR3 | QNNYLFPLT |
| 86 | VL | DIVMTQSPDSLAVSLGERATINCKSSQSLLNSGNQRNYLTWYQQKPGQ PPKLLIYWASTRKSGVPDRFSGSGSGTDFTLTISSLQAEDVAVYYCQNN YLFPLTFGGGTKVEIK |
| 10 | LC | RTVAAPSVFIFPPSDEQLKSGTASVVCLLNNFYPREAKVQWKVDNALQ SGNSQESVTEQDSKDSTYSLSSTLTLSKADYEKHKVYACEVTHQGLSS PVTKSFNRGEC |

| SEQ ID NO | Antibody | Positive control antibody Zmab |
|---|---|---|
| 87 | HCDR1 | GYTFTSYWIN |
| 88 | HCDR2 | NIYPSDSYTNYNQKFK |
| 89 | HCDR3 | SWRGNSFDY |
| 90 | VH | QVQLQQPGAELVRPGASVKLSCKASGYTFTSYWINWVKQRPGQGLE WIGNIYPSDSYTNYNQKFKDKATLTVDKSSSTAYMQLSSPTSEDSAVY YCTRSWRGNSFDYWGQGTTLTVSS |
| 5 | HC | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK KAEPKSCDKTHTCPPCPAPELLGGPSVFLFPPKPKDTLMISRTPEVTCV VVDVSHEDPEVKFNWYVDGVEVHNAKTKPREEQYNSTYRVVSVLTV LHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFF LYSKLTVDKSRWQQGNVFSCSVMHEALHNHYTQKSLSLSPGK |
| 38 | LCDR1 | KSSQSLLNSGNQKNYLT |
| 17 | LCDR2 | WASTRES |
| 91 | LCDR3 | QNDYSYPFT |
| 92 | VL | DIVMTQSPSSLTVTAGEKVTMSCKSSQSLLNSGNQKNYLTWYQQKPG QPPKLLIYWASTRESGVPDRFTGSGSGTDFTLTISSVQAEDLAVYYCQN DYSYPFTFGSGTKLEIK |
| 10 | LC | RTVAAPSVFIFPPSDEQLKSGTASVVCLLNNFYPREAKVQWKVDNALQ SGNSQESVTEQDSKDSTYSLSSTLTLSKADYEKHKVYACEVTHQGLSS PVTKSFNRGEC |

The invention claimed is:

1. An anti-claudin18.2(CLDN18.2) antibody or an antigen-binding fragment thereof, comprising:

three complementarity determining regions HCDR1, HCDR2 and HCDR3 contained in a VH set forth in SEQ ID NO: 4, and three complementarity determining regions LCDR1, LCDR2 and LCDR3 contained in a VL set forth in SEQ ID NO: 9.

2. An anti-CLDN18.2 antibody or an antigen-binding fragment thereof, comprising:

HCDR1, HCDR2 and HCDR3 set forth in the amino acid sequences of SEQ ID NOs: 1, 2 and 3, respectively, and LCDR1, LCDR2 and LCDR3 set forth in the amino acid sequences of SEQ ID NOs: 6, 7 and 8, respectively.

3. The antibody or the antigen-binding fragment thereof according to claim 1, comprising a heavy chain variable region and/or a light chain variable region, wherein the heavy chain variable region (i) comprises or consists of an amino acid sequence having at least 90% identity to the amino acid sequence set forth in SEQ ID NO: 4; or (ii) comprises or consists of an amino acid sequence having one or no more than 10 amino acid replacements, as compared to the amino acid sequence set forth in SEQ ID NO: 4, wherein the amino acid replacements do not occur in CDRs; and/or the light chain variable region (i) comprises or consists of an amino acid sequence having at least 90% identity to the amino acid sequence set forth in SEQ ID NO: 9; or (ii) comprises or consists of an amino acid sequence having one no more than 10 amino acid replacements, as compared to the amino acid sequence set forth in SEQ ID NO: 9, wherein the amino acid replacements do not occur in CDRs.

4. The antibody or the antigen-binding fragment thereof according to claim 1, comprising:

a VH comprising or consisting of an amino acid sequence having at least 90% identity to the amino acid sequence set forth in SEQ ID NO: 4, and a VL comprising or consisting of an amino acid sequence having at least 90% identity to the amino acid sequence set forth in SEQ ID NO: 9.

5. The antibody or the antigen-binding fragment thereof according to claim 1, further comprising a heavy chain constant region and/or a light chain constant region.

6. The antibody or the antigen-binding fragment thereof according to claim 5, wherein the heavy chain constant region (HC)

(i) comprises or consists of an amino acid sequence having at least 85% identity to the amino acid sequence set forth in SEQ ID NO: 5;

or (ii) comprises or consists of an amino acid sequence having one or no more than 20 amino acid replacements, as compared to the amino acid sequence set forth in SEQ ID NO: 5; and/or the light chain constant region (LC)

(i) comprises or consists of an amino acid sequence having at least 85% identity to the amino acid sequence selected from SEQ ID NO: 10;

or (ii) comprises or consists of an amino acid sequence having one or no more than 20 amino acid replacements, as compared to the amino acid sequence selected from SEQ ID NO: 10.

7. The antibody or the antigen-binding fragment thereof according to claim 6, wherein the amino acid replacements occurs in an Fc region of the heavy chain constant region.

8. The antibody or the antigen-binding fragment thereof according to claim 1, wherein the antibody is an antibody or an antigen-binding fragment in the form of IgG1, IgG2, IgG3 or IgG4.

9. The antibody or the antigen-binding fragment thereof according to claim 1, wherein the antibody is a monoclonal antibody.

10. The antibody or the antigen-binding fragment thereof according to claim 1, wherein the antibody is a human antibody.

11. The antibody or the antigen-binding fragment thereof according to claim 1, wherein the antigen-binding fragment is an antibody fragment selected from: Fab, Fab', Fab'-SH, Fv, scFv, $(Fab')_2$, and a linear antibody.

12. The antibody or the antigen-binding fragment thereof according to claim 4, wherein the antibody or the antigen-binding fragment thereof has one or more of the following properties:

(i) binding to human CLDN18.2, but not binding to human CLDN18.1;

(ii) binding to human CLDN18.2 with an equilibrium dissociation constant ($K_D$) of less than about 15 nM;

(iii) binding to CLDN18.2 on cell surface, but not binding to CLDN18.1 on cell surface;

(iv) having antibody-dependent cell-mediated cytotoxicity (ADCC) activity or complement-dependent cytotoxicity (CDC) activity;

(v) inhibiting tumor cells; and (vi) being capable of effectively inhibiting tumor growth with a tumor growth inhibition of greater than or equal to about 25%.

13. The antibody or the antigen-binding fragment thereof according to claim 1, comprising: a VH comprising or consisting of the amino acid sequence set forth in SEQ ID NO: 4, and a VL comprising or consisting of the amino acid sequence set forth in SEQ ID NO: 9.

14. The antibody or the antigen-binding fragment thereof according to claim 5, wherein the heavy chain constant region (HC) comprises or consists of the amino acid sequence set forth in SEQ ID NO: 5, and the light chain constant region (LC) comprises or consists of the amino acid sequence set forth in SEQ ID NO: 10.

15. An immunoconjugate, comprising the antibody or the antigen-binding fragment thereof according to claim 1 and an additional substance.

16. The immunoconjugate according to claim 15, wherein the additional substance is a cytotoxic agent.

17. A pharmaceutical composition, comprising the antibody or the antigen-binding fragment thereof according to claim 1, and a pharmaceutical supplementary material.

18. A pharmaceutical combination, comprising the antibody or the antigen-binding fragment thereof according to claim 1, and one or more additional therapeutic agents.

19. The pharmaceutical combination according to claim 18, wherein the one or more additional therapeutic agents are selected from the group consisting of a chemotherapeutic agent, a cytokine, a cytotoxic agent, an additional antibody, a small molecule drug, an immunomodulatory agent, and combinations thereof.

20. A method for treating a tumor in a subject, comprising administering to the subject an effective amount of the antibody or the antigen-binding fragment thereof according to claim 4, wherein the tumor expresses CLDN18.2.

21. The method according to claim 20, wherein the tumor is pancreatic cancer or gastric cancer.

22. The method according to claim 20, wherein the method further comprises administering to a patient one or more additional therapies.

23. The method according to claim 22, wherein the one or more therapies are one or more therapeutic modalities and/or an additional therapeutic agent.

24. The method according to claim 23, wherein the one or more therapeutic modalities comprise surgical treatment and/or radiotherapy, and wherein the additional therapeutic agent is selected from the group consisting of a chemotherapeutic agent, a cytokine, a cytotoxic agent, an additional antibody, a small molecule drug, an immunomodulatory agent, and combinations thereof.

25. A method for inducing ADCC and/or CDC in a subject, comprising administering to the subject an effective amount of the antibody or the antigen-binding fragment thereof according to claim 1, wherein the antibody or the antigen-binding fragment thereof comprises an Fc region, and wherein the subject has a tumor, wherein the tumor expresses CLDN18.2.

26. A method for detecting CLDN18.2 in a sample, comprising (a) contacting the sample with the antibody or the antigen-binding fragment thereof according to claim 1 or an immunoconjugate comprising the antibody or the antigen-binding fragment thereof; and (b) detecting a complex formed by the antibody or the antigen-binding fragment thereof and CLDN18.2, wherein, optionally, the antibody is detectably labeled.

* * * * *